US009018391B2

(12) United States Patent
Bukhtiyarov et al.

(10) Patent No.: US 9,018,391 B2
(45) Date of Patent: Apr. 28, 2015

(54) INHIBITORS OF BETA-SECRETASE

(71) Applicants: Yuri Bukhtiyarov, Boothwyn, PA (US); Salvacion Cacatian, Conshohocken, PA (US); Lawrence Wayne Dillard, Yardley, PA (US); Klaus Fuchs, Ingelheim Am Rhein (DE); Lanqi Jia, Horsham, PA (US); Deepak S. Lala, Lower Gwynedd, PA (US); Angel Morales-Ramos, Blue Bell, PA (US); Suresh B. Singh, Kendall Park, NJ (US); Shankar Venkatraman, Lansdale, PA (US); Zhenrong Xu, Chalfont, PA (US); Jing Yuan, Lansdale, PA (US); Yi Zhao, Blue Bell, PA (US); Yajun Zheng, Hockessin (DE); Cornelia Dorner-Ciossek, Ingelheim am Rhein (DE); Ulrike Gross, Ingelheim am Rhein (DE); Niklas Heine, Ingelheim am Rhein (DE); Achim Sauer, Ingelheim am Rhein (DE)

(72) Inventors: Yuri Bukhtiyarov, Boothwyn, PA (US); Salvacion Cacatian, Conshohocken, PA (US); Lawrence Wayne Dillard, Yardley, PA (US); Klaus Fuchs, Ingelheim Am Rhein (DE); Lanqi Jia, Horsham, PA (US); Deepak S. Lala, Lower Gwynedd, PA (US); Angel Morales-Ramos, Blue Bell, PA (US); Suresh B. Singh, Kendall Park, NJ (US); Shankar Venkatraman, Lansdale, PA (US); Zhenrong Xu, Chalfont, PA (US); Jing Yuan, Lansdale, PA (US); Yi Zhao, Blue Bell, PA (US); Yajun Zheng, Hockessin (DE); Cornelia Dorner-Ciossek, Ingelheim am Rhein (DE); Ulrike Gross, Ingelheim am Rhein (DE); Niklas Heine, Ingelheim am Rhein (DE); Achim Sauer, Ingelheim am Rhein (DE)

(73) Assignees: Boehringer Ingelheim International GmbH, Ingelheim Am Rhein (DE); Vitae Pharmaceuticals, Inc., Fort Washington, PA (US)

(*) Notice: Subject to any disclaimer, the term of this patent is extended or adjusted under 35 U.S.C. 154(b) by 0 days.

(21) Appl. No.: 14/011,183

(22) Filed: Aug. 27, 2013

(65) Prior Publication Data
US 2014/0057927 A1     Feb. 27, 2014

Related U.S. Application Data

(60) Provisional application No. 61/693,512, filed on Aug. 27, 2012, provisional application No. 61/788,839, filed on Mar. 15, 2013, provisional application No. 61/816,458, filed on Apr. 26, 2013.

(51) Int. Cl.
C07D 235/02 (2006.01)
C07D 401/06 (2006.01)
C07D 403/04 (2006.01)
C07D 403/06 (2006.01)
C07D 403/14 (2006.01)
C07D 405/06 (2006.01)
C07D 401/14 (2006.01)
A61K 31/4184 (2006.01)

(52) U.S. Cl.
CPC ............ *C07D 405/06* (2013.01); *C07D 235/02* (2013.01); *C07D 403/04* (2013.01); *C07D 401/14* (2013.01); *C07D 401/06* (2013.01); *C07D 403/06* (2013.01); *C07D 403/14* (2013.01); *A61K 31/4184* (2013.01)

(58) Field of Classification Search
USPC ....................................... 548/301.1
See application file for complete search history.

(56) References Cited

U.S. PATENT DOCUMENTS

| 4,874,869 | A | 10/1989 | Ueda et al. |
| 5,430,048 | A | 7/1995 | Gadwood |
| 7,423,158 | B2 | 9/2008 | Malamas et al. |
| 7,607,246 | B2 | 10/2009 | Valiyambath Krishnan et al. |
| 7,872,009 | B2 | 1/2011 | Albrecht et al. |
| 8,426,447 | B2 | 4/2013 | White et al. |
| 8,450,308 | B2 | 5/2013 | Dillard et al. |
| 8,633,212 | B2 | 1/2014 | Cacatian et al. |
| 2005/0282825 | A1 | 12/2005 | Malamas et al. |
| 2005/0282826 | A1 | 12/2005 | Malamas et al. |
| 2006/0111370 | A1 | 5/2006 | Zhu et al. |
| 2006/0281730 | A1 | 12/2006 | Zhu et al. |
| 2006/0287294 | A1 | 12/2006 | Zhu et al. |
| 2007/0004730 | A1 | 1/2007 | Zhou et al. |
| 2007/0004786 | A1 | 1/2007 | Malamas et al. |
| 2007/0027199 | A1 | 2/2007 | Malamas et al. |
| 2007/0072925 | A1 | 3/2007 | Malamas et al. |
| 2007/0203116 | A1 | 8/2007 | Quagliato et al. |
| 2007/0287692 | A1 | 12/2007 | Wu et al. |
| 2009/0209529 | A1 | 8/2009 | Andreini et al. |
| 2011/0071126 | A1 | 3/2011 | Cacatian et al. |
| 2011/0152253 | A1 | 6/2011 | Motoki et al. |
| 2011/0218192 | A1 | 9/2011 | Dillard et al. |
| 2012/0065195 | A1 | 3/2012 | Clark et al. |
| 2012/0087237 | A1 | 4/2012 | Pellizzoni et al. |
| 2013/0053377 | A1 | 2/2013 | Dillard et al. |
| 2013/0289050 | A1 | 10/2013 | Bukhtiyarov et al. |

FOREIGN PATENT DOCUMENTS

WO          9305045 A1      3/1993
WO     WO 95/30642 A1    11/1995
(Continued)

OTHER PUBLICATIONS

CA 149:307845 (Sep. 2008).
(Continued)

*Primary Examiner* — Laura L. Stockton
(74) *Attorney, Agent, or Firm* — McCarter & English, LLP; Steven G. Davis; Xin Zhang

(57) ABSTRACT

The present invention relates to spirocyclic acylguanidines and their use as inhibitors of the β-secretase enzyme (BACE1) activity, pharmaceutical compositions containing the same, and methods of using the same as therapeutic agents in the treatment of neurodegenerative disorders, disorders characterized by cognitive decline, cognitive impairment, dementia and diseases characterized by production of β-amyloid aggregates.

38 Claims, No Drawings

(56) References Cited

FOREIGN PATENT DOCUMENTS

| | | | |
|---|---|---|---|
| WO | 2005058311 A1 | 6/2005 | |
| WO | 2006044497 A2 | 4/2006 | |
| WO | 2006065277 A2 | 6/2006 | |
| WO | 2007016012 A2 | 2/2007 | |
| WO | 2007038271 A1 | 4/2007 | |
| WO | 2007049532 A1 | 5/2007 | |
| WO | 2007063114 A2 | 6/2007 | |
| WO | 2007076284 A2 | 7/2007 | |
| WO | 2007078813 A2 | 7/2007 | |
| WO | 2007100536 A1 | 9/2007 | |
| WO | WO 2008/010481 A1 | 1/2008 | |
| WO | 2008030412 A2 | 3/2008 | |
| WO | 2008076043 A1 | 6/2008 | |
| WO | 2008076044 A1 | 6/2008 | |
| WO | 2008076045 A1 | 6/2008 | |
| WO | 2008076046 A1 | 6/2008 | |
| WO | 2008103351 A2 | 8/2008 | |
| WO | 2008115552 A1 | 9/2008 | |
| WO | 2008118379 A2 | 10/2008 | |
| WO | 2008133273 A1 | 11/2008 | |
| WO | 2008133274 A1 | 11/2008 | |
| WO | 2008150217 A1 | 12/2008 | |
| WO | 2009134617 A1 | 11/2009 | |
| WO | 2010013302 A1 | 2/2010 | |
| WO | 2010013794 A1 | 2/2010 | |
| WO | 2010021680 A2 | 2/2010 | |
| WO | 2010105179 A2 | 9/2010 | |
| WO | 2011072064 A1 | 6/2011 | |
| WO | 2011106414 A1 | 9/2011 | |
| WO | 2012087237 A1 | 6/2012 | |
| WO | 2013134085 A1 | 9/2013 | |

OTHER PUBLICATIONS

CAPLUS 2008:1339943 (Nov. 2008).
Gadwood et al. "Synthesis and Biological Activity of Spirocyclic Benzopyran Imidazolone Potassium Channel Openers," J. Med. Chem., vol. 36(10):1480-1487 (1993).
Hunt, Kevin W., et al, Spirocyclic Beta Site Amyloid Precursor Protein Cleaving Enzyme 1 (BACE1) Inhibitors: From Hit to Lowering of Cerebrospinal Fluid (CSF) Amyloid Beta in a Higher Species, Journal of Medicinal Chemistry 56(8):3379-3403 (2013).
International Search Report for related PCT/US2009/004686; Feb. 12, 2010.
Written Opinion for related PCT/US2009/004686; Feb. 12, 2010.
International Search Report for related PCT/US2010/027173; Sep. 6, 2010.
Written Opinion for related PCT/US2010/027173; Sep. 6, 2010.
International Search Report for related PCT/US2011/025912; Apr. 1, 2011.
Written Opinion for related PCT/US2011/025912; Apr. 1, 2011.
International Search Report for related PCT/US2013/028796: May 3, 2013.
Written Opinion for related PCT/US2011/028796: May 3, 2013.
International Search Report for related PCT/US2013/056566 mailed Nov. 8, 2013.
Written Opinion for related PCT/US2013/056566 mailed Nov. 8, 2013.
Michael S. Malamas et al., Aminoimidazoles as Potent and Selective Human Beta-Secretase (BACE1) Inhibitors; J. Med. Chem. (2009), 52, 6314-6323.
Michael S. Malamas et al.; Design and Synthesis of 5,5'-Disubstituted Aminohydantoins as Potent and Selective Human Beta-Secretase (BACE1) Inhibitors; J. Med. Chem. (2010), 53, 1146-1158.
Michael S. Malamas; Di-substituted pyridinyl aminohydantoins as potent and highly selective human Beta-secretase (BACE1) inhibitors; Bioorganic & Medicinal Chemistry 18 (2010) 630-639.
Pawel Nowak et al.; Discovery and initial optimization of 5,50-disubstituted aminohydantoins as potent b-secretase (BACE1) inhibitors; Bioorganic & Medicinal Chemistry Letters 20 (2010) 632-635.
R. Silvestri, "Boom in the Developemnt of Non-Peptidic β-Secretase (MACE1) Inhibitors for the Treatment of Alzheimer's Disease", Medicinal Research Reviews, (2009), vol. 29, No. 2, 295-338.
Yu-Sen Wang et al.; Application of Fragment-BasedNMR Screening, X-ray Crystallography, Structure-Based Design, and Focused Chemical Library Design to Identify Novel MicroM Leads for the Development of nM BACE-1 ( Beta-Site APP Cleaving Enzyme 1) Inhibitors; J. Med. Chem. (2010), 53, 942-950.
Zhaoning Zhu et al.; Discovery of Cyclic Acylguanidines as Highly Potent and Selective Beta-Site Amyloid Cleaving Enzyme (BACE) Inhibitors: Part I Inhibitor Design and Validation; J. Med. Chem. (2010), 53, 951-965.
International Preliminary Report on Patentability for related International Patent Application No. PCT/US2013/056566, Dated: Aug. 19, 2014.

SEQUENCE LISTING
<160> NUMBER OF SEQ ID NOS: 1
<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic peptide
<400> SEQUENCE: 1
Glu Val Asn Leu Asp Ala Glu Phe Lys
1               5

INHIBITORS OF BETA-SECRETASE

RELATED APPLICATIONS

This application claims the benefit of U.S. Provisional Application Ser. No. 61/693,512, filed Aug. 27, 2012, U.S. Provisional Application Ser. No. 61/788,839, filed Mar. 15, 2013, and U.S. Provisional Application Ser. No. 61/816,458, filed Apr. 26, 2013. The entire teachings of each of the above applications are incorporated herein by reference.

SEQUENCE LISTING

The instant application contains a Sequence Listing which has been submitted in ASCII format via EFS-Web and is hereby incorporated by reference in its entirety. Said ASCII copy, created on Aug. 27, 2013, is named 120573-00504_SL.txt and is 631 bytes in size.

FIELD OF THE INVENTION

The present invention relates to spirocyclic acylguanidines and their use as inhibitors of the β-secretase enzyme (BACE1) activity, pharmaceutical compositions containing the same, and methods of using the same as therapeutic agents in the treatment of neurodegenerative disorders, disorders characterized by cognitive decline, cognitive impairment, dementia and diseases characterized by production of β-amyloid deposits and/or neurofibrillary tangles.

BACKGROUND OF THE INVENTION

β-Amyloid (also referred to herein as "Abeta" or "Aβ") deposits and neurofibrillary tangles are two major pathologic characterizations associated with Alzheimer's disease (AD). Clinically, AD is characterized by the loss of memory, cognition, reasoning, judgment, and orientation. Also affected, as the disease progresses, are motor, sensory and linguistic abilities until global impairment of multiple cognitive functions occurs. These cognitive losses take place gradually, but typically lead to severe impairment and eventual death in 4-12 years.

β-Amyloid deposits are predominantly an aggregate of Abeta peptide, which in turn is a product of the proteolysis of amyloid precursor protein (APP). More specifically, Aβ peptide results from the cleavage of APP at the C-terminals by one or more γ-secretases, and at the N-terminus by β-secretase enzyme (BACE1), also known as aspartyl protease and memapsin2, as part of the β-amyloidogenic pathway.

BACE activity is correlated directly to the generation of Aβ peptide from APP, and studies increasingly indicate that the inhibition of BACE inhibits the production of Aβ peptide.

Amyloidogenic plaques and vascular amyloid angiopathy also characterize the brains of patients with Trisomy 21 (Down Syndrome), Hereditary Cerebral Hemorrhage with Amyloidosis of the Dutch-type (HCHWA-D), and other neurodegenerative disorders. Neurofibrillary tangles also occur in other neurodegenerative disorders including dementia-inducing disorders.

Recently, Abeta has been reported to be implicated in the development of retinal ganglion cell (RGC) apoptosis in glaucoma, with evidence of caspase-3-mediated abnormal amyloid precursor protein processing, increased expression of Abeta in RGCs in experimental glaucoma and decreased vitreous Aβ levels (consistent with retinal Aβ deposition) in patients with glaucoma. Amyloid deposits have also been associated with macular degeneration in patients suffering from dry age-related macular degeneration (AMD) and in animal models of AMD.

WO2010/021680, WO2011/106414 and WO2010/105179 disclose spirocyclic acylguanidines with a spirocyclic scaffold as inhibitors of beta-secretase.

SUMMARY OF THE INVENTION

The present invention provides compounds that are BACE1 inhibitors and are useful as therapeutic agents in the treatment of a disease or disorder characterized by elevated β-amyloid deposits or β-amyloid levels in a patient. The disclosed BACE1 inhibitors have the following characteristics:

(1) High potency of inhibition of BACE1 enzyme activity (assay 1)

(2) High selectivity against the cardiac hERG channel in a cellular assay (assay 2)

(3) Low propensity to cause phospholipidosis in a cellular phospholipidosis assay (assay 3), and (4) High stability against metabolic degradation in hepatocytes (assay 4).

Thus, the present invention provides compounds which show a combination of high potency as BACE1 inhibitors, high selectivity against the cardiac hERG channel, low phospholipidosis activity, and high stability against metabolic degradation.

One embodiment of the invention is a compound represented by a structural formula selected from:

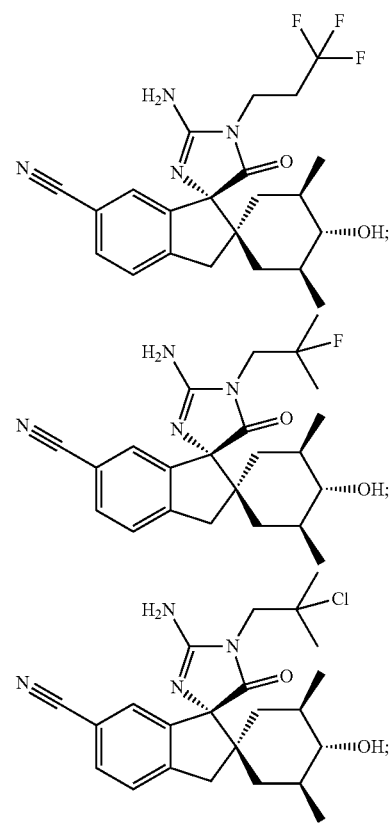

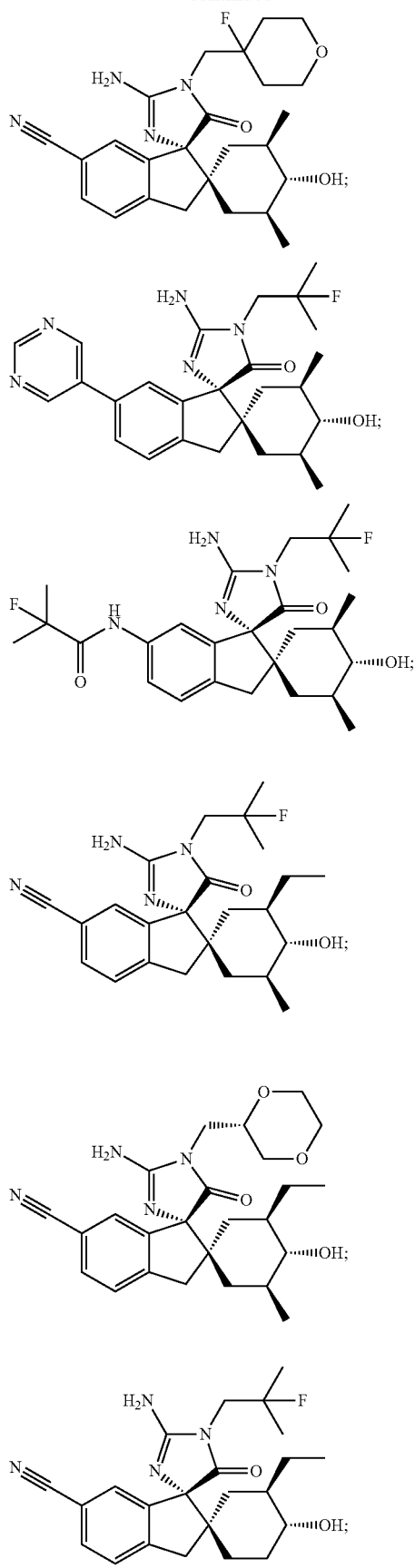
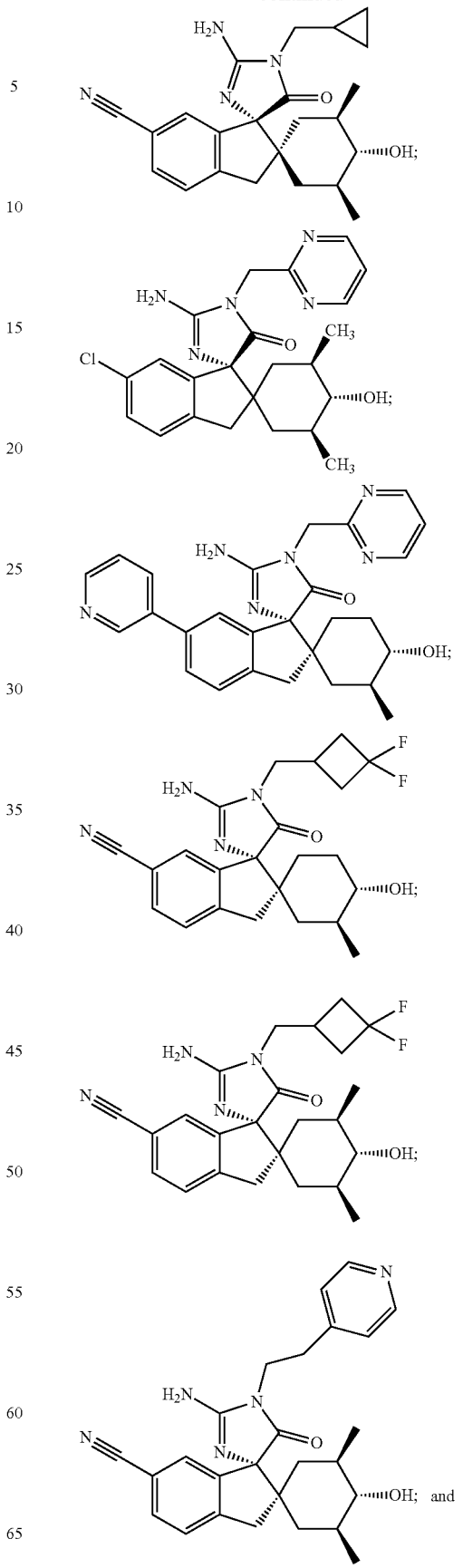

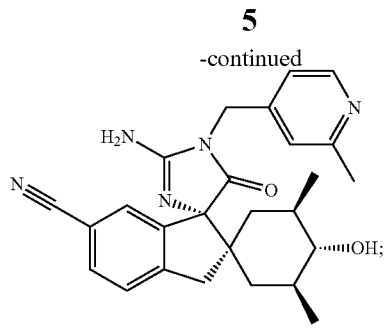

or a pharmaceutically acceptable salt of any of the foregoing compounds. The immediately foregoing compounds are referred to herein as "compounds of the present invention".

Another embodiment of the invention is a compound of the present invention or a pharmaceutically acceptable salt thereof for use as a medicament.

Another embodiment of the invention is a pharmaceutical composition comprising a compound of the present invention or a pharmaceutically acceptable salt thereof in admixture with a pharmaceutically acceptable adjuvant, diluent or carrier.

Another embodiment of the invention is a compound of the present invention or a pharmaceutically acceptable salt thereof for use in the treatment of a BACE1 mediated disorder or disease in a subject.

Another embodiment of the invention is the use of a compound of the present invention or a pharmaceutically acceptable salt thereof for the manufacture of a medicament for the treatment of a BACE1 mediated disorder in a subject.

Another embodiment of the invention is a method of treating a subject with a BACE1 mediated disease or disorder, comprising administering to the subject an effective amount of a compound of the present invention or a pharmaceutically acceptable salt thereof.

Yet another embodiment of the invention is an intermediate used in the preparation of a compound of the present invention. These intermediates are represented by a structural formula selected from:

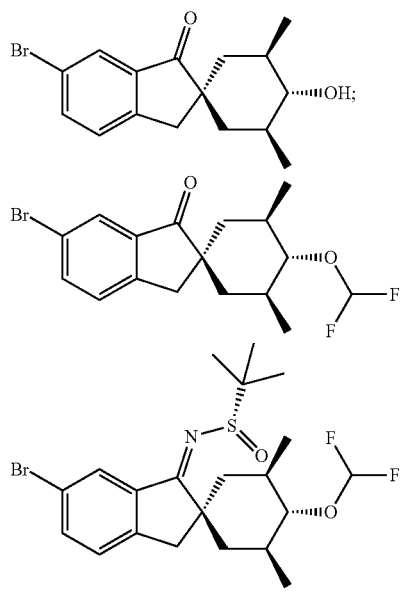

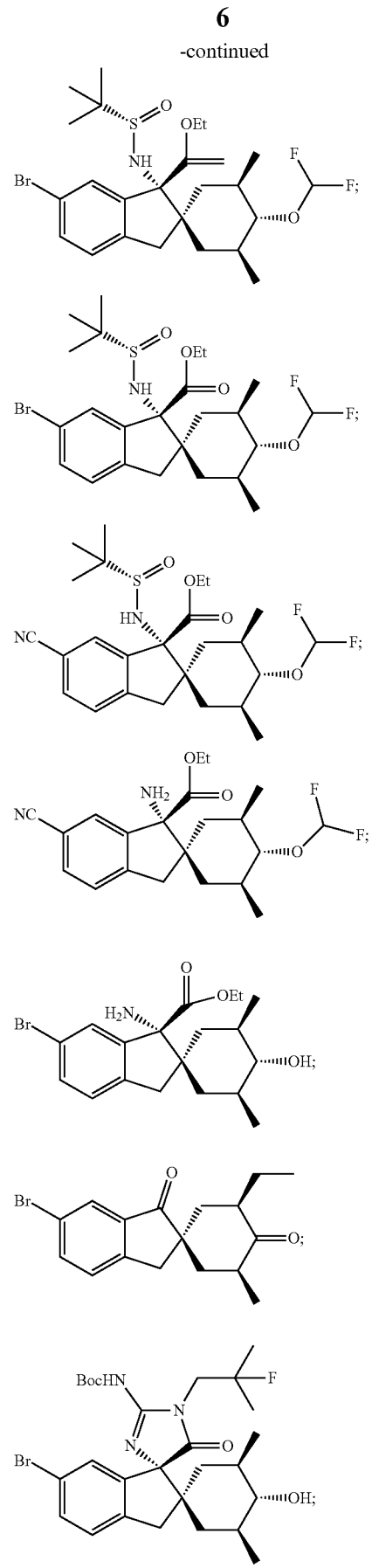

-continued

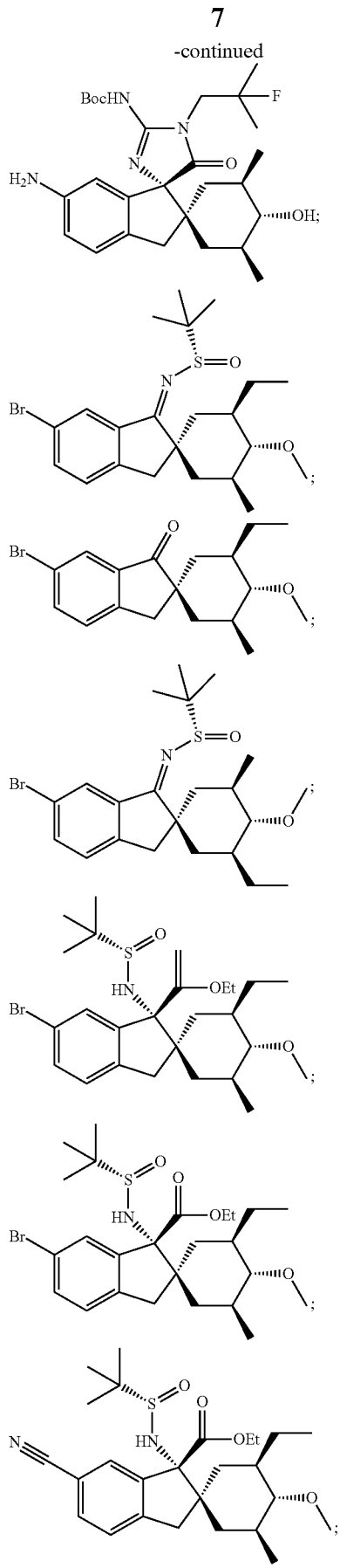

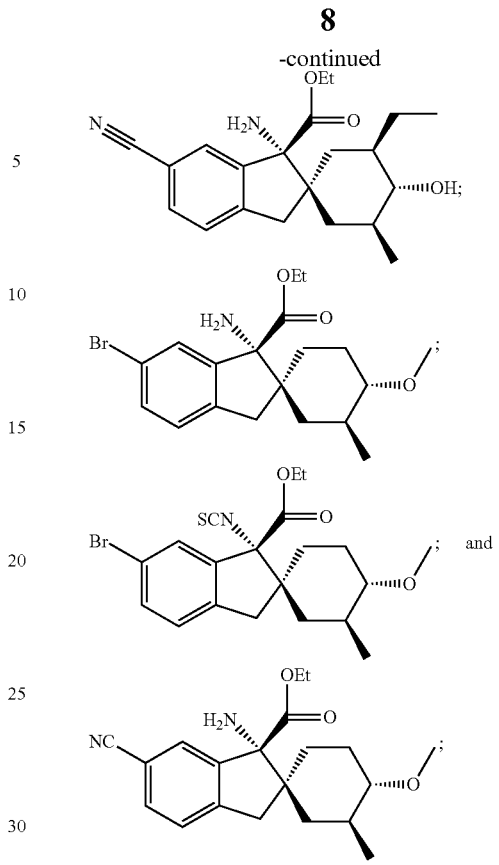

or a salt of any of the foregoing compounds.

DETAILED DESCRIPTION OF THE INVENTION

The compounds of the present invention exhibit potent activity against the BACE1 enzyme and Abeta formation together with high selectivity against the hERG channel, low propensity to cause phospholipidosis, and high metabolic stability. For example, the compounds of the present invention show a BACE1 inhibition with an $IC_{50} < 15$ nM, a hERG inhibition of less than 35% at 10 μM, phospholipidosis with a First Effect Concentration (FEC) of at least 100 μM, and a metabolic stability of less than 25 percent of hepatic blood flow at 1 μM. These combined properties make the compounds of the present invention useful for the treatment of pathological states in humans, in particular, for the treatment of Alzheimer's disease as well as other disorders and diseases mediated by BACE1.

Inhibition of the hERG (human Ether-à-go-go-Related Gene) channel by xenobiotics and subsequent delayed cardiac repolarization is associated with an increased risk for a specific polymorphic ventricular tachyarrhythmia, torsade de pointes, as established by Sanguinetti et al. (1995, Cell, April 21, 81(2):299-307) and a large body of subsequent evidence. To avoid this risk early on, screening against hERG interaction in an in vitro system using heterologous expression of the hERG channel is common practice and an assay of this type is also an important part of later preclinical candidate profiling as recommended by the ICH guideline S7B (International Conference on Harmonization (2005): ICH Topic S 7 B; The nonclinical Evaluation of the Potential for delayed Ventricular Repolarization; (QT Interval Prolongation) by Human Pharmaceuticals (www.ich.org/products/guidelines/safety/article/safety-guidelines.html)). As such, low hERG channel inhibition, such as that shown by the compounds of the present invention, is highly desirable for therapeutics.

Phospholipidosis is a lipid storage disorder in which excess phospholipids accumulate within cells. Drug-induced phospholipidosis is an undesirable drug reaction. Therefore, in order to avoid detrimental side effects, compounds with low phospholipidosis potential are preferred for human therapeutic use.

Metabolic stability refers to the susceptibility of compounds to biotransformation in the context of selecting and/or designing drugs with favorable pharmacokinetic properties. The primary site of metabolism for many drugs is the liver. Intact hepatocytes contain the cytochrome P450s (CYPs), other non-P450 enzymes, and phase II enzymes such as sulfo- and glucuronosyltransferases, and thus represent a prime model system for studying drug metabolization in vitro. Enhanced metabolic stability is associated with several advantages, including increased bioavailability and longer half-life, which can enable lower and less frequent dosing of patients. Thus, enhanced metabolic stability is a favorable characteristic for compounds that are to be used for drugs.

Data provided in Table 1 below show that compounds of the present invention have the combination of potent BACE1 inhibitory activity, selectivity against cardiac hERG, low propensity to cause phospholipidosis, and high metabolic stability. Table 2 provides data showing that certain comparator compounds described in WO2010/105179 do not meet one or more of these criteria.

Terms not specifically defined herein should be given the meanings that would be given to them by one of skill in the art in light of the disclosure and the context. As used in the specification, however, unless specified to the contrary, the following terms have the meaning indicated and the following conventions are adhered to.

When a compound of the present invention is depicted by name or structure without indicating all tautomeric forms, it is to be understood that the compound and its pharmaceutically acceptable salts shall encompass all tautomers.

When a compound of the present invention is depicted by name or structure without indicating the stereochemistry, it is to be understood that the compound and its pharmaceutically acceptable salts shall encompass all stereo, optical and geometrical isomers (e.g., enantiomers, diastereomers, E/Z isomers, etc.) and racemates thereof, as well as mixtures in different proportions of the separate enantiomers, mixtures of diastereomers, or mixtures of any of the foregoing forms.

When a stereo, optical or geometric isomer is depicted by name or structure, it is to be understood that the stereo, optical and/or geometric isomeric purity of the named or depicted stereo, optical or geometric isomer is at least 60%, 70%, 80%, 90%, 99% or 99.9% pure by weight. Stereo, optical and geometric isomeric purity is determined by dividing the weight of the named or depicted stereo, optical and geometric isomer in a mixture by the total weight of all stereo, optical and geometric isomers in the mixture.

When a compound of the present invention or its pharmaceutically acceptable salt is named or depicted by structure, it is to be understood that solvates, hydrates and the anhydrous form of the compound and solvates, hydrates and anhydrous form of its pharmaceutically acceptable salt are included in the invention. "Solvates" refer to crystalline forms wherein solvent molecules are incorporated into the crystal lattice during crystallization. Solvate may include water or nonaqueous solvents such as ethanol, isopropanol, DMSO, acetic acid, ethanolamine, and EtOAc. Solvates, wherein water is the solvent molecule incorporated into the crystal lattice, are typically referred to as "hydrates." Hydrates include stoichiometric hydrates as well as compositions containing variable amounts of water. "Anhydrous form" refers to compounds with no solvent or water or substantially no solvent or water incorporated into the crystal structure (e.g., less than 1:10, 1:20; 1:100; or 1:200 molar ratio of solvent or water to compound).

Salts

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include salts from ammonia, L-arginine, betaine, benethamine, benzathine, calcium hydroxide, choline, deanol, diethanolamine (2,2'-iminobis(ethanol)), diethylamine, 2-(diethylamino)-ethanol, 2-aminoethanol, ethylenediamine, N-ethyl-glucamine, hydrabamine, 1H-imidazole, lysine, magnesium hydroxide, 4-(2-hydroxyethyl)-morpholine, piperazine, potassium hydroxide, 1-(2-hydroxyethyl)-pyrrolidine, sodium hydroxide, triethanolamine (2,2',2"-nitrilotris(ethanol)), tromethamine, zinc hydroxide, acetic acid, 2,2-dichloro-acetic acid, adipic acid, alginic acid, ascorbic acid, L-aspartic acid, benzenesulfonic acid, benzoic acid, 2,5-dihydroxybenzoic acid, 4-acetamido-benzoic acid, (+)-camphoric acid, (+)-camphor-10-sulfonic acid, carbonic acid, cinnamic acid, citric acid, cyclamic acid, decanoic acid, dodecylsulfuric acid, ethane-1,2-disulfonic acid, ethanesulfonic acid, 2-hydroxy-ethanesulfonic acid, ethylenediaminetetraacetic acid, formic acid, fumaric acid, galactaric acid, gentisic acid, D-glucoheptonic acid, D-gluconic acid, D-glucuronic acid, glutamic acid, glutaric acid, 2-oxo-glutaric acid, glycerophosphoric acid, glycine, glycolic acid, hexanoic acid, hippuric acid, hydrobromic acid, hydrochloric acid, isobutyric acid, DL-lactic acid, lactobionic acid, lauric acid, lysine, maleic acid, (−)-L-malic acid, malonic acid, DL-mandelic acid, methanesulfonic acid, galactaric acid, naphthalene-1,5-disulfonic acid, naphthalene-2-sulfonic acid, 1-hydroxy-2-naphthoic acid, nicotinic acid, nitric acid, octanoic acid, oleic acid, orotic acid, oxalic acid, palmitic acid, pamoic acid (embonic acid), phosphoric acid, propionic acid, (−)-L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid and undecylenic acid. Preferred salts are L-mandelic acid and maleic acid. Further pharmaceutically acceptable salts can be formed with cations from metals like aluminium, calcium, lithium, magnesium, potassium, sodium, zinc and the like (see also Pharmaceutical salts, Berge, S. M. et al., J. Pharm. Sci., (1977), 66:1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of acids other than those mentioned above which for example are useful for purifying or isolating the compounds of the present invention (e.g., trifluoro acetate salts) also comprise a part of the invention.

Biological Data

BACE1 Assay (Assay 1)

The inhibitory activity of compounds was assessed by a fluorescence quench assay of BACE1 activity using commercially available substrate HiLyte Fluor™488-Glu-Val-Asn-Leu-Asp-Ala-Glu-Phe-Lys-(QXL™ 520)-OH (SEQ ID NO:1) (AnaSpec, San Jose, Calif.) and truncated human beta-secretase, BACE1 (amino acids 1-454) fused to a myc-his tag and secreted from HEK293/BACE$_{etc.}$ cells into OptiMEM™ (Invitrogen). The substrate was dissolved at 1 mg/ml in DMSO.

The assay was performed in the presence of OptiMEM™ (supernatant collected over 24 h and cleared from cellular debris by centrifugation) containing the ectodomain of BACE1, 25 μl water containing the desired 2-fold concentration of test compound and 2% DMSO, 1 μM substrate peptide, 20 mM NaOAc, pH 4.4, and 0.04% Triton-X100 in a total assay volume of 50 μl in a 384 well plate. In general, 25 μl of compound dilution were added to the plate followed by the addition of 10 μl of BACE1 containing OptiMEM™ diluted 1:10 in water with 0.2% Triton X-100. The reaction was started with the addition of 15 μl substrate in NaOAc buffer. The reaction was incubated at rt (dark) in an Envision® multilabel reader (Perkin Elmer) and the cleavage of the substrate was recorded as kinetic for 60 mM at ex: 485 nm, em: 538 nm. Blank wells containing no enzyme were included on each plate.

The intensity of fluorescence was regressed against time in order to derive velocities of reaction in all 384 wells. These velocities were used for calculating percent control using an uninhibited control containing 1% DMSO as 100% and a blank control performed in the absence of enzyme as 0%. $IC_{50}$ values were calculated by fitting percent control vs. test compound concentration using Assay Explorer®.

hERG-Channel Assay (Assay 2)

Cells: HEK (human embryonic kidney) 293 cells were stably transfected with hERG cDNA.

Pipettes and Solutions:

Cells were superfused with a bath solution containing (mM): NaCl (137), KCl (4.0), $MgCl_2$ (1.0), $CaCl_2$ (1.8), Glucose (10), HEPES (10), pH 7.4 with NaOH. Patch pipettes were made from borosilicate glass tubing using a horizontal puller and filled with pipette solution containing (mM): K-aspartate (130), $MgCl_2$ (5.0), EGTA (5.0), $K_2ATP$ (4.0), HEPES (10.0), pH 7.2 with KOH. Resistance of the microelectrodes was in the range between 2 and 5 MΩ.

Stimulation and Recording:

Membrane currents were recorded using an EPC-10 patch clamp amplifier and PatchMaster software. hERG-mediated membrane currents were recorded at 35° C., using the whole-cell configuration of the patch-clamp technique. Transfected HEK293 cells were clamped at a holding potential of −60 mV and hERG-mediated inactivating tail currents were elicited using a pulse pattern with fixed amplitudes (activation/inactivation: 40 mV for 2000 ms; recovery: −120 mV for 2 ms; ramp to 40 mV in 2 ms; inactivating tail current: 40 mV for 50 ms) repeated at 15 s intervals. During each inter-pulse interval, 4 pulses scaled down by a factor of 0.2 were recorded for a P/n leak subtraction procedure. $R_s$ compensation was employed up to a level that safely allowed recording devoid of ringing.

Compound Preparation and Application:

The different concentrations of the test compounds were applied sequentially on each of the different cells investigated. A steady state level of baseline current was measured for at least 6 sweeps prior to the application of the first test compound concentration.

The test compound was dissolved in DMSO to yield a master stock solution which was diluted further in DMSO to stock solutions needed for the lower concentrations. Final dilutions in extracellular buffer were prepared freshly from these stocks by a 1:1000 dilution step each before starting the experiments.

Data Analysis:

Peak current amplitudes were measured 3 ms after the ramp to +40 mV. For baseline and each concentration, the peak currents of the three last sweeps before application of the next concentration were averaged. Residual currents ($I/I_0$) were calculated for each cell as the fraction of actual average peak current and average baseline peak current.

In Vitro Phospholipidosis Assay (Assay 3)

The phospholipidogenic potential of test compounds was assayed using the human hematopoetic U937 cell line. The test principle was to analyze the phospholipid content by staining the cells with the fluorescent dye Nile red.

U937 cells were seeded into cell culture plates at $0.5 \times 10^6$ cells/mL in RPMI medium containing 10% FBS, 1% DMSO, and 0.005% gentamicin. The cells were cultivated with or without different concentrations of test compound for 48 h under standard culture conditions.

For harvesting, the cells were centrifuged at 130×g for 4 min and washed once with PBS. Then, 2×0.5 mL cell suspensions were prepared for non-fixed cell measurement (0.5 mL for propidium iodide (PI) viability measurement and 0.5 mL for Nile red measurement).

The remaining cells were fixed with 3.7% formaldehyde for 30 min. After a further centrifugation step, cells were resuspended with 1.3 mL Nile red working solution (1 μg/mL) and incubated for 5 min at rt. The cell suspension was washed twice with 3 mL PBS and centrifuged with 130×g for 4 min. The supernatant was discarded and the cells were resuspended with 0.5 mL PBS and kept for flow cytometry measurement.

For Nile red staining of the 0.5 mL non-fixed cell samples, 50 μL of a ready to use Nile red solution (10 μg/mL) were added per sample. Samples were kept on ice for 5 min. Thereafter, they were washed once with 4 mL PBS (4° C., 250×g for 8 min) and finally resuspended in 400 μL PBS and kept for flow cytometry measurement.

For the viability measurement, 12.5 μL of the ready to use PI solution (10 μg/mL) were added to the 0.5 mL non-fixed cell suspension. After 15 min of incubation on ice, the samples were measured by flow cytometry using a Coulter Epics XL/MCL flow cytometer.

The viability of the cells of each sample was determined by flow cytometry measurement of the PI content at channel 2 (568-590 nm). Cut-off gates for the fluorescence-dependent differentiation between live and dead cells were defined based on the analysis of cell culture medium control samples.

Only samples with a cell viability of >=90% relative to control samples were analyzed for phospholipidosis. Each Nile red sample (non-fixed and fixed samples) was measured by flow cytometry at channel 1 (504-541 nm) and channel 4 (660-680 nm).

For each channel, relative Nile red fluorescence intensity of a test sample was calculated compared to control samples and expressed as a percentage of control fluorescence intensity. The assessment of the phospholipidogenic potential and the first effective concentration (FEC) of a test compound was done manually based on the fluorescence intensities at both wavelengths for the fixed cells, as well as for the non-fixed cells.

In Vitro Hepatocyte Stability Assay (Assay 4)

The metabolic degradation of test compounds was assayed in a hepatocyte suspension. Cryopreserved hepatocytes were incubated in an appropriate buffer system (e.g., Dulbecco's modified eagle medium plus 3.5 µg glucagon/500 mL, 2.5 mg insulin/500 mL and 3.75 mg/500 mL hydrocortison) containing 5% species serum. Following a 30 min preincubation in an incubator (37° C., 10% $CO_2$), 5 µl of test compound solution (80 µM; from 2 mM in DMSO stock solution diluted 1:25 with medium) were added into 395 µl hepatocyte suspension (cell density in the range $0.25-5\times10^6$ cells/mL, typically $1\times10^6$ cells/mL; final concentration of test compound final DMSO concentration 0.05%).

The cells were incubated for six h (incubator, orbital shaker) and samples (25 µl) were taken at 0, 0.5, 1, 2, 4 and 6 h. Samples were transferred into acetonitrile and pelleted by centrifugation (5 min). The supernatant was transferred to a new 96 DeepWell™ plate, evaporated under nitrogen and resuspended. Decline of compound was analyzed by HPLC-MS/MS. $CL_{int}$ (in vitro hepatic intrinsic clearance) was calculated as follows:

$$CL_{int}=Dose/AUC=(C_0/CD)/(AUD+C_{last}/k)\times1000/60$$

$C_0$: initial concentration in the incubation [µM];
CD: cell density of vital cells [cells/mL];
AUD: area under the data [µM×h];
$C_{last}$: concentration of last data point [µM];
k: slope of the regression line for compound decline [$h^{-1}$].

The calculated in vitro hepatic intrinsic clearance was scaled up to the intrinsic in vivo hepatic clearance ($CL_{int\,in\,vivo}$) and used to predict hepatic in vivo blood clearance (CL) by the use of a liver model (well-stirred model), as follows:

$$CL_{int,in\,vivo}[mL/min/kg]=(CL_{int}[\mu L/min/10^6\,cells]\times hepatocellularity[10^6\,cells/g\,liver]\times liver\,factor[g/kg\,body\,weight])/1000$$

$$CL[mL/min/kg]=CL_{int,to\,vivo}\times hepatic\,blood\,flow[ml/min/kg]/(CL_{int,in\,vivo}[ml/min/kg]+hepatic\,blood\,flow[mL/min/kg])$$

The in vivo blood clearance was transformed into percent of the hepatic blood flow (% Qh):

$$\%\,Qh=CL[mL/min/kg]/hepatic\,blood\,flow[mL/min/kg])\times100$$

Hepatocellularity, human: $1.2\times10^7$ cells/g liver;
Liver factor, human: 25.7 g/kg body weight;
Hepatic blood flow, human: 21 mL/(min×kg).

Rat Brain Aβ Lowering Assay (Assay 5)

The in vivo efficacy of compounds of the invention was demonstrated in a rat brain Aβ lowering (reduction) assay, and the data are presented in Table 3. Male Sprague-Dawley rats, 5 to 6 weeks of age, were used to demonstrate the ability of compounds of the invention to reduce brain amyloid peptides Aβ1-x. Compounds were administered via oral gavage in 1% Polysorbate-80 and 0.5% Natrosol®, at the single dosages indicated in Table 3. The animals were sacrificed 3 hrs after dosing, and brains were excised, dissected into cerebellum and left and right cerebra and flash-frozen in liquid nitrogen.

The cerebrum was homogenized (5 volumes per weight) in 20 mM Tris-HCL, pH 8.5, 0.2% Triton-X100 supplemented with protease inhibitors (cOmplete, Roche Applied Science) at 4° C. using a glass Dounce homogenizer. The homogenate was centrifuged at 120,000×g for 60 min at 4° C., and the supernatant was collected and analyzed for Aβl-x using immunoassay with chemiluminescent detection (Meso-Scale Discovery, Rockville, Md. (MSD)).

Streptavidin 96-well plates (MSD) were pre-blocked with 5% Blocker A solution (MSD) for 1 hr at rt on an orbital shaker and washed 4 times with phosphate buffered saline (PBS). The wells were pre-coated with 20 ng/well of biotinylated antibody SIG-39155 (Clone M3.2, specific for amino acids 10-15 of the rodent Aβ) for 1 hr at rt and washed 4 times with PBS. For Aβ1-x analysis, 25 µl of either the cleared brain lysates or Aβ1-40 standards (8-500 pg/ml, with 2× increment) were incubated for 1 hr at rt with constant shaking. The wells were washed 4 times with PBS, and 25 µl of the detection antibody (Sulfo-TAG labeled anti-Aβ40 antibody supplied by MSD) was added and incubated for 1 hr at rt. After 4 washes with PBS, 150 µl of the chemiluminescence detection reagent (Read Buffer T, MSD) was added, and the plate was read on an MSD Sector Imager 6000 instrument. The calibration curve was fit into a non-linear four-parameter regression model, and the Aβ1-x concentrations were calculated for each well containing the cleared brain lysates. The percent of Aβ lowering was calculated based on the difference with the average Aβ concentration obtained for the brains from the animals treated with vehicle alone.

Table 1 shows the following properties of the compounds of the present invention: BACE1 inhibitory potency as measured in assay 1, hERG inhibition as measured in assay 2, first effect concentration (FEC) of phospholipidosis as measured in assay 3, and metabolic stability as measured in assay 4.

TABLE 1

| Example # | BACE1 $IC_{50}$ nM (assay 1) | % Inhibition hERG @ 10 µM (assay 2) | Phospholipidosis FEC $IC_{50}$ µM (assay 3) | In vitro Human Hepatocytes % Qh @ 1 µM (assay 4) |
|---|---|---|---|---|
| 1 | 14.6 | 13 | 400 | 0 |
| 2 | 10.3 | 4.5 | 400 | 1.6 |
| 3 | 3.0 | 20 | 200 | 3.1 |
| 4 | 2.7 | 13 | 800 | 6.1 |
| 5 | 2.6 | 12 | 400 | 6.1 |
| 6 | 6.3 | 1.8 | 400 | 11 |
| 7 | 3.4 | 15 | 400 | 13 |
| 8 | 1.9 | 6 | 800 | 19.1 |
| 9 | 10.7 | 2.5 | 400 | 12.4 |
| 10 | 10.6 | 33 | >100 | 0 |
| 11 | 14.6 | 19 | 200 | 0 |
| 12 | 6.8 | 15 | 100 | 0 |
| 13 | 8.7 | 12 | 200 | 4.2 |
| 14 | 4.5 | 27 | 200 | 5.2 |
| 15 | 9.7 | 15.2 | 800 | 22.9 |
| 16 | 9.4 | 1.4 | 200 | 19 |

Table 2 provides data showing that compounds of the present invention have at least one of the following properties relative to certain comparator compounds described in WO2010/105179: 1) significantly lower $IC_{50}$ inhibitory values in a BACE1 enzymatic assay, significantly lower percent inhibition of hERG, significantly lower propensity to cause phospholipidosis, and significantly greater metabolic stability relative.

TABLE 2
| Example # | BACE1 IC50 nM (Assay 1) | % Inhibition hERG @ 10 μM (Assay 2) | Phospholipidosis FEC IC50 μM (Assay 3) | In vitro Human Hepatocytes % Qh @ 1 μM (Assay 4) |
|---|---|---|---|---|
| Comparison 1 | | | | |
| 1 | 14.6 | 13 | 400 | 0 |
| 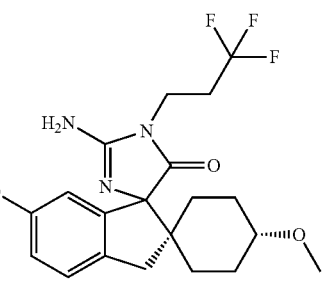<br>428 in WO2010/105179 | 8.3 | 87 | — | — |
| 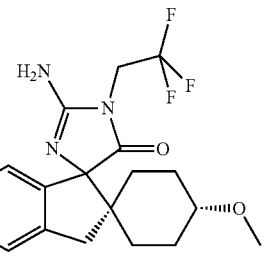<br>512 in WO2010/105179 | 3.5 | 89 | — | 88 |
| Comparison 2 | | | | |
| 10 | 10.6 | 33 | >100 | 0 |
| 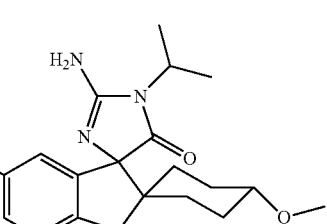<br>121 in WO2010/105179 | 107 | — | — | — |
| 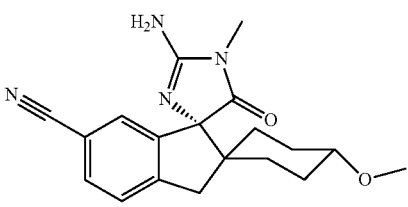<br>174 in WO2010/105179 | 16 | 90 | 400 | 14 |

TABLE 2-continued
| Example # | BACE1 IC50 nM (Assay 1) | % Inhibition hERG @ 10 μM (Assay 2) | Phospholipidosis FEC IC50 μM (Assay 3) | In vitro Human Hepatocytes % Qh @ 1 μM (Assay 4) |
|---|---|---|---|---|
| Comparison 3 | | | | |
| 3 | 3.0 | 20 | 200 | 3.1 |
| | 256 | — | — | — |
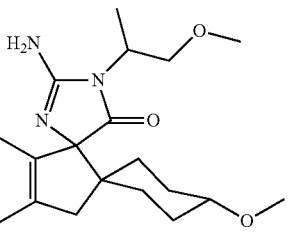
251 in WO2010/105179
| Comparison 4 | | | | |
|---|---|---|---|---|
| 12 | 6.8 | 15 | 100 | 0 |
| | 1.1 | 60 | 25 | 36 |
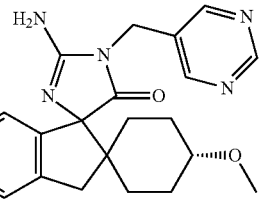
255 in WO2010/105179
| | 5.1 | 60 | — | 8.5 |
|---|---|---|---|---|
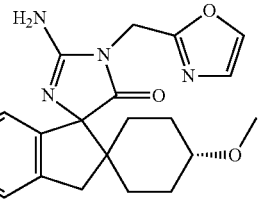
249 in WO2010/105179
| Comparison 5 | | | | |
|---|---|---|---|---|
| 2 | 10.3 | 4.5 | 400 | 1.6 |
| | 7.3 | 36 | 50 | 43 |
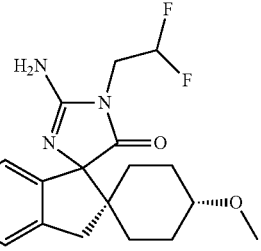
602 in WO2010/105179

TABLE 2-continued
| Example # | BACE1 IC50 nM (Assay 1) | % Inhibition hERG @ 10 μM (Assay 2) | Phospholipidosis FEC IC50 μM (Assay 3) | In vitro Human Hepatocytes % Qh @ 1 μM (Assay 4) |
|---|---|---|---|---|
| 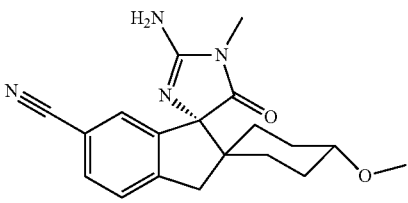 174 in WO2010/105179 | 16 | 90 | 400 | 14 |
| Comparison 6 | | | | |
| 11 | 14.6 | 19 | 200 | 0 |
| 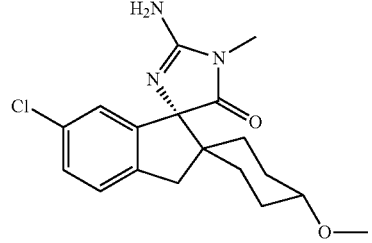 172 in WO2010/105179 | 19 | 58 | 100 | — |
| 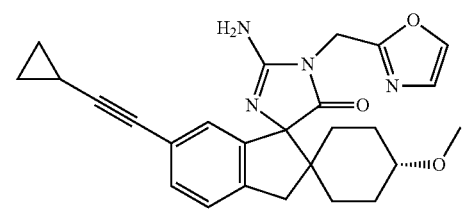 249 in WO2010/105179 | 5.1 | 60 | — | 8.5 |
| Comparison 7 | | | | |
| 8 | 1.9 | 6 | 800 | 19.1 |
| 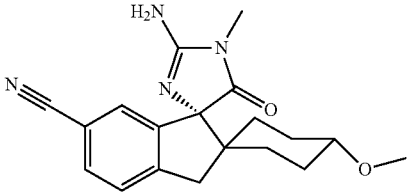 174 in WO2010/105179 | 16 | 90 | 400 | 14 |
| 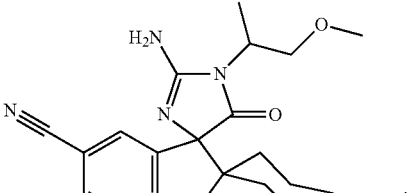 251 in WO2010/105179 | 256 | — | — | — |

The ability of compounds of the invention to reduce brain Aβ was demonstrated in rats, as described in Assay 5, and the in vivo efficacy data are presented in Table 3.

TABLE 3

| Example | Dose (mg/kg) | % Aβ Reduction |
|---|---|---|
| 1 | 25 | 25 |
| 2 | 12.5 | 40 |
| 4 | 12.5 | 21 |
| 7 | 25 | 58 |
| 9 | 25 | 42 |

Method of Treatment

The present invention is directed to compounds which are useful in the treatment of disorders or diseases characterized by elevated β-amyloid deposits or β-amyloid levels in a subject wherein the inhibition of the activity of the β-secretase enzyme (BACE1) is of therapeutic benefit, including but not limited to the treatment, amelioration or prevention of neurodegenerative disorders, disorders characterized by cognitive decline, cognitive impairment, dementia and diseases characterized by production of β-amyloid deposits and/or neurofibrillary tangles.

Compounds of the present invention are useful for treatment of Alzheimer's disease, Trisomy 21 (Down Syndrome), Hereditary Cerebral Hemorrhage with Amyloidosis of the Dutch-type (HCHWA-D), senile dementia, cerebral amyloid angiopathy, degenerative dementia, dementias of mixed vascular and degenerative origin, dementia associated with Parkinson's disease, dementia associated with progressive supranuclear palsy, dementia associated with cortical basal degeneration, diffuse Lewy body type of Alzheimer's disease, dry age related macular degeneration (AMD), and glaucoma. The "dry" form of AMD, also known as "central geographic atrophy", results from atrophy to the retinal pigment epithelial layer below the neurosensory retina, which causes vision loss through loss of photoreceptors (rods and cones) in the central part of the eye. No medical or surgical treatment is currently available for this condition. Treatments available so far (e.g., suggested by the National Eye Institute) include the use of vitamin supplements with high doses of antioxidants, lutein and zeaxanthin, which may slow the progression of dry macular degeneration. Glaucoma is a disease where fluid pressure inside the eye increases, causing irreversible damage to the optic nerve and loss of vision. Abeta colocalizes with apoptotic retinal ganglion cells in experimental glaucoma and induces significant retinal ganglion cell apoptosis in a dose- and time-dependent manner.

Accordingly, the present invention relates to a compound or a pharmaceutically acceptable salt thereof as a medicament.

Furthermore, the present invention relates to the use of a compound in the treatment of a disease and/or condition wherein the inhibition of the activity of the β-secretase enzyme (BACE1) is of therapeutic benefit.

Furthermore, the present invention relates to the use of a compound in the treatment of neurodegenerative disorders, disorders characterized by cognitive decline, cognitive impairment, dementia and diseases characterized by production of β-amyloid deposits or neurofibrillary tangles.

Therefore, the present invention relates to the use of a compound of the present invention in the treatment of Alzheimer's disease, Trisomy 21 (Down Syndrome), Hereditary Cerebral Hemorrhage with Amyloidosis of the Dutch-type (HCHWA-D), senile dementia, cerebral amyloid angiopathy, degenerative dementia, dementias of mixed vascular and degenerative origin, dementia associated with Parkinson's disease, dementia associated with progressive supranuclear palsy, dementia associated with cortical basal degeneration, diffuse Lewy body type of Alzheimer's disease, dry AMD, and glaucoma.

The present invention also provides a method for the treatment of a disorder related to or associated with excessive BACE1 activity in a patient in need thereof which comprises administering to said patient an effective amount of a disclosed compound or a pharmaceutically acceptable salt thereof. The present invention also provides methods for inhibiting the activity of BACE1 in a subject in need thereof, comprising administering to a subject and/or contacting a receptor thereof with an effective amount of at least one disclosed compound or a pharmaceutically acceptable salt thereof. The present invention also provides methods of ameliorating β-amyloid deposits in a subject in need thereof, comprising administering to said subject an effective amount of at least one disclosed compound or a pharmaceutically acceptable salt thereof.

The invention includes a therapeutic method for treating or ameliorating an BACE1 mediated disorder in a subject in need thereof comprising administering to a subject in need thereof an effective amount of a compound of the invention described herein, or pharmaceutically acceptable salts thereof or composition thereof.

As used herein, the term "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

As used herein, the term "treating" or 'treatment" refers to obtaining desired pharmacological and/or physiological effect. The effect can be prophylactic (i.e., reducing the likelihood of developing the disorder or disease) or therapeutic, which includes achieving, partially or substantially, one or more of the following results: partially or totally reducing the extent of the disease, disorder or syndrome; ameliorating or improving a clinical symptom or indicator associated with the disorder; or delaying, inhibiting or decreasing the likelihood of the progression of the disease, disorder or syndrome.

The dose range of the compounds according to the present invention applicable per day is usually from 0.1 to 3000 mg, preferably from 1 to 2000 mg, more preferably from 10 to 1000 mg, most preferably, 50 or 500 mg. Each dosage unit may conveniently contain from 0.1 to 1000 mg, preferably 25 to 250 mg.

The actual pharmaceutically effective amount or therapeutic dosage will of course depend on factors known by those skilled in the art such as age and weight of the patient, route of administration and severity of disease. In any case the combination will be administered at dosages and in a manner which allows a pharmaceutically effective amount to be delivered based upon patient's unique condition.

Pharmaceutical Compositions

Suitable preparations for administering the compounds of the present invention will be apparent to those with ordinary skill in the art and include for example tablets, pills, capsules, suppositories, lozenges, troches, solutions, syrups, elixirs, sachets, injectables, inhalatives and powders, etc. The content of the pharmaceutically active compound(s) should be in the range from 0.1 to 95 wt.-%, preferably 5 to 90 wt.-% of the composition as a whole.

Suitable tablets may be obtained, for example, by mixing one or more compounds of the invention with known excipients, for example inert diluents, carriers, disintegrants, adjuvants, surfactants, binders and/or lubricants. The tablets may also consist of several layers.

Combination Therapy

In one embodiment, the present invention includes combination therapy for treating or ameliorating a disease or a disorder described herein. The combination therapy comprises administering a combination of at least one compound of the present invention with one or more agent selected from the group of, for example, gamma-secretase inhibitors or modulators; amyloid aggregation inhibitors blocking the formation of Abeta oligomers or Abeta fibrils (e.g., ELND-005); directly or indirectly acting neuroprotective and/or disease-modifying substances; anti-oxidants (e.g., vitamin E or ginkolide); anti-inflammatory substances (e.g., Cox inhibitors, NSAIDs additionally or exclusively having Abeta lowering properties); HMG-CoA reductase inhibitors (statins); acetylcholinesterase inhibitors (e.g., donepezil, rivastigmine, tacrine, and galantamine); NMDA receptor antagonists (e.g., memantine); AMPA receptor agonists; AMPA receptor positive modulators, AMPAkines, monoamine receptor reuptake inhibitors, substances modulating the concentration or release of neurotransmitters; substances inducing the secretion of growth hormone (e.g., ibutamoren mesylate and capromorelin); CB-1 receptor antagonists or inverse agonists; antibiotics (e.g., minocyclin or rifampicin); PDE2, PDE4, PDE5, PDE9, PDE10 inhibitors, GABAA receptor inverse agonists, GABAA receptor antagonists, nicotinic receptor agonists or partial agonists or positive modulators, alpha4beta2 nicotinic receptor agonists or partial agonists or positive modulators, alpha7 nicotinic receptor agonists or partial agonists or positive modulators; histamine H3 antagonists, 5 HT-4 agonists or partial agonists, 5HT-6 antagonists, alpha2-adrenoreceptor antagonists, calcium antagonists, muscarinic receptor M1 agonists or partial agonists or positive modulators, muscarinic receptor M2 antagonists, muscarinic receptor M4 antagonists, metabotropic glutamate-receptor 5 positive modulators, antidepressants, such as citalopram, fluoxetine, paroxetine, sertraline and trazodone; anxiolytics, such as lorazepam and oxazepam; antiphychotics, such as aripiprazole, clozapine, haloperidol, olanzapine, quetiapine, risperidone and ziprasidone, and other substances that modulate receptors or enzymes in a manner such that the efficacy and/or safety of the compounds according to the invention is increased and/or unwanted side effects are reduced. The compounds according to the invention may also be used in combination with immunotherapies (e.g., active immunization with Abeta or parts thereof or passive immunization with humanized anti-Abeta antibodies or nanobodies) for the treatment of the above-mentioned diseases and conditions.

Combination therapy includes co-administration of the compound of the invention with one or more other agent, sequential administration of the compound and one or more other agent, administration of a composition containing a compound and one or more other agent, or simultaneous administration of separate compositions containing the compound and one or more other agent.

EXPERIMENTAL SECTION

Methods of Preparation of Compounds

Compounds of the invention can be prepared employing conventional methods that utilize readily available reagents and starting materials. The reagents used in the preparation of the intermediates of this invention can be either commercially obtained or can be prepared by standard procedures described in the literature.

Microwave reactions were carried out in CEM reactor using discovery SP system or in Biotage, Initiator 60 EXP. Where NMR data are presented, spectra were obtained in Varian −400 (400 MHz). Spectra are reported as ppm downfield from tetramethylsilane with number of proton, multiplicities and, in certain instances, coupling constants indicated parenthetically along with reference to deuterated solvent. Compounds were purified by basic preparative HPLC method as described below.

Method 1:
Mobile phase A: water with 0.05% $NH_4OH$; Mobile phase B: ACN; Flow rate: 25 mL/min; Detection: UV 220 nm/254 nm; Column: Phenomenex Gemini C18 250*30 mm*5um; Column temperature: 30° C.

| Time in min | % A | % B |
|---|---|---|
| 0.0 | 68 | 32 |
| 12.00 | 38 | 62 |
| 12.20 | 0 | 100 |
| 13.5 | 0 | 100 |
| 13.7 | 90 | 10 |

Method 2:
Mobile phase A: water with 0.05% $NH_4OH$; Mobile phase B: ACN; Flow rate: 25 mL/min; Detection: UV 220 nm/254 nm; Column: Durashell C18 250*30 mm*5um; Column temperature: 30° C.

| Time in min | % A | % B |
|---|---|---|
| 0.0 | 67 | 33 |
| 12.00 | 47 | 53 |
| 12.20 | 0 | 100 |
| 13.5 | 0 | 100 |
| 13.7 | 90 | 10 |

LC-MS data were obtained by utilizing the following chromatographic conditions:

Method 1:
HPLC System: Waters ACQUITY; Column: Waters ACQUITY CSH™ C18 1.7 μM.
Guard column: Waters Assy. Frit, 0.2 μM, 2.1 mm; Column tem: 40° C.
Mobile Phase: A: TFA:Water (1:1000, v:v) Mobile phase B:TFA:ACN (1:1000, v:v); Flow Rate: 0.65 mL/min; Injection Volume: 2 μL; Acquisition time: approximately 1.5 minute.
Gradient Program:

| Time (min) | B % |
|---|---|
| 0 | 10 |
| 0.8 | 90 |
| 1.20 | 90 |
| 1.21 | 10 |

Mass Spectrometer Parameters
Mass Spectrometer: Waters SQD; Ionization: Positive Electrospray Ionization (ESI); Mode Scan (100-1400 m/z in every 0.2 second); ES Capillary Voltage: 3.5 kV; ES Cone Voltage: 25 v.

Source Temperature: 120° C.; Disolvation Temperature: 500° C.; Desolvation Gas Flow: Nitrogen Setting 650 (L/h); Cone Gas Flow: Nitrogen Setting 50 (L/h).
Method 2:
HPLC System: Waters Alliance with DA- and MS-Detector; Column: Waters XBridge C18 4.6×30 mm, 3.5 µm; Column temp: 60° C.
Mobile Phase: A: TFA:Water (1:1000, v:v) Mobile phase B: MeOH; Flow Rate: 4 mL/min
Gradient Program:

| Time (min) | B % |
|---|---|
| 0 | 5 |
| 1.6 | 100 |
| 1.85 | 100 |
| 1.9 | 5 |

Method 3:
HPLC System: Waters Alliance with DA- and MS-Detector; Column: Waters XBridge C18 4.6×30 mm, 3.5 µm; Column temp: 60° C.
Mobile Phase: A: TFA:Water (1:1000, v:v) Mobile phase B: ACN; Flow Rate: 5 mL/min
Gradient Program:

| Time (min) | B % |
|---|---|
| 0 | 3 |
| 0.2 | 3 |
| 1.6 | 100 |
| 1.7 | 100 |

Method 4:
HPLC System: Waters Alliance with DA- and MS-Detector; Column: Waters XBridge C18 4.6×30 mm, 3.5 µm; Column temp: 60° C.
Mobile Phase: A: TFA:Water (1:1000, v:v) Mobile phase B: MeOH; Flow Rate: 4 mL/min
Gradient Program:

| Time (min) | B % |
|---|---|
| 0 | 5 |
| 0.2 | 5 |
| 1.5 | 100 |
| 1.75 | 100 |
| 1.85 | 5 |

SFC separation and characterization of compounds were carried out under the following methods:
Method A:
Instrument: Thar SFC 80; Column: AD 250 mm*30 mm, 5um; Mobile phase: A: Supercritical $CO_2$, B: IPA (0.05% DEA), A: B=80:20 at 60 ml/min; Column Temp: 38° C.; Nozzle Pressure: 100 Bar; Nozzle Temp: 60° C.; Evaporator Temp: 20° C.; Trimmer Temp: 25° C.; Wavelength: 220 nm.
Method B:
Instrument: SFC MG2; Column: OJ 250 mm*30 mm, 5 um; Mobile phase: A: Supercritical $CO_2$, B: MeOH (0.05% DEA), A:B=90:10 at 70 ml/min; Column Temp: 38° C.; Nozzle Pressure: 100 Bar Nozzle Temp: 60° C.; Evaporator Temp: 20° C.; Trimmer Temp: 25° C.; Wavelength: 220 nm.
The invention is illustrated by way of the following examples, in which the following abbreviations may be employed:

| Abbreviation | Meaning |
|---|---|
| ACN | acetonitrile |
| Boc | tert-butoxy carbonyl or t-butoxy carbonyl |
| $Boc_2O$ | di-tert-butyl-dicarbnate |
| brine | saturated aqueous NaCl |
| DAST | (diethylamino) sulfur trifluoride |
| DCM | methylene chloride |
| DIEA | diisopropyl ethyl amine |
| DMA | dimethyl acetamide |
| DMF | dimethyl formamide |
| DMSO | dimethyl sulfoxide |
| Et | ethyl |
| dppf | 1,1-bis(diphenylphosphino)ferrocene |
| EDCI | 1-(3-dimethylaminopropyl)-3-ethylcarbodiiimide hydrochloride |
| EtI | ethyl iodide |
| $Et_3N$ | triethylamine |
| $Et_2O$ | ethyl ether |
| EtOAc | ethyl acetate |
| EtOH | ethanol |
| h | hour(s) |
| HPLC | high performance liquid chromatography |
| LDA | lithium diisopropylamide |
| min | minute |
| MeOH | methanol |
| MeI | methyl iodide |
| Me | methyl |
| $Me_2S$ | dimethyl sulfide |
| MsCl | methane sulfonyl chloride |
| mL | milliliters |
| mmol | millimoles |
| mg | milligram |
| NaOMe | sodium methoxide |
| NCS | N-chlorosuccinamide |
| $PdCl_2dppf$ | [1,1-bis(diphenylphosphino)ferrocene] dichloropalladium(II) |
| $Pd2(dba)_3$ | tris(dibenzylideneacetone)dipalladium(0) |
| PE | petroleum ether |
| rt | room temperature |
| sat. | saturated |
| SFC | super critical fluid chromatography |
| t-BuOK | potassium tert butoxide |
| t-BuLi | tert butyl lithium |
| $t-BuNH_2$—$BH3$ | tert butylamin-borane complex |
| t-BuOOH | tert butyl peroxide |
| TEA | triethylamine |
| TFA | trifluoroacetic acid |
| TFAA | trifluoroacetic acid anhydride |
| THF | tetrahydrofuran |
| $Ti(OEt)_4$ | titanium tetra ethoxide |
| TLC | thin layer chromatography |
| TMSI | trimethylsilyl iodide |
| v | volume |
| XPhos | dicyclohexylphosphino-2',4',6'-triiso-propyl-1,1'-biphenyl |
| $Zn(CN)_2$ | zinc cyanide |

Example 1

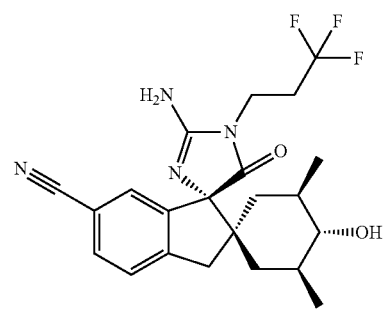 [SMILES: C[C@@H]1C[C@@]2(Cc3ccc(C#N)cc3[C@]23N=C(N)N(CCC(F)(F)F)C3=O)C[C@H](C)[C@H]1O]

Step 1: Synthesis of Intermediate 3

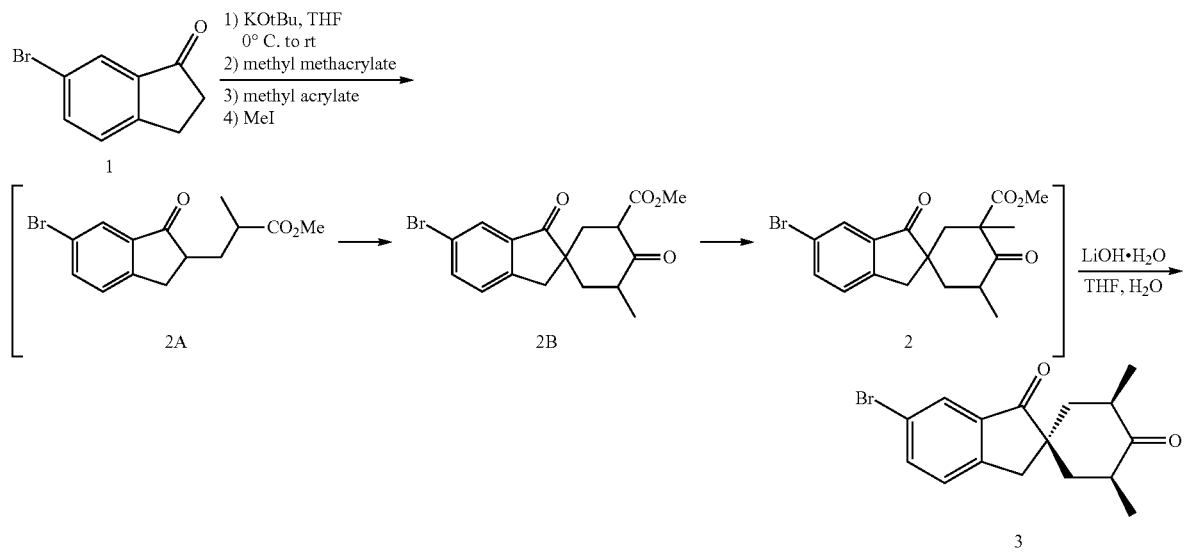

To a mixture of 6-bromo-indan-1-one (100.00 g, 473.8 mmol) in anhydrous THF (1 L) at 0° C. was added t-BuOK (58.5 g, 521.2 mmol). After 5 minutes, the mixture was warmed to rt and was stirred for another 10 min before methyl methacrylate (49.8 g, 53.2 mL, 497.5 mmol, 1.05 eq) was added in one portion. After 2 h, methyl acrylate (49.0 g, 51.2 mL, 568.6 mmol, 1.2 eq) was added to the reaction mixture. After 3 h of stirring at rt, MeI (101 g, 44.3 mL, 710.7 mmol, 1.5 eq) was added to the reaction mixture, and the mixture was further stirred for 16 h. H$_2$O (1 L) was added followed by LiOH*H$_2$O (79.5 g, 1895 mmol, 4.0 eq). The mixture was stirred for 28 h at rt. THF was removed under reduced pressure. The residue was diluted with H$_2$O (1 L), filtered, and washed with H$_2$O until the filtrate was neutral. The product was washed with MeOH to afford 50 g of intermediate 3.

Step 2: Synthesis of Intermediate 4

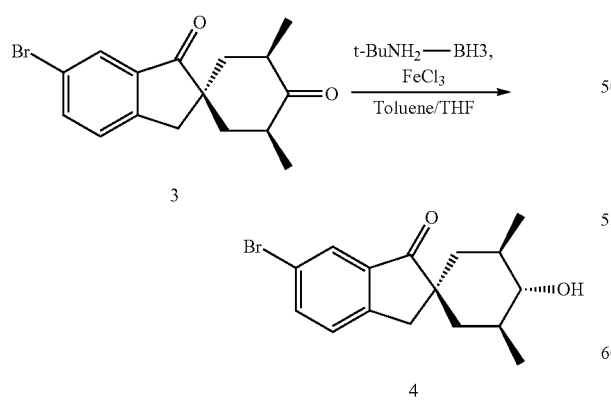

A mixture of FeCl$_3$ (6.0 g, 37.0 mmol) and toluene (60 mL) was cooled to 0° C. A mixture of intermediate 3 (11.9 g, 37.0 mmol) in THF (48 mL) was added to the mixture. The mixture was stirred for 5 min at 0° C. and then cooled to −10° C. A solution of t-BuNH$_2$—BH$_3$ (3.5 g, 40.7 mmol) in THF (12 mL) was added dropwise to the reaction mixture at −10° C. The reaction mixture was stirred at about −10° C. for 30 min, quenched with aqueous HCl solution (6N, 10 mL), stirred at about 0° C. for 30 min, and then allowed to warm to rt. The mixture was concentrated to remove THF, and toluene (60 mL) was added. The aqueous layer was removed, and the organic phase was washed with water (3×60 mL). The organic phase was concentrated to half volume, heated to 50° C. to obtain a solution, and then cooled to 0° C. over 1 h and held at 0° C. for 1 h. The solid was filtered and washed with cold (0° C.) toluene (12 mL), and dried under vacuum to give compound 4 (9.93 g).

LC-MS (method 1): tR=1.24 min, MS (ESI) m/z 323.1 [M+H]$^+$.

$^1$H NMR (CDCl$_3$): δ: 7.889-7.894 (s, 1H), 7.671-7.696 (d, 1H), 7.311-7.332 (d, 1H), 3.605 (s, 1H), 2.981 (s, 2H), 1.769-1.797 (m, 4H), 1.072-1.082 (m, 2H), 1.019-1.056 (m, 6H).

Step 3: Synthesis of Intermediate 5

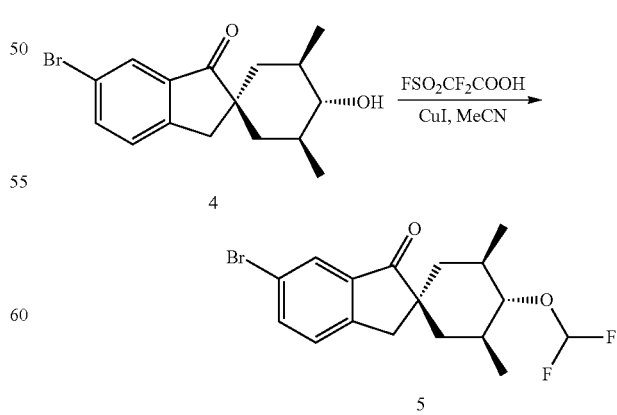

A mixture of intermediate 4 (6.0 g, 18.6 mmol) and CuI (0.71 g, 3.72 mmol, 0.2 eq) in ACN (120 mL) was heated to 60° C. and 2-(fluorosulfonyl)difluotoacetic acid (13.2 g, 74.4 mmol) was added. The mixture was stirred at 60° C. for 20 min. The mixture was cooled, quenched with H₂O and extracted with EtOAc. The combined organic phases were washed with H₂O and brine, dried over anhydrous Na₂SO₄, concentrated to afford 15 g crude product, which was purified by column on slica gel (eluent: petroleum ether: ethyl acetate from 300:1 to 50:1) to afford intermediate 5 (4.6 g).

Step 4: Synthesis of Intermediate 6

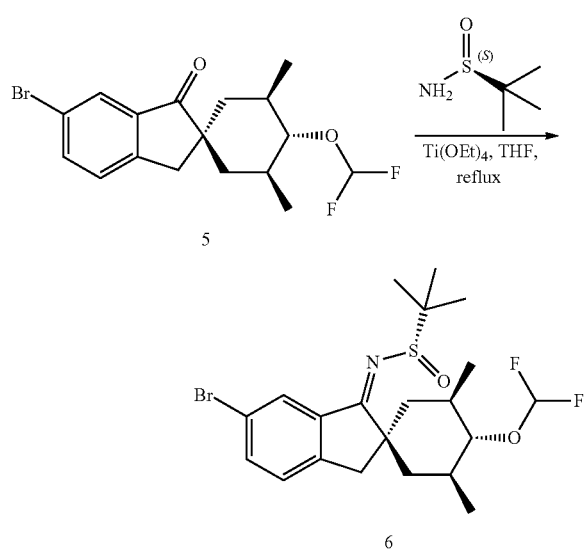

The mixture of intermediate 5 (3.4 g, 9.2 mmol) and titanium (IV) ethoxide (21 g, 92 mmol) in dry THF (40 mL) was stirred at rt for 1 h. (S)—N-tert-butylsulfinamide (4.5 g, 36.8 mmol) was added and the resulting mixture was stirred at 80° C. under N₂ atmosphere for 12 h. The reaction mixture was cooled and water (400 mL) was added. The mixture was filtered and the aqueous layer was extracted with ethyl acetate (3×400 mL). The separated organic phase was dried over Na₂SO₄ and concentrated under reduced pressure. The residue was purified by column chromatography on silica gel (petroleum ether: ethyl acetate=20:1) to yield intermediate 6 (3.9 g).

Step 5: Synthesis of Intermediate 7

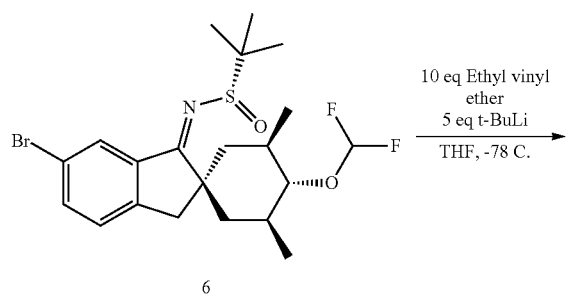

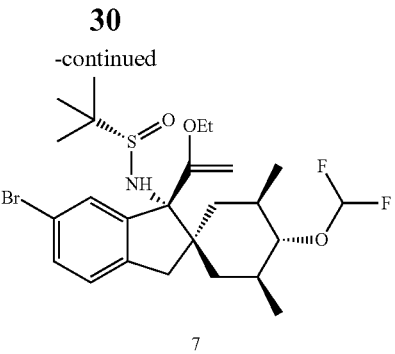

A t-BuLi solution (32 mL, 41.0 mmol, 1.3 M in hexane) was added dropwise to a solution of ethyl vinyl ether (7.05 g, 82 mmol) in anhydrous THF (50 mL) at −78° C. under N₂ atmosphere and the mixture was stirred for 20 min. The resulting mixture was stirred at 0° C. for another 45 min and then cooled to −78° C. A pre-cooled solution at −78° C., containing intermediate 6 (3.9 g, 8.2 mmol) in anhydrous THF (80 mL) was added dropwise and the mixture was stirred for 2 h at −78° C. The reaction was quenched with sat. NH₄Cl (50 mL) aqueous solution and extracted with ethyl acetate (3×300 mL). The organic phases were combined and concentrated under reduced pressure. The crude product was purified by preparative HPLC (method 2) to afford intermediate 7 (3.3 g).

Step 6: Synthesis of Intermediate 8

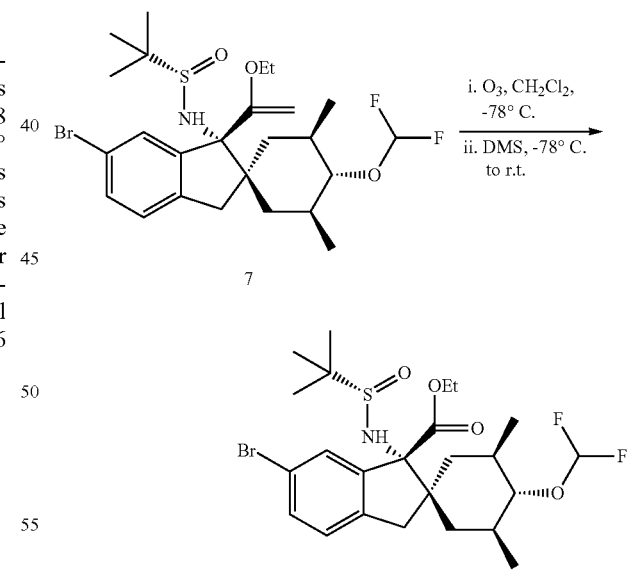

Intermediate 7 (10 g, 18.2 mmol) was added to a solution of MeOH in DCM (5:1, 100 mL) and cooled to −78° C. Ozone was bubbled through the mixture for 20 min. After 10 minutes of additional stirring, the mixture was purged with N₂ for 15 minutes and then treated with Me₂S (20 mL) at −78° C. It was allowed to warm to rt and stirred for 3 h at rt. The solvent was removed under reduced pressure and the residue was purified by column chromatography on silica gel (petroleum ether: ethyl acetate=20:1 to 5:1) to yield intermediate 8 (6 g).

Step 7: Synthesis of Intermediate 9

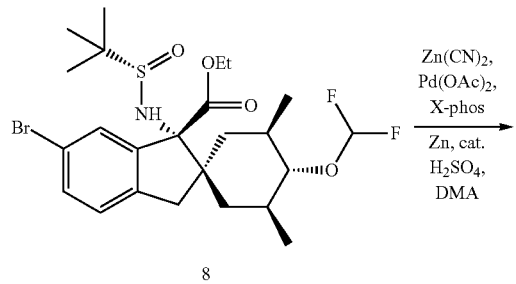

8

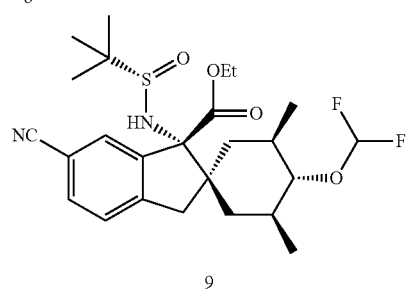

9

Concentrated sulfuric acid (48 µL) was added to DMA (20 mL) and the solvent was purged with $N_2$ for 20 min. A 50 mL round bottom flask was charged with $Pd(OAc)_2$ (0.3 g) and Xphos (1.25 g) under $N_2$, then the above solvent was transferred in. The resulting mixture was heated at 80° C. for 30 min to give mixture A.

In an another flask, DMA (50 mL) was purged with $N_2$ and intermediate 8 (2.2 g, 4.0 mmol), $Zn(CN)_2$ (0.5 g, 4.0 mmol) and zinc dust (14.1 mg) were added. The mixture A was added to this solution, and the resulting mixture was heated at 90° C. for 1 h. The reaction mixture was cooled to rt, diluted with water (100 mL) and ethyl acetate (100 mL) and stirred for 10 minutes. The mixture was filtered through celite, and the organic layer was separated. The aqueous layer was extracted with ethyl acetate (2×30 mL). The combined organic layer was washed with water, brine and dried and the solvent was removed under reduced pressure. The residue was purified on flash column on silica gel (petroleum ether: ethyl acetate; 20:1 to 3:1) to yield intermediate 9 (1.5 g).

Step 8: Synthesis of Intermediate 10

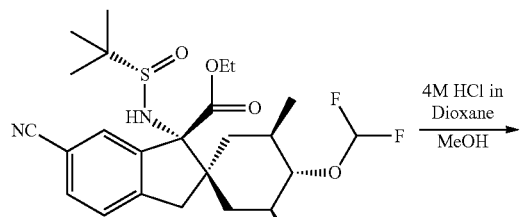

9

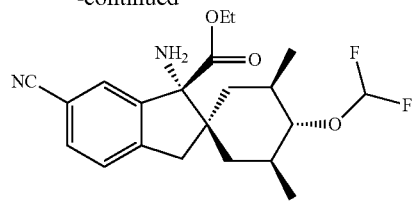

10

To a mixture of intermediate 9 (0.5 g, 1.01 mmol) in MeOH (11 mL) was added HCl in dioxane (4 M, 2.25 mL). The resulting mixture was stirred for 1 h. The solvent was removed under reduced pressure to afford crude intermediate 10 (529 mg) which was used for the next step without further purification.

Step 9: Synthesis of Intermediate 11

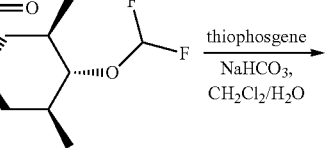

10

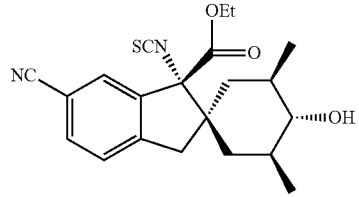

11

To a solution of intermediate 10 (529 mg, 1.35 mmol) in DCM (6 mL), $H_2O$ (6 mL) and $NaHCO_3$ (1.13 g, 13.5 mmol) were added at rt. Thiophosgene (310 mg, 2.7 mmol) was added with vigorous stirring and the mixture was stirred for 1 h. The organic layer was separated and the aqueous layer was extracted with DCM (3×40 mL). The organic layers were combined and washed with brine (2×40 mL), dried and the solvent was removed under reduced pressure to afford crude intermediate 11 (520 mg), which was used for the next step without further purification.

Step 10: Synthesis of Intermediate 12

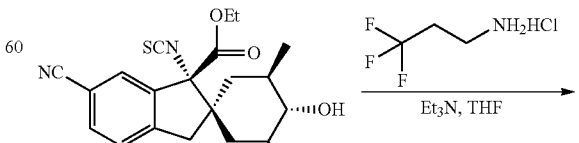

11

-continued

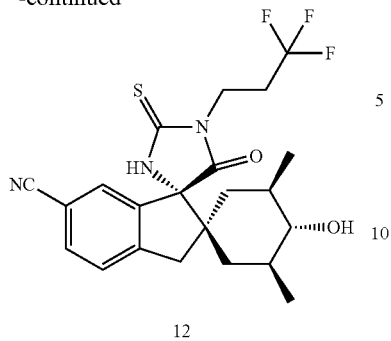

12

To a mixture of intermediate 11 (200 mg, 0.52 mmol) in THF (10 mL) was added 3,3,3-trifluoro-propylamine hydrochloride (156 mg, 1.04 mmol) and TEA (526 mg, 5.2 mmol). The mixture was stirred overnight at rt. The reaction was diluted with water and extracted with EtOAc (30 mL). The organic layers were combined, washed with brine (10 mL), dried over Na$_2$SO$_4$, filtered and concentrated under reduced pressure to afford crude product. The residue was purified by preparative TLC (petroleum ether: ethyl acetate; 1:1) to afford intermediate 12 (265 mg).

Step 11: Synthesis of Example 1

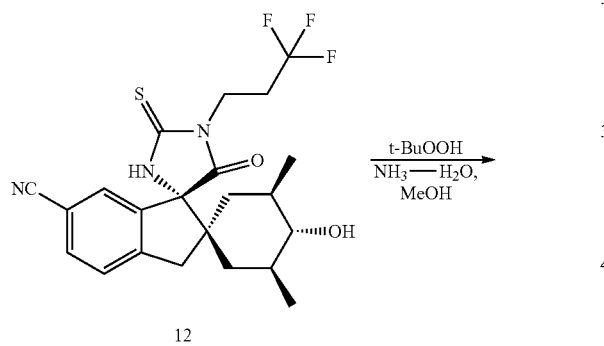

To a mixture of intermediate 12 (265 mg, 0.59 mmol) in MeOH (10 ml), aqueous ammonium hydroxide (1.5 mL) and t-BuO$_2$H (0.8 mL, 5.0 M solution in nonane) were added. The mixture was stirred at rt for 16 h and then quenched with sat. aqueous Na$_2$S$_2$O$_3$ solution (0.5 mL). The residue was partitioned between EtOAc (20 mL) and H$_2$O (10 mL). The organic layer was separated and washed with brine (10 mL), dried over Na$_2$SO$_4$, filtered and concentrated under reduced pressure. The residue was purified by preparative HPLC (method 2) to give Example 1 (86.9 mg).

LC-MS (method 1): tR=0.92 min, MS (ESI) m/z 435.2 [M+H]$^+$.
$^1$H-NMR (CD$_3$OD): δ 7.65 (d, J=7.6 Hz, 1H), 7.49 (d, J=7.6 Hz, 1H), 7.30 (s, 1H), 3.82-3.85 (t, J=7.6 Hz, 2H), 3.24 (s, 1H), 3.15 (d, J=16.0 Hz, 1H), 2.56 (m, 3H), 1.23-1.79 (m, 5H), 0.956-1.02 (m, 7H).
$^{19}$F NMR: δ-66.64.

Synthesis of Intermediate 20

Step 1: Synthesis of Intermediate 13

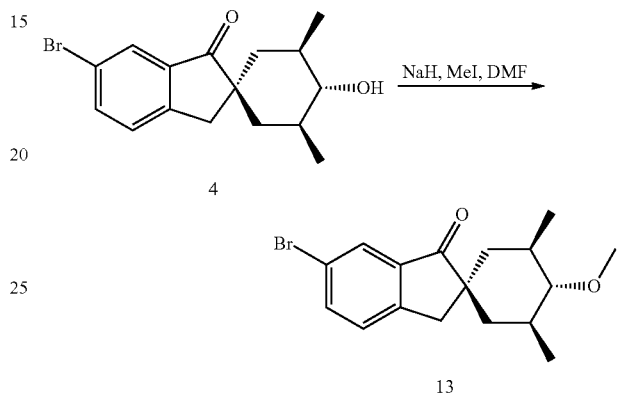

To a mixture of intermediate 4 (20.0 g, 61.9 mmol) in DMF (200 mL) was added NaH (5.0 g, 123.8 mmol) at 0° C. and the mixture was stirred for 15 min at 0° C. Methyl iodide (17.6 g, 123.8 mmol) was added at 0° C. and the mixture was warmed to rt and stirred for 1.5 h at rt. The mixture was quenched with H$_2$O and extracted with EtOAc. The combined organic phases were washed with H$_2$O followed by brine, dried and concentrated to afford crude product, which was purified by column on silica gel (petroleum ether: ethyl acetate; 30:1 to 5:1) to afford intermediate 13 (20 g).

Step 2: Synthesis of Intermediate 14

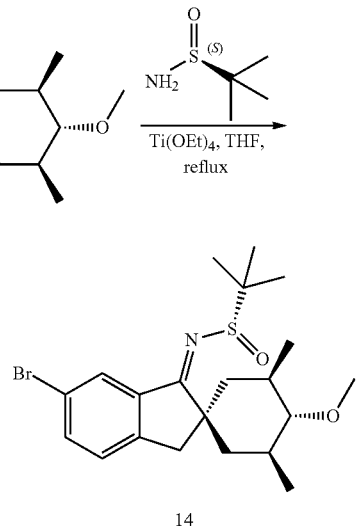

A mixture of intermediate 13 (20.0 g, 59.3 mmol) and titanium (IV) ethoxide (108.2 g, 474.4 mmol) in dry THF (200 ml) was stirred at rt for 1 h. (S)—N-tert-butylsulfinamide (29 g, 237.2 mmol) was added and the resulting mixture was stirred at 80° C. under $N_2$ atmosphere overnight. The reaction mixture was cooled and water (400 ml) was added. The mixture was filtered and the aqueous layer was extracted with ethyl acetate (3×400 mL). The combined organic phase was dried and concentrated under reduced pressure to give crude intermediate. This was purified by column chromatography on silica gel (petroleum ether: ethyl acetate; 20:1) to yield intermediate 14 (18.4 g).

Step 3: Synthesis of Intermediate 15

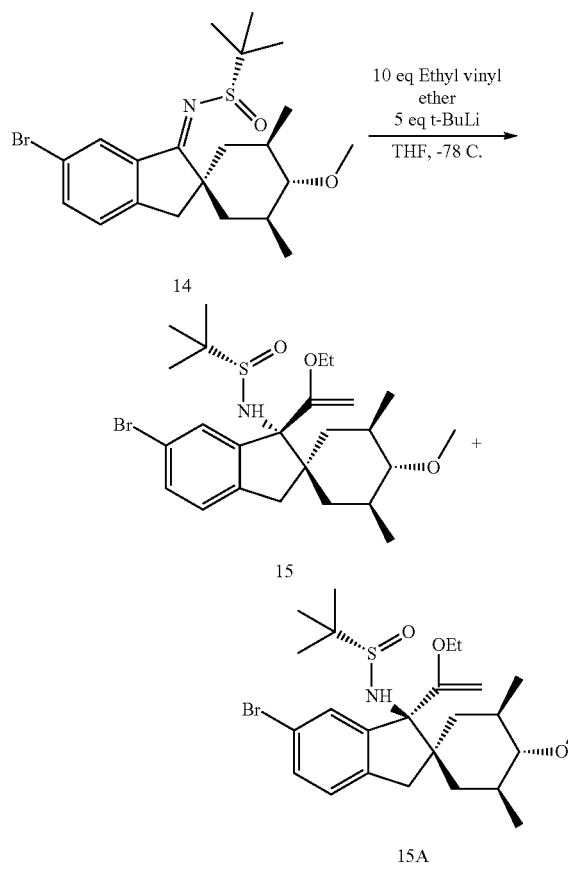

t-BuLi (131 mL, 170.3 mmol, 1.3 M in hexane) was added dropwise to a solution of ethyl vinyl ether (12.3 g, 170.3 mmol, 5.0 eq) in anhydrous THF (100 mL) at −78° C. under $N_2$ and the mixture was stirred for 20 min. The resulting mixture was stirred at 0° C. for another 45 min and re-cooled to −78° C. A pre-cooled solution of intermediate 14 (15.0 g, 34.1 mmol) in anhydrous THF (50 mL) at −78° C. was added dropwise and the mixture was stirred for 2 h at −78° C. The reaction mixture was quenched with sat. $NH_4Cl$ aqueous solution (50 mL) and extracted with EtOAc (3×300 mL). The organic phases were combined and concentrated under reduced pressure to give the residue, which was purified by column chromatography on silica gel (petroleum ether: ethyl acetate; 50:1 to 3:1) to afford intermediates 15 (11 g) and 15A (1.44 g), respectively.

LC-MS (method 1) tR=5.67 min; MS (ESI) m/z 514.2 $[M+H]^+$.

$^1H$ NMR ($CD_3OD$): δ 7.546 (s, 1H), 7.454-7.479 (d, 1H), 7.208-7.228 (d, 1H), 4.620-4.755 (d, 1H), 4.373-4.381 (m, 1H), 4.048-4.055 (m, 1H), 3.844-3.903 (m, 2H), 3.458-3.474 (s, 3H), 2.986-3.000 (m, 2H), 2.326-2.377 (m, 1H), 1.969-2.001 (m, 1H), 1.671 (s, 1H), 1.457-1.520 (t, J=12 Hz, 3H), 1.373-1.408 (m, 2H), 1.328 (s, 9H), 1.169-1.278 (m, 5H), 1.073-1.106 (d, 3H).

Step 4: Synthesis of Intermediate 16

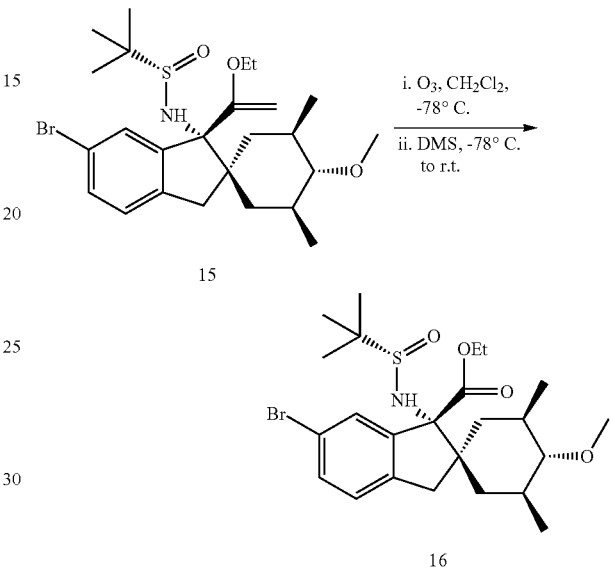

Intermediate 15 (4.8 g, 9.37 mmol) was added to a mixture of DCM in MeOH (5:1, 40 mL), and the mixture was cooled to −78° C. Ozone was bubbled through the mixture for 20 min. The mixture was purged with $N_2$ for 10 minutes and treated with $Me_2S$ (10 mL) at −78° C. The mixture was allowed to warm up to rt and stirred at rt for 3 h. The solvent was removed under vacuum, the residue was purified by column chromatography on silica gel (petroleum ether: ethyl acetate; 20:1 to 8:1) to give intermediate 16 (3.5 g).

LC-MS (method 1): tR=1.30 min; MS (ESI) m/z 516.1 $[M+H]^+$.

$^1H$ NMR ($CDCl_3$): δ 7.84 (s, 1H), 7.42-7.44 (d, J=8.0 Hz, 1H), 7.09-7.11 (d, J=8.0 Hz, 1H), 4.40 (s, 1H), 4.26-4.39 (m, 2H), 3.44 (s, 3H), 2.93-2.97 (d, J=15.6 Hz, 1H), 2.70-2.74 (d, J=15.2 Hz, 1H), 2.22-2.30 (t, J=10.0 Hz, 1H), 1.75-1.79 (m, 1H), 1.61-1.66 (m, 1H), 1.54-1.57 (m, 2H), 1.32-1.38 (m, 4H), 1.14 (s, 9H), 1.06-1.08 (d, J=6.0 Hz, 3H), 0.89-0.91 (d, J=6.0 Hz, 3H), 0.67-0.74 (m, 1H).

Step 5: Synthesis of Intermediate 17

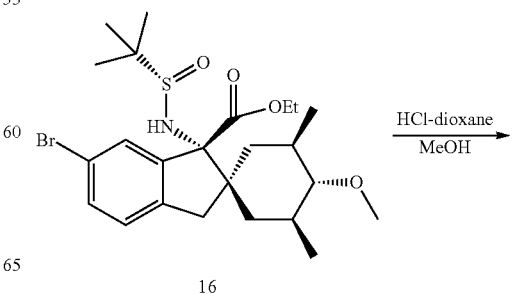

37

-continued

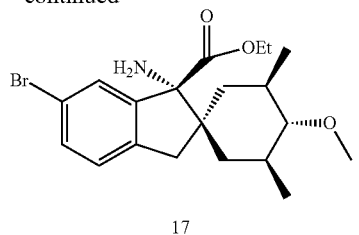

17

To a mixture of intermediate 16 (5.1 g, 10 mmol) in MeOH (10 mL) was added HCl in dioxane (4.0M, 8.0 mL). The resulting mixture was stirred for 1 h. Solvent was removed under reduced pressure to afford crude intermediate 17 (6.0 g), which was used for the next step without further purification.

Alternative Synthesis of Intermediate 17

Step 1. Synthesis of Intermediate 18

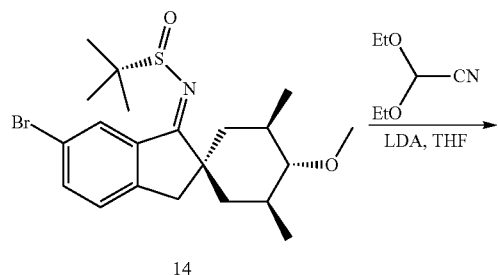

14

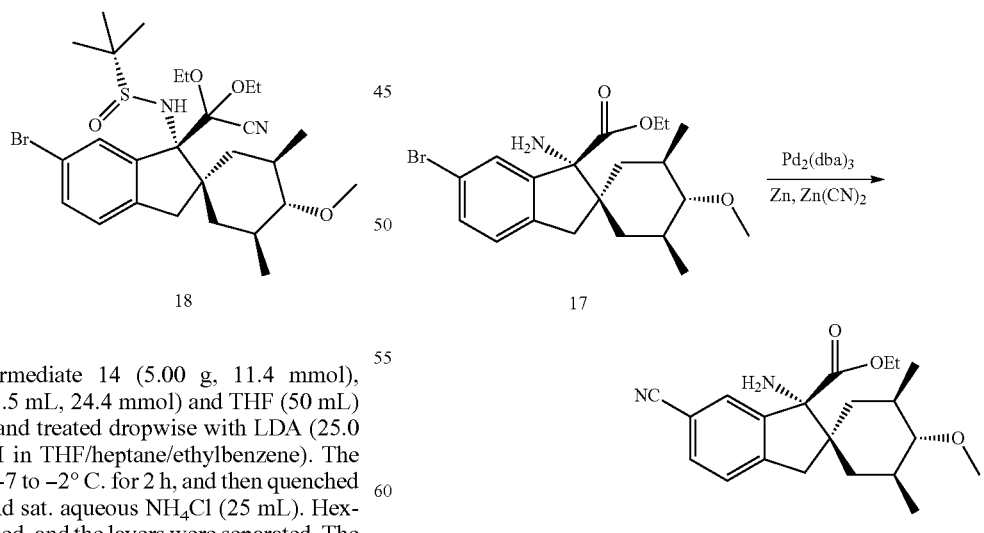

18

A mixture of intermediate 14 (5.00 g, 11.4 mmol), diethoxyacetonitrile (3.5 mL, 24.4 mmol) and THF (50 mL) was cooled to −7° C. and treated dropwise with LDA (25.0 mL, 45.0 mmol, 1.8M in THF/heptane/ethylbenzene). The mixture was stirred at −7 to −2° C. for 2 h, and then quenched with water (50 mL) and sat. aqueous NH4Cl (25 mL). Hexanes (100 mL) was added, and the layers were separated. The organic layer was washed with water, brine, and was concentrated under reduced pressure to give crude intermediate 18 (9.00 g) which was used directly in the next step.

LC-MS (method 1): tR=3.74 min, MS (ESI) m/z 523.2/525.2 [M-OEt+H]+

38

Step 2. Synthesis of Intermediate 17

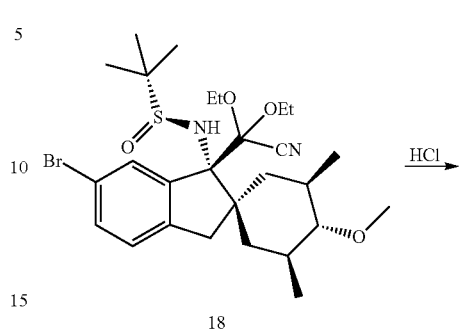

18

17

A mixture of above intermediate 18 (9.00 g, 11.4 mmol) in EtOH (30 mL) was treated with aqueous HCl (6 N, 20 mL). The reaction mixture was heated at 75° C. for 24 h and cooled to rt. The reaction was extracted with toluene (50 mL), and the aqueous phase was basified (pH=8) with aqueous NaOH (2 N, ~60 mL). Toluene (100 mL) was added and the mixture was stirred for 10 minutes. The organic layer was separated and washed with aqueous NaHCO3, brine and concentrated under reduced pressure. Hexanes was added and the solution was concentrated under reduced pressure to give crude intermediate 17 (3.47 g) which was used directly in the next step.

LC-MS: tR=0.86 min, MS (ESI) m/z 410.2/412.2 [M+H]+

Step 6: Synthesis of Intermediate 19

17

19

A mixture of compound 17 (500 mg, 1.9 mmol) under nitrogen, Zn(CN)2 (300 mg, 2.6 mmol), Pd2(dba)3 (150 mg, 0.16 mmol), dppf (160 mg, 0.32 mmol) and Zn dust (60 mg, 0.9 mmol) in DMF (15 mL) was heated to 120° C. for 3 h in CEM microwave reactor. The mixture was concentrated under vacuum and the residue was purified by column on silica gel (eluent: petroleum ether: ethyl acetate; 20:1 to 8:1) to afford intermediate 19 (300 mg).

LC-MS: tR=0.880; MS (ESI) m/z 308.1 [M+H]

Step 7: Synthesis of Intermediate 20

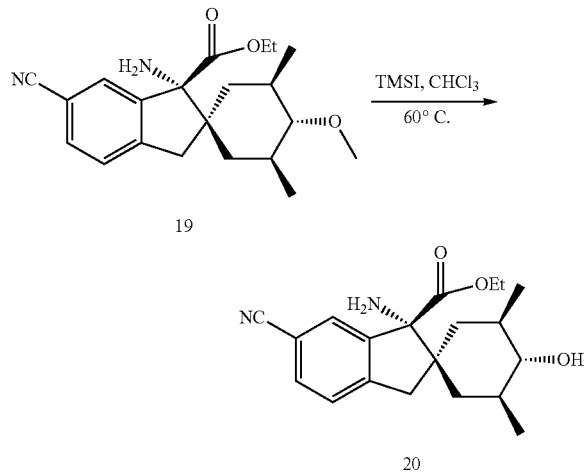

To a solution of intermediate 19 (3.1 g, 7.4 mmol) in CHCl$_3$ (20 ml) was added TMSI (10 ml) and stirred at 65° C. for 2 h. The mixture was cooled to rt and sat. Na$_2$S$_2$O$_3$ (10 mL), sat. NaHCO$_3$ aqueous solution (10 mL) were added, and the mixture was stirred for 10 minutes. The residue was partitioned between DCM (40 mL) and H$_2$O (10 mL). The organic layer was separated and washed with brine (10 mL), dried over Na$_2$SO$_4$, filtered and concentrated under vacuum to afford crude intermediate 20 (2.6 g), which was used for the next step without further purification.

Synthesis of Intermediate 26

Step 1: Synthesis Intermediate 22

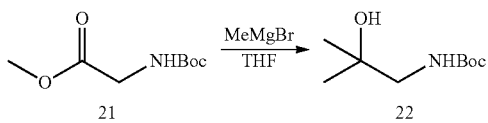

A mixture of intermediate 21 (2.0 g, 10.6 mmol) in anhydrous THF (20 mL) was added to methyl magnesium bromide (14 mL, 42 mmol, 3.0 M in Et$_2$O) at −30° C. under a N$_2$ atmosphere. The mixture was stirred at −30° C. for 4 h, and then quenched by addition of H$_2$O (40 mL) and aqueous HCl (1 M, 50 mL) with stirring at 0° C. The mixture was separated, and the aqueous layer was extracted with EtOAc (2×50 mL). The combined organic layers were washed with brine (2×50 mL), dried, filtered and concentrated under vacuum to give the crude intermediate 22 (2.1 g), which was used directly in the next step without purification.

$^1$H NMR: (CDCl$_3$): δ 4.97 (br, 1H), 3.10 (s, 2H), 2.17 (br, 1H), 1.44 (s, 9H), 1.20 (s, 6H).

Step 2: Synthesis of Intermediate 23

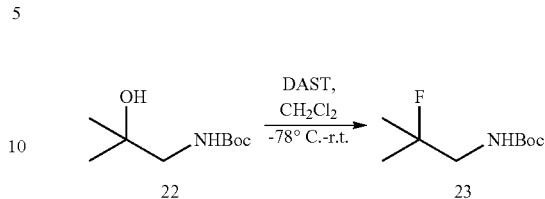

To a mixture of intermediate 22 (3.0 g, 15.9 mmol) in anhydrous DCM (50 mL) was added DAST (2.3 mL, 17.4 mmol) at −78° C. under a N$_2$ atmosphere. The mixture was stirred at −78° C. for 1 h, and then allowed to warm to rt overnight. The mixture was cooled to 0° C., and quenched by slow addition of sat. aqueous layer NaHCO$_3$ (30 mL) with stirring at 0° C. The mixture was separated, and the aqueous layer was extracted with DCM (2×20 mL). The combined organic layer was washed with brine (2×30 mL), dried, filtered and concentrated under vacuum to yield the crude intermediate 23 (2.5 g), which was used directly in the next step without purification.

$^1$H NMR: (CDCl$_3$): δ 4.82 (br, 1H), 3.30-3.35 (d, J=6.0 Hz, 1H), 3.24-3.26 (d, J=6.0 Hz, 1H), 1.44 (s, 9H), 1.37 (s, 3H), 1.35 (s, 3H).
$^{19}$F NMR: (CDCl$_3$): δ-144.93.

Step 3: Synthesis of Intermediate 24

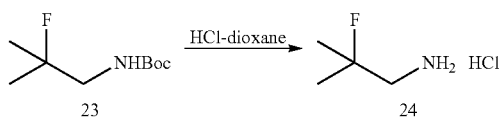

To a mixture of intermediate 23 (2.0 g, 10.5 mmol, crude) in anhydrous DCM (10 mL) was added HCl in dioxane (4 M, 10 mL, 40 mmol) with stirring. The mixture was stirred at rt for 2 h after which time the solvent was removed under reduced pressure. The residue was treated with a mixture of DCM-petroleum ether (1:1, 3×10 mL) and the precipitate was collected and dried under vacuum to yield the crude intermediate 24 (1.1 g), which was used directly in the next step without purification.

$^1$H NMR: (CD$_3$OD): δ 3.15-3.25 (d, J=20.0 Hz, 2H), 1.51 (s, 3H), 1.48 (s, 3H). $^{19}$F NMR: (CDCl$_3$): δ-147.59.

Intermediate 24 can alternatively be obtained from dibenzyl amine according to the following procedure:

Step 1: Synthesis of Intermediate 22a

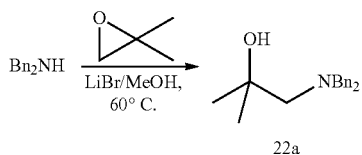

To a slurry of LiBr (1.66 g, 19.06 mmol, 0.2 equiv) in MeOH (3.8 mL) was added Bn$_2$NH (18.80 g, 95.30 mmol, 1.0 equiv) at about 20-25° C. Isobutylene oxide (10.31 g, 142.95 mmol, 1.5 equiv) was added at a rate to maintain the temperature below 65° C. After the addition was complete, the batch was stirred at about 60° C. for 6 h. The batch was cooled to about 20° C., and toluene (37.6 mL) and water (18.8 mL) were added. After stirring for about 5 min, the layers were separated. The organic phase was concentrated under vacuum to an oil, and toluene was added and the solution was again distilled to an oil. Compound 22a was obtained as a toluene solution (33.88 g, 75.1 wt. %) in 99% yield and used directly in the next step.

$^1$H NMR: (CDCl$_3$): δ 1.11 (s, 6H), 2.42 (s, 1H), 2.56 (s, 2H), 3.70 (s, 4H), 7.23-7.35 (m, 10H).

Step 2: Synthesis of Intermediate 23a

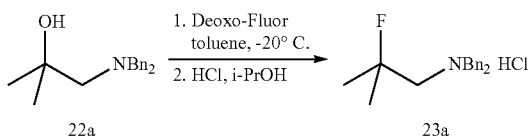

A solution of intermediate 22a (10.32 g, 75.1 wt. %, 28.77 mmol) in anhydrous toluene (40 mL) was cooled to –20° C. Deoxo-Fluor (7.0 g, 31.64 mmol, 1.10 eq) was added dropwise while keeping the temperature below –10° C. The mixture was stirred at –20° C. to –10° C. for 3 h. The reaction was then quenched by the addition of aqueous KOH solution (6.46 g of 85 wt. % KOH pellets, 96.86 mmol, 3.40 eq in 25.84 g of water) while keeping the temperature below 10° C. The mixture was warmed to rt and the layers were separated. The organic layer was washed with water (3×25 mL). The organic phase was concentrated under vacuum and repeatedly distilled with heptane until the water content was <200 ppm. The crude product was diluted with heptane (25 mL) and filtered through a silica gel pad (8 g silica gel). The silica gel pad was rinsed with heptane (2×20 mL) and the combined heptane filtrates were distilled under vacuum to the minimum volume and repeatedly distilled with isopropanol. Isopropanol (40 mL) was added and the solution was cooled to –10° C. Hydrogen chloride solution in isopropanol (8.3 mL, 5.2 N, 43.16 mmol, 1.50 eq) was added while keeping the temperature below 30° C. After stirring at 20-25° C. for 1 h, the mixture was heated to 75° C. to get a clear solution and held at this temperature for 15 min. The mixture was cooled to 20-25° C. and stirred at this temperature for 2-3 h. The solid was filtered, washed with heptane, and dried under vacuum at 20-25° C. to give the product as a white solid (5.74 g, 91 wt. %) in 65% yield.

$^1$H NMR: (CDCl$_3$): δ1.31-1.35 (d, J=21.5 Hz, 6H), 3.35-3.38 (d, J=18.8 Hz, 2H), 4.39-4.45 (dd, J=18.6 Hz, J=3.5 Hz, 4H), 7.50-7.62 (m, 10H). $^{19}$F NMR: (CDCl$_3$): δ –143.58.

Intermediate 23a can alternatively be obtained from dibenzyl amine according to the following procedure:

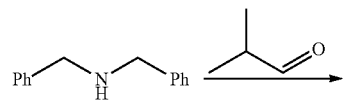

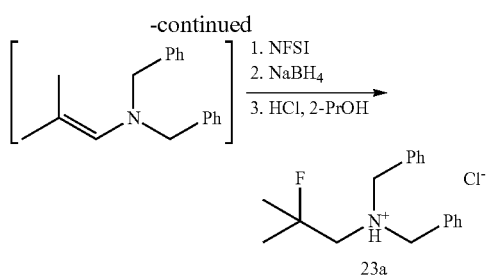

To a reaction vessel equipped with a Dean-Stark trap (pre-filled with isobutyraldehyde) was charged dibenzylamine (40.06 g, 203.06 mmol), isobutyraldehyde (19.04 g, 264.98 mmol, 1.30 equiv) and toluene (20 mL). The mixture was heated to reflux under nitrogen to remove water (~3.8 mL) in ~4 h, while the temperature was gradually raised to ~115° C.). The excess of isobutyraldehyde and toluene was then distilled under reduced pressure. The crude liquid was cooled to –10° C. and a solution of N-fluorobenzenesulfonimide (NFSI, 76.84 g, 243.67 mmol, 1.20 equiv) in N,N,-dimethyl acetamide (100 mL) was slowly added below 20° C. The mixture was stirred at room temperature until complete conversion (5-20 h). The mixture was cooled to 0° C. and a solution of NaBH$_4$ (4.22 g, 111.68 mmol, 0.55 equiv) in N,N,-dimethyl acetamide (48 mL) was added below 20° C. After addition, the mixture was stirred at room temperature for 2.5 h. The mixture was cooled to 10° C. and a solution of NaOH (10.56 g, 263.98, 1.50 equiv) in water (40 mL) was slowly added (gas was released), followed by 200 mL of water. The mixture was stirred at room temperature for 0.5 h, and extracted with heptane (250 mL). The organic layer was washed with water (2×150 mL) and distilled at normal pressure (up to 115° C.). 2-Propanol (150 mL) was added and the mixture was distilled to remove solvents (50 mL). Acetic anhydride (2.07 g, 20.29 mmol, 0.10 equiv) was added at ~30° C. and stirred for 0.5 h. To the mixture was added 4.5 M HCl in 2-propanol (54 mL, 243.67 mol, 1.20 equiv) at ~30° C. The resulting suspension was stirred at 60° C. for 1 h, and then cooled to 20° C. in 1 h. The solid was filtered, rinsed with 2-propanol (50 mL), and dried to give a white solid (23a) (47.46 g, 97.7% purity) in 74% yield.

Step 3: Synthesis of Intermediate 24

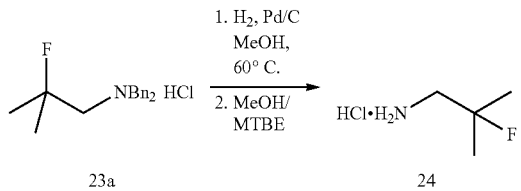

To a hydrogenation vessel was charged 10% palladium on carbon (50% wet with water, 0.53 g, 0.25 mmol, 0.01 equiv), 23a (8.74 g, 89.5 wt. %, 25.41 mmol, 1.00 equiv) and methanol (24 mL). The mixture was hydrogenated at 60° C. and 400 psi of H$_2$ for 5-8 h. After cooling to 20-25° C., the mixture was filtered through a Celite pad, and the pad was rinsed with MeOH. The solvent was distilled under vacuum at 50° C. to a volume of 4-5 mL. MTBE (25 mL) was added to the batch dropwise with stirring to form a slurry. After stirring for 30 min at 50° C., the batch was cooled to 20-25° C., held at this temperature for 1 h, and filtered. The solid was rinsed with MTBE and then dried at 25° C. under vacuum for 4 h. Compound 24 was obtained as a white solid (3.24 g, 96 wt. %) in 96% yield. $^1$H NMR: (CD$_3$OD): δ 1.44-1.49 (d, J=21.2 Hz, 6H), 3.13-3.18 (d, J=19.7 Hz, 2H). $^{19}$F NMR: (CDCl$_3$): δ-147.55.

Step 4: Synthesis of Intermediate 25

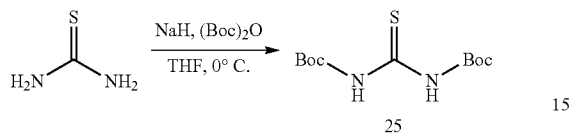

To a stirred mixture of thiourea (23.0 g, 302 mmol) in THF (5.0 L) under argon at 0° C. was added NaH (29.9 g, 755 mmol, 60% in mineral oil). After 5 min, the ice bath was removed, and the reaction mixture was stirred at rt for 10 min. The mixture was cooled to 0° C. and Boc$_2$O (138 g, 635 mmol) was added. The ice bath was removed after 30 min of stirring at that temperature. The resulting slurry was stirred for another 2 h at rt. The reaction was quenched with an aqueous solution of sat. NaHCO$_3$ (500 mL) and poured into water (5.0 L) and extracted with EtOAc (3×2.0 L). The combined organic layer was dried over Na$_2$SO$_4$, filtered, and concentrated under reduced pressure to afford intermediate 25 (80.0 g), which was used for the next step without further purification.

LCMS (method 1): $t_R$=1.15 min, MS (ESI) m/z 575.2 [2M+Na]$^+$.

Step 5: Synthesis of Intermediate 26

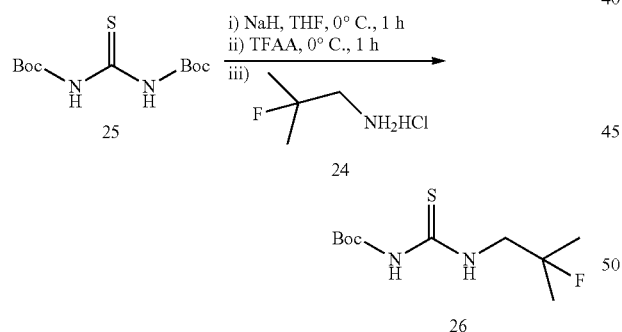

To a mixture of intermediate 25 (3.9 g, 14.2 mmol) and anhydrous THF (285 mL) was added NaH (0.68 g, 17.0 mmol, 60% in mineral oil) at 0° C. and the mixture was stirred for 1 h, then TFAA (2.20 mL, 15.6 mmol) was added and the stirring continued for an additional 1 h. A pre-mixed mixture of intermediate 24 (2.0 g, 15.6 mmol) and Et$_3$N (3.96 mL, 28.40 mmol) in anhydrous THF (130 mL) was added and the resulting mixture was stirred at rt overnight. Water (150 mL) was added to quench the reaction and the mixture was extracted with EtOAc (3×200 mL). The combined organic layer was dried, filtered and the solvent was removed under reduced pressure. The residue was purified by flash column chromatography on silica gel (eluent: petroleum ether: ethyl acetate from 50:1 to 8:1) to afford intermediate 26 (2.49 g).

LC-MS (method 1): $t_R$=1.08 min, MS (ESI) m/z 194.8 [M−55]$^+$.

$^1$H NMR (CD$_3$OD): δ 3.88-3.93 (m, 2H), 1.53 (s, 9H), 1.43 (s, 3H), 1.38 (s, 3H)

$^{19}$F NMR (CD$_3$OD): δ-144.15

Example 2

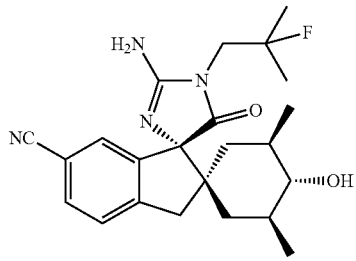 [SMILES: C[C@@H]1C[C@@]2(Cc3ccc(C#N)cc3[C@]23N=C(N)N(CC(C)(C)F)C3=O)C[C@H](C)[C@H]1O]

Step 1: Synthesis of Intermediate 27

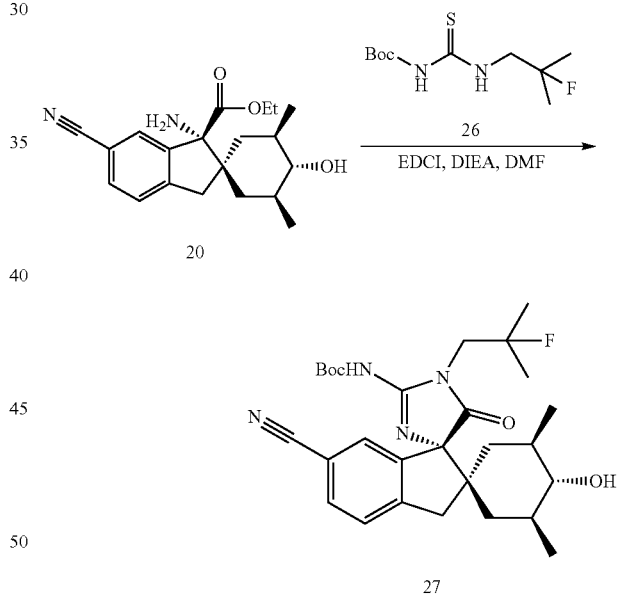

To a solution of intermediate 20 (550 mg, 1.61 mmol) in DMF (5 mL), intermediate 26 (425 mg, 1.69 mmol), EDCI (614 mg, 3.22 mmol) and DIEA (416 mg, 3.22 mmol) were added. The mixture was stirred at rt for 36 h. EtOAc (200 mL) was added, followed by water (20 mL), and the mixture was stirred for 10 minutes. The organic layer was separated and washed with water (3×20 mL), brine (3×50 mL), dried, and solvent was removed under reduced pressure to afford crude product. The residue was purified by column chromatography (petroleum ether: ethyl acetate; 5:1) to afford intermediate 27 (547 mg).

LC-MS: $t_R$=1.14; MS (ESI) m/z 513.3 [M+H]$^+$.

Step 2: Synthesis of Example 2

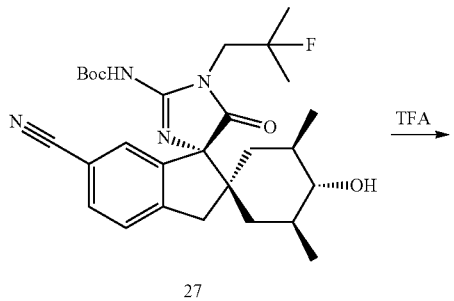

To a mixture of intermediate 27 (400 mg, 0.56 mmol) in DCM (5 mL) was added TFA (1 mL) and the mixture was stirred at rt for 2 h. To this mixture, a sat. NaHCO$_3$ solution (10 mL) was added and stirred for 10 minutes. The mixture was partitioned between DCM (10 mL) and H$_2$O (10 mL). The organic layer was separated and washed with brine (10 mL), dried over Na$_2$SO$_4$ and concentrated under reduced pressure. The residue was purified by preparative HPLC (basic method 1) and SFC method A to give compound Example 2 (303.9 mg).

LC-MS (method 1): t$_R$=0.90 min, MS (ESI) m/z 413.2[M+H]$^+$.

$^1$H NMR (CD$_3$OD): δ7.63-7.65 (dd, J=8.0, 1.6 Hz, 1H), 7.49-7.51 (d, J=8.0 Hz, 1H), 7.30 (s, 1H), 3.69-3.76 (m, 2H), 3.26-3.30 (m, 1H), 3.15-3.19 (m, 1H), 2.55-2.59 (t, J=8.0 Hz, 1H), 1.79-1.84 (m, 1H), 1.27-1.63 (m, 11H), 1.03-1.09 (t, J=12.0 Hz, 1H), 1.00-1.01 (t, J=4.0 Hz, 3H), 0.96-0.97 (d, J=4.0 Hz, 3H). $^{19}$F NMR: (CD$_3$OD): δ −139.5.

Example 3

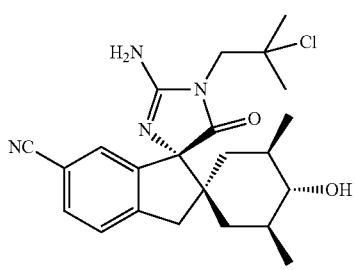 [SMILES: C[C@@H]1C[C@@]2(Cc3ccc(C#N)cc3[C@]23N=C(N)N(CC(C)(C)Cl)C3=O)C[C@H](C)[C@H]1O]

Step 1: Synthesis of Intermediate 28

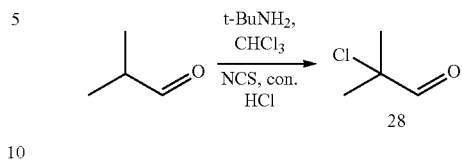

2-methylproponal (9.3 g, 129 mmol) was added to t-BuNH$_2$ (4.75 g, 129 mmol) at 0° C. and stirred at rt for 2 h. To this mixture CHCl$_3$ (130 mL) was added, and the mixture was dried over Na$_2$SO$_4$ and filtered. To the resultant solution, NCS (18.20 g, 136 mmol) was added at 0° C., followed by stirring at rt for 5 h. Water (100 mL) was poured into the reaction mixture and the mixture was extracted with CHCl$_3$ (3×100 mL). The combined organic layer was washed with water (200 mL), dried, and concentrated under reduced pressure. To the resultant residue, concentrated HCl was added. The mixture was stirred at rt for 5 h, and sat. NaHCO$_3$ (200 mL) was added. The product was extracted with CHCl$_3$ and the residue was distilled at atmospheric pressure to obtain intermediate 28 (2 g).

$^1$H NMR (CDCl$_3$): δ 9.44 (s, 1H), 1.65 (s, 6H).

Step 2: Synthesis of Intermediate 29

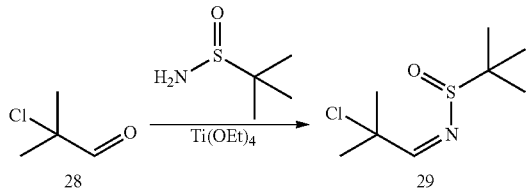

The mixture of intermediate 28 (1.06 g, 10 mmol) and titanium (IV) ethoxide (2.72 mL, 12 mmol) in anhydrous THF (22 mL), (±) N-tert-butylsulfinamide (1.21 g, 9 mmol) was added. The resulting mixture was stirred at reflux under N$_2$ atmosphere for 4 h. The reaction mixture was cooled and water (20 mL) was added. The resulting mixture was filtered and the aqueous layer was extracted with ethyl acetate (3×20 mL). The combined organic phase was dried over Na$_2$SO$_4$ and concentrated under reduced pressure to give intermediate 29 (1 g).

$^1$H NMR (CDCl$_3$): δ 7.94 (s, 1H), 1.71 (s, 6H), 1.14 (s, 9H).

Step 3: Synthesis of Intermediate 30

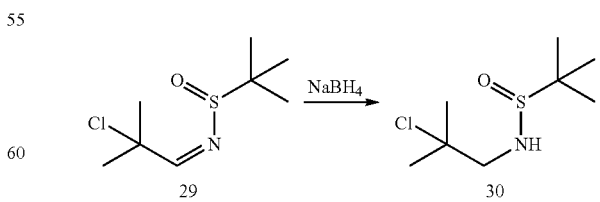

To a solution of intermediate 29 (0.7 g, 3.33 mmol) in anhydrous THF (5 mL) was added NaBH$_4$ (0.25 g, 6.66 mmol) at 0° C. The reaction mixture was stirred at rt for 16 h, the reaction was quenched with sat. NH$_4$Cl solution (5 mL), aqueous KHCO$_3$ (20 mL), and EtOAc (20 mL). The aqueous layer was extracted with EtOAc (2×20 mL). The combined organic layer was dried, and concentrated under reduced pressure to yield crude intermediate 30 (260 mg), which was used for the next step without further purification.

$^1$H NMR (CDCl$_3$): δ 3.40-3.45 (m, 1H), 3.11-3.17 (m, 1H), 1.55-1.57 (m, 6H), 1.23 (s, 9H).

Step 4: Synthesis of Intermediate 31

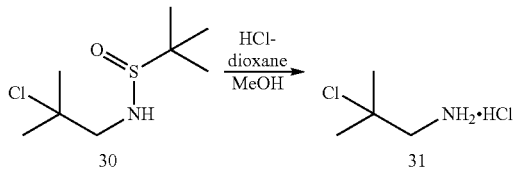

To the mixture of intermediate 30 (450 mg, 2.12 mmol) in dry MeOH (3 mL) was added HCl in dioxane (4 M, 2 mL). The resulting mixture was stirred at rt for 2 h. The solvent was removed under reduced pressure to afford crude product 31, which was used for the next step without further purification.

Example 3 was synthesized in a manner similar to Example 1, using intermediate 31 in step 10.

LC-MS (method 1): t$_R$=0.86 min, MS (ESI) m/z 429.2 [M+H]$^+$.

$^1$H NMR: (CD$_3$OD): δ 7.60-7.62 (d, J=7.6 Hz, 1H), 7.45-7.47 (d, J=7.6 Hz, 1H), 7.27 (s, 1H), 3.76-3.85 (m, 2H), 3.11-3.25 (m, 2H), 2.51-2.56 (m, 1H), 1.57-1.58 (d, J=4.0 Hz, 1H), 1.42-1.52 (m, 9H), 1.23-1.26 (m, 1H), 1.03-1.09 (m, 1H), 0.97-0.99 (m, 3H), 0.93-0.94 (m, 3H) ppm.

Example 4

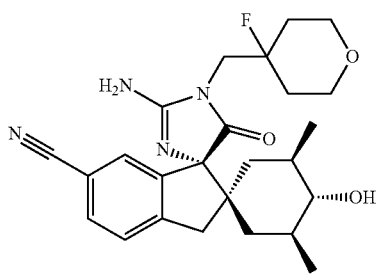 [SMILES: C[C@@H]1C[C@@]2(Cc3ccc(C#N)cc3[C@]23N=C(N)N(CC2(F)CCOCC2)C3=O)C[C@H](C)[C@H]1O]

Step 1: Synthesis of Intermediate 32

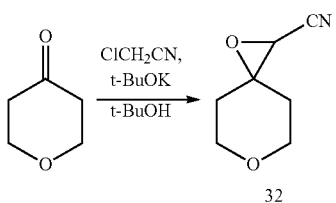 [SMILES: "t-BuOH" ; O=C1CCOCC1 ; N#CC1OC12CCOCC2]

A mixture of dihydro-2H-pyran-4(3H)-one (50.0 g, 500 mmol) and 2-chloroacetonitrile (35.0 g, 350 mmol) in tert-butanol (50 mL) was stirred for 30 min. To this mixture was added a solution of t-BuOK (60 g, 550 mmol) in tert-butanol (500 mL) over 40 minutes. The reaction mixture was stirred at rt for 16 h. It was diluted with water (100 mL) and quenched with HCl (10% aqueous, 20 mL). The reaction mixture was concentrated to one-third of its original volume, and extracted with Et$_2$O (3×200 mL). The combined organic layer was washed with brine, dried, and concentrated to afford crude intermediate 32 (57 g), which was used directly in the next step without purification.

Step 2: Synthesis of Intermediate 33

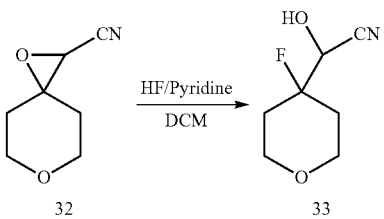 [SMILES: N#CC1OC12CCOCC2 ; N#CC(O)C1(F)CCOCC1]

To a mixture of intermediate 32 (57 g) in DCM (200 mL) in a polypropylene bottle at 0° C., 70% hydrogen fluoride-pyridine (50 mL) was added slowly. The mixture was allowed to warm to rt overnight. The reaction mixture was diluted with EtOAc (500 mL) and poured into sat. aqueous NaHCO$_3$ (200 mL). Additional solid NaHCO$_3$ was used to neutralize the mixture carefully until bubbling ceased. The aqueous layer was extracted with EtOAc (3×500 mL). The combined organic layer was washed with aqueous HCl (1%, 200 mL) brine, dried and concentrated to give crude intermediate 33 (54 g), which was used directly in the next step without purification.

$^1$H NMR: (CDCl$_3$): δ 4.37 (m, 2H), 3.96-2.70 (m, 4H), 1.97-1.81 (m, 4H).

Step 3: Synthesis of Intermediate 34

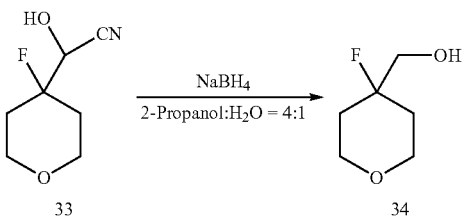 [SMILES: N#CC(O)C1(F)CCOCC1 ; "NaBH4" ; OCC1(F)CCOCC1]

To a mixture of intermediate 33 (54 g; 340 mmol) in 2-propanol (1000 mL) and water (250 mL) at 0° C., NaBH$_4$ (20 g, 509 mmol) was added. The mixture was stirred and allowed to warm to rt over 3 h. The reaction was quenched with acetone (50 mL), and stirred for another 1 h. The clear liquid was separated from solid by decantation. EtOAc (100 mL) was used to wash the solid, and the filtrates were combined. The combined organic solution was concentrated under reduced pressure and purified with flash column chromatography on silica gel (5-20% ethyl acetate in hexanes) to give intermediate 34 (22 g).

¹H NMR: (CDCl₃): δ: 3.82-3.77 (m, 4H), 3.72-3.52 (dd, J=20.8, 6.4 Hz, 2H), 2.69 (s, 1H), 1.82-1.60 (m, 4H).

Step 4: Synthesis of Intermediate 35

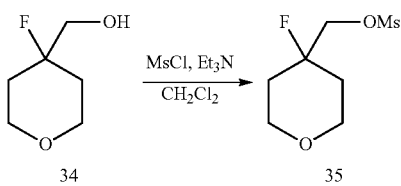

MsCl (25.8 g, 225 mmol) was added to a mixture of intermediate 34 (20 g, 150 mmol) and TEA (22.7 g, 225 mmol) in DCM (200 mL) at 0° C. The mixture was stirred at rt for 2 h, and then water (100 mL) was added. The aqueous layer was extracted with DCM (2×200 mL), organic phases were combined, dried and solvent was removed under reduced pressure to afford crude intermediate 35 (30 g), which was used for the next step without further purification.

¹H NMR: (CDCl₃): δ: 4.22 (d, J=20.0 Hz, 2H), 3.87-3.82 (m, 4H), 3.06 (s, 3H), 1.88-1.68 (m, 4H).

Step 5: Synthesis of Intermediate 36

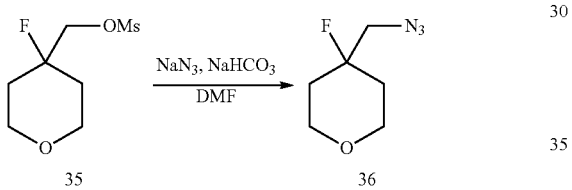

To a mixture of intermediate 35 (10 g, 47 mmol) in DMF (150 mL) was added NaN₃ (16 g, 250 mmol) and NaHCO₃ (9.3 g, 100 mmol) at rt. The mixture was stirred at 120° C. for 20 h. The reaction quenched with water at rt, extracted with EtOAc (2×200 mL). The organic phases were combined, dried and solvent was removed under vacuum to afford crude intermediate 36 (8 g), which was used for the next step without further purification.

Step 6: Synthesis of Intermediate 37

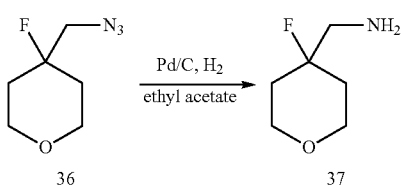 [SMILES: [N-]=[N+]=NCC1(F)CCOCC1 ; "ethyl acetate" ; NCC1(F)CCOCC1]

To a mixture of intermediate 36 (8 g, 50 mmol) in EtOAc (100 mL) was added 10% Pd/C (0.8 g) under a N₂ atmosphere, the mixture was degassed and exchanged with hydrogen for 3 times. The final mixture was stirred at rt under 1 atm. hydrogen atmosphere for 24 h. The catalyst was filtered off through a pad of celite and washed with EtOAc (2×50 mL). The combined filtrate was concentrated under reduced pressure to yield intermediate 37 (5.3 g).

¹H NMR: (CD₃OD): δ 3.83-3.79 (m, 4H), 2.76-2.71 (d, J=8.0 Hz, 2H), 1.83-1.65 (m, 4H).

¹⁹F NMR: (CD₃OD) δ: −169.66.

Example 4 was synthesized in a manner similar to Example 1, using intermediate 37 in step 10.

LC-MS (method 1): $t_R$=0.80 min, MS (ESI) m/z 455.2 [M+H]⁺.

¹H-NMR: (CD₃OD): δ 7.61-7.63 (d, J=7.6 Hz, 1H), 7.47-7.49 (d, J=8.0 Hz, 1H), 7.30 (s, 1H), 3.63-3.83 (m, 6H), 3.23-3.27 (m, 1H), 3.12-3.16 (m, 1H), 2.52-2.57 (t, J=10.0 Hz, 1H), 1.48-1.82 (m, 7H), 1.38-1.44 (t, J=12.0 Hz, 1H), 1.23-1.28 (m, 1H), 0.97-1.05 (m, 4H), 0.94-0.95 (d, J=4.0 Hz, 3H).

¹⁹F NMR: (CD₃OD): δ-160.48

Example 5

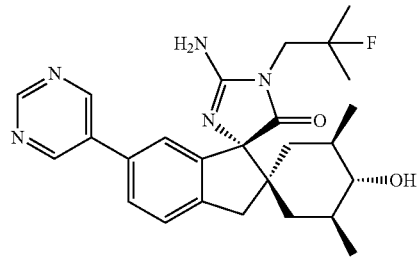 [SMILES: C[C@@H]1C[C@@]2(Cc3ccc(-c4cncnc4)cc3[C@]23N=C(N)N(CC(C)(C)F)C3=O)C[C@H](C)[C@H]1O]

Step 1: Synthesis of Intermediate 38

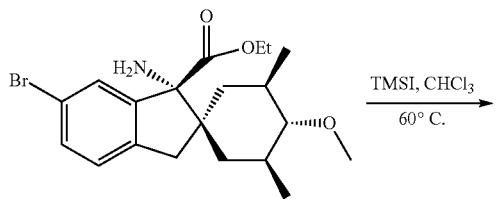

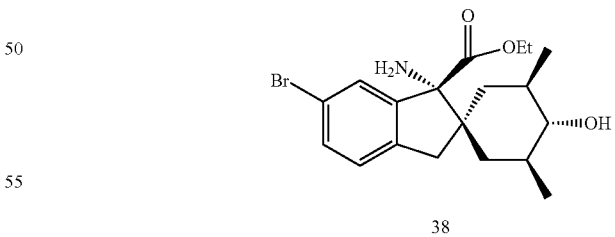

To a solution of intermediate 17 (3.6 g, 7.4 mmol) in CHCl₃ (25 ml) was added TMSI (10 ml) and the mixture was stirred at 65° C. for 2 h. The mixture was cooled to rt, sat. Na₂S₂O₃ (10 mL), and sat. NaHCO₃ aqueous solution (10 mL) were added, and the mixture was stirred for 10 minutes. The mixture was partitioned between DCM (50 mL) and H₂O (10 mL). The organic layer was separated and washed with brine (10 mL), dried over Na₂SO₄, filtered and concentrated under reduced pressure to afford crude intermediate 38 (2.6 g), which was used for the next step without further purification.

Step 2: Synthesis of Intermediate 39

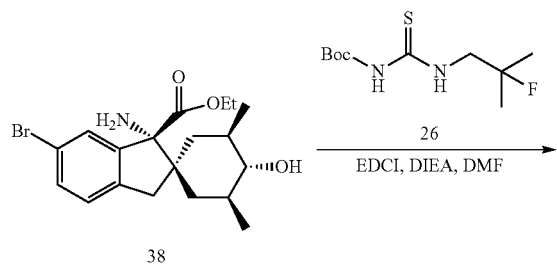

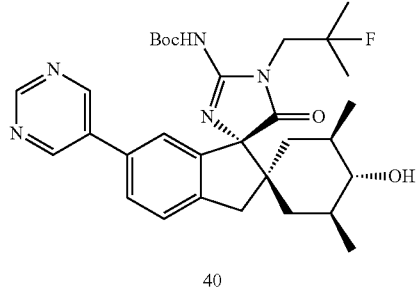

40

To a solution of intermediate 39 (350 mg, 0.6 mmol) in dioxane (5 mL) under N₂ atmosphere, 5-pyrimidine boronic acid (90 mg, 0.66 mmol) and aqueous Cs₂CO₃ solution (2 mL, 2 M in water) were added. The mixture was purged by bubbling a steam of N₂ for 5 min, then Pd(dppf)Cl₂ (40 mg, 0.06 mmol) was added. The mixture was stirred for 2 h at 110° C. under a N₂ atmosphere. The reaction was cooled to rt, diluted with EtOAc and filtered. The filtrate was washed with aqueous Na₂CO₃ (5 mL) and concentrated under reduced pressure to afford crude intermediate 40 (300 mg) which was used for the next step without further purification.

Step 4: Synthesis of Example 5

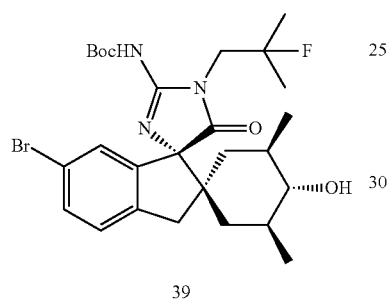

39

To a mixture of intermediate 38 (2.5 g, 6.4 mmol) in DMF (20 mL) was added intermediate 26 (1.8 g, 7.0 mmol, 1.1 eq), EDCI (2.5 g, 13 mmol) and DIEA (1.7 g, 13 mmol). The mixture was stirred overnight. The reaction mixture was diluted with water and extracted with EtOAc (3×30 mL). The combined organic layers were washed with brine (3×30 mL), dried, the solvent was removed under reduced pressure to afford crude product, which was purified by column (petroleum ether: ethyl acetate=20:1 to 5:1) to give intermediate 39 (2.8 g).

Step 3: Synthesis of Intermediate 40

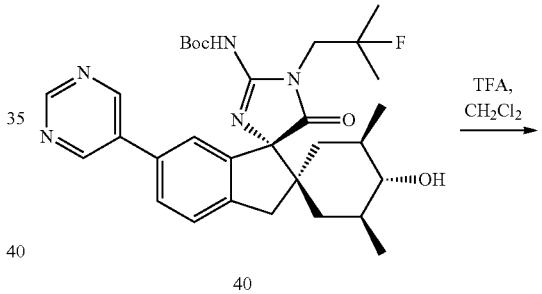

40

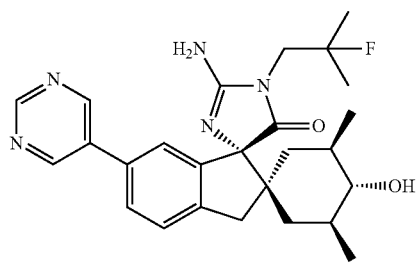

Example 5

To a solution of intermediate 40 (300 mg, 0.53 mmol) in DCM (5 mL) was added TFA (1 mL) and the mixture was stirred at rt for 2 h. To this mixture, sat. NaHCO₃ solution (10 mL) was added and stirred for 10 minutes. The residue was partitioned between DCM (10 mL) and H₂O (10 mL). The organic layer was separated and washed with brine (10 mL), dried over Na₂SO₄, filtered and concentrated under reduced pressure. The residue was purified by preparative HPLC (basic, method 1) to give Example 5 (141 mg). LC-MS (method 1): MS (ESI) m/z 466.2[M+H]⁺. ¹H NMR: (CD₃OD): δ 9.12 (s, 1H), 9.02 (s, 2H), 7.64-7.62 (dd, J=7.6, 1.6 Hz, 1H), 7.51 (d, J=8.0 Hz, 1H), 7.29 (s, 1H), 3.80-3.66 (m, 2H), 3.30-3.13 (m, 2H), 2.59 (t, J=10.0 Hz, 1H), 1.85 (d, J=12.4 Hz, 1H),

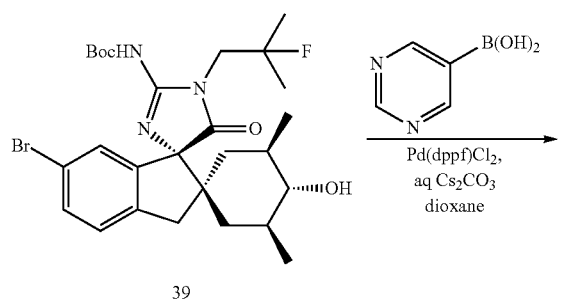

39

1.65-1.32 (m, 10H), 1.11-1.05 (m, 1H), 1.02 (d, J=6.4 Hz, 3H), 1.02 (d, J=6.4 Hz, 3H). $^{19}$F NMR: (CD$_3$OD): δ-139.27.

Example 6

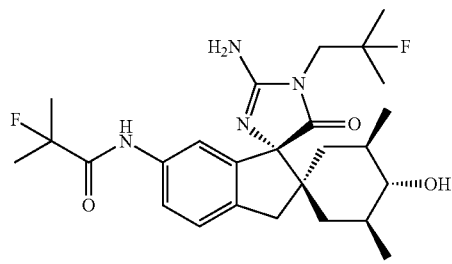 [SMILES: C[C@@H]1C[C@@]2(Cc3ccc(NC(=O)C(C)(C)F)cc3[C@]23N=C(N)N(CC(C)(C)F)C3=O)C[C@H](C)[C@H]1O]

Step 1: Synthesis of Intermediate 41

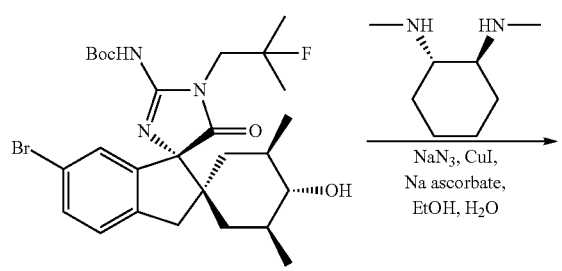

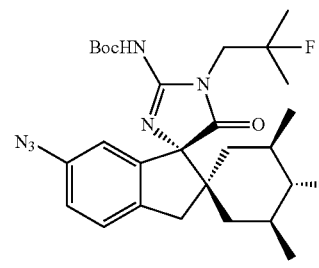

To a mixture of intermediate 39 (1.0 g, 1.8 mmol) in ethanol (23 mL) and water (10 mL), NaN$_3$ (300 mg, 3.6 mmol), CuI (40 mg, 10%) sodium ascorbate (40 mg, 0.20 mmol, 5%) and N,N'-dimethyl-cyclohexane-1,2-diamine (40 mg, 0.28 mmol, 15%) were added under N$_2$ atmosphere. The mixture was stirred for 3 h at 90° C. under a N$_2$ atmosphere. The mixture was cooled to rt, diluted with EtOAc and filtered. The filtrate was concentrated to afford crude intermediate 41 (830 mg) which was used for the next step without further purification.

Step 2: Synthesis of Intermediate 42

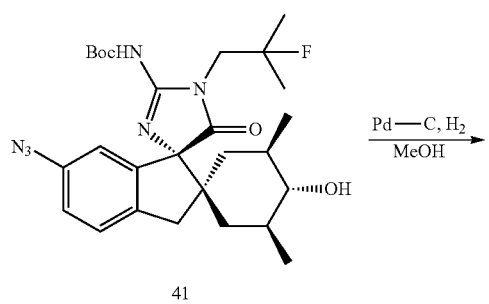

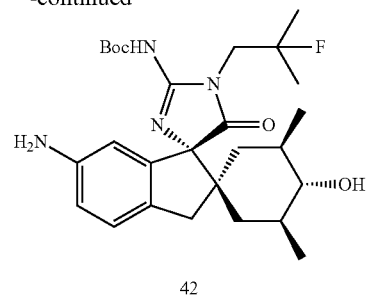

To a mixture of intermediate 41 (830 mg, 1.6 mmol) in MeOH (10 mL) was added 10% Pd/C (0.1 g) under a nitrogen atmosphere, the mixture was degassed and exchanged with hydrogen for 3 times. The mixture was stirred at rt under 1 atm hydrogen atmosphere for 4 h. The mixture was filtered through a pad of celite and washed with EtOAc (2×10 mL). The combined filtrate and washing were concentrated under reduced pressure to give intermediate 42 (0.7 g), which was used for the next step without further purification. LC-MS (method 1): t$_R$=0.99 min, MS (ESI) m/z 503.2 [M+H]$^+$.

Step 3: Synthesis of Intermediate 43

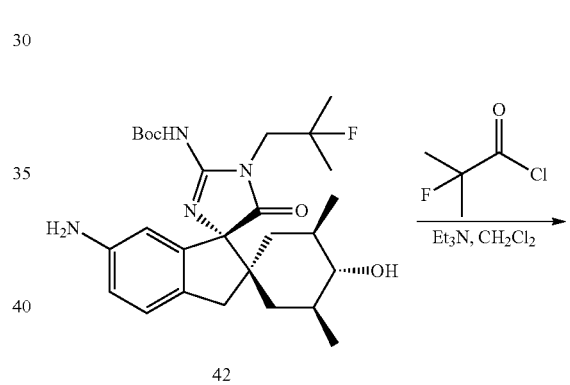

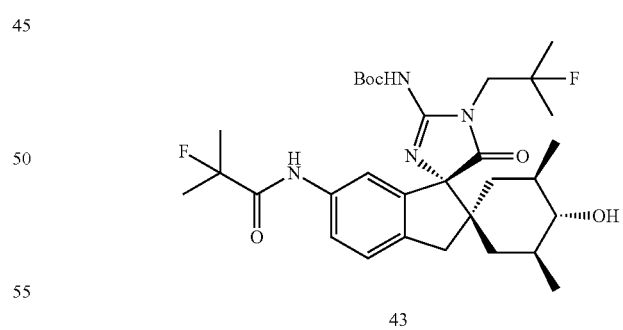

To a mixture of intermediate 42 (350 mg, 0.7 mmol) in DCM (5 mL) was added Et$_3$N (0.2 mL, 1.2 mmol, 2.0 eq) and 2-fluoro-2-methylpropanoyl chloride (150 mg, 2 mmol). The mixture was stirred at rt for 3 h. The reaction was quenched with water and extracted with DCM (2×10 mL). The combined organic layers were washed with brine (3×15 mL), dried over Na$_2$SO$_4$ and the solvent was removed under reduced pressure to afford crude intermediate 43 (320 mg) which was used for the next step without further purification.

Step 4: Synthesis of Example 6

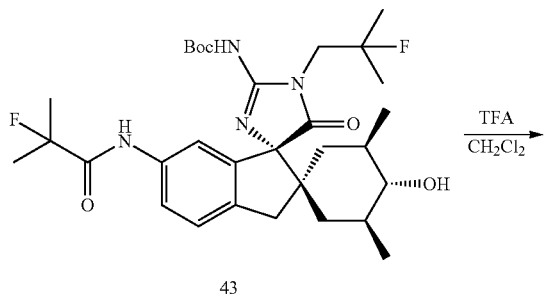

43

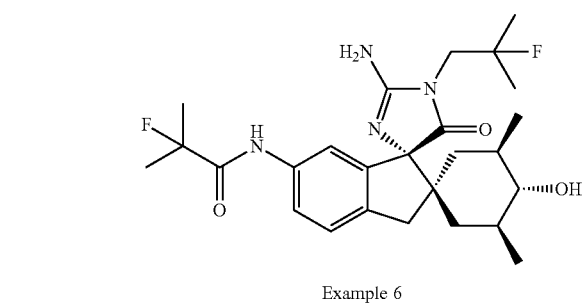

Example 6

To a mixture of intermediate 43 (320 mg, 0.54 mmol) in DCM (5 mL) TFA (1 mL) was added and the mixture was stirred at rt for 2 h. The reaction was quenched with sat. NaHCO₃ aqueous solution (10 mL). The mixture was partitioned between DCM (10 mL) and H₂O (10 mL). The organic layer was separated and washed with brine (10 mL), dried over Na₂SO₄, filtered and concentrated under reduced pressure. The residue was purified by preparative HPLC (basic method 1) to give Example 6 (179.9 mg).

LC-MS (method 1): LC-MS $t_R$=0.86 min, MS (ESI) m/z 491.2[M+H]⁺.

¹H NMR: (CD₃OD): δ 7.42 (m 1H), 7.30 (m, 2H), 3.78-3.71 (m, 2H), 3.17-3.05 (m, 2H), 2.59 (t, J=10.0 Hz, 1H), 1.80 (d, J=12.0 Hz, 1H), 1.64-1.53 (m, 8H), 1.42-1.34 (m, 8H), 1.08-0.96 (m, 7H).

¹⁹F NMR: (CD₃OD): δ-138.95, −147.61.

Example 7

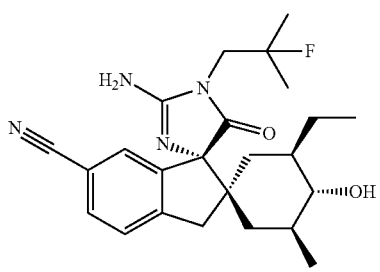 [SMILES: CC[C@@H]1C[C@@]2(Cc3ccc(C#N)cc3[C@]23N=C(N)N(CC(C)(C)F)C3=O)C[C@H](C)[C@H]1O]

Step 1: Synthesis of Intermediate 44

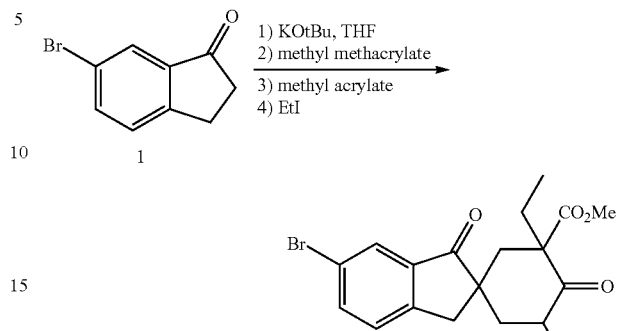

To a solution of 6-bromo-indan-1-one (100.0 g, 0.48 mol) dissolved in THF (2.0 L, 0.24 M) was added t-BuOK (64.0 g, 0.57 mol) in one portion at 0° C. The reaction was stirred for 5 min at 0° C. and stirred for an additional 10 min at rt. Methyl methacrylate (56.0 mL, 0.53 mol) was added in one portion. After 30 min, methyl acrylate (52.0 mL, 0.57 mol) was added in one portion and the mixture stirred overnight. To this reaction mixture, DMF (260 mL, 1.8 M) and EtI (76.0 mL, 0.96 mol) were added and the mixture was stirred overnight. The reaction was quenched with sat. aqueous citric acid solution (200 mL) and the organic layer was separated. The EtOAc was removed under reduced pressure and the crude material was diluted with H₂O (3 L) and extracted with EtOAc (3×3 L). The combined organic layers were washed with brine, dried over Na₂SO₄, filtered, and the solvent removed under reduced pressure to afford crude intermediate 44 (200 g), which was used for the next step without further purification.

Step 2: Synthesis of Intermediate 45

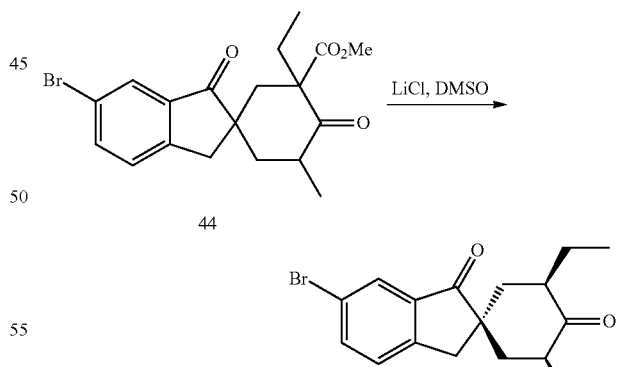

Intermediate 44 (200.0 g, 0.51 mol) was mixed with DMSO (1.0 L, 0.5 M) and LiCl (215.0 g, 5.1 mol) was added. The mixture was heated to 120° C. for 4 days. The mixture was concentrated in vacuo. The residue was dissolved in EtOAc, filtered, and the filtrate was concentrated. The residue was purified by column chromatography on silica gel (petroleum ether:EtOAc=30:1) to afford the crude intermediate.

The intermediate was dissolved in minimal amount of MeOH, and NaOMe in MeOH (30%, 20 mL) was added. After 20 min, the mixture was filtered to give intermediate 45 (40 g).

¹H NMR: (CDCl₃): δ 7.93 (d, J=1.6 Hz, 1H), 7.77 (dd, J=10.8, 2.4 Hz, 1H), 7.42-7.45 (d, J=10.8 Hz, 1H), 3.34 (s, 2H), 2.60-2.70 (m, 1H), 2.36-2.47 (m, 1H), 1.76-1.99 (m, 5H), 1.21-1.30 (m, 1H), 1.07 (d, J=8.8 Hz, 3H), 0.90 (t, J=9.6 Hz, 3H) ppm.

Step 3: Synthesis of Intermediate 46

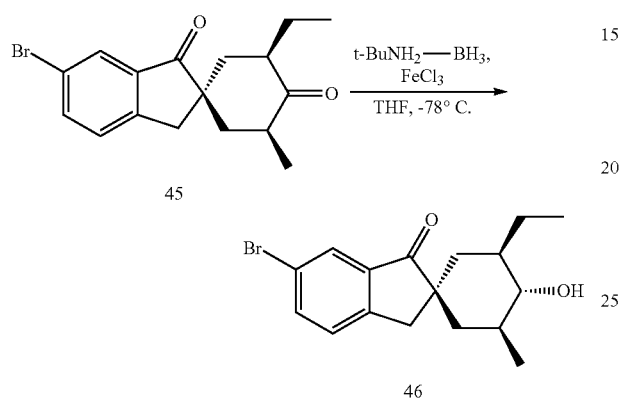

Intermediate 46 was synthesized from intermediate 45 by a method similar to that described in step 2 of Example 1.

¹H NMR: (CDCl₃): δ 7.81 (d, J=1.8 Hz, 1H), 7.63 (dd, J=8.1, 2.1 Hz, 1H), 7.42-7.45 (d, J=8.4 Hz, 1H), 3.34 (s, 2H), 2.60-2.70 (m, 1H), 2.36-2.47 (m, 1H), 1.76-1.99 (m, 5H), 1.21-1.30 (m, 1H), 1.07 (d, J=7.2 Hz, 3H), 0.90 (t, J=7.5 Hz, 3H) ppm.

Step 4: Synthesis of Intermediate 47

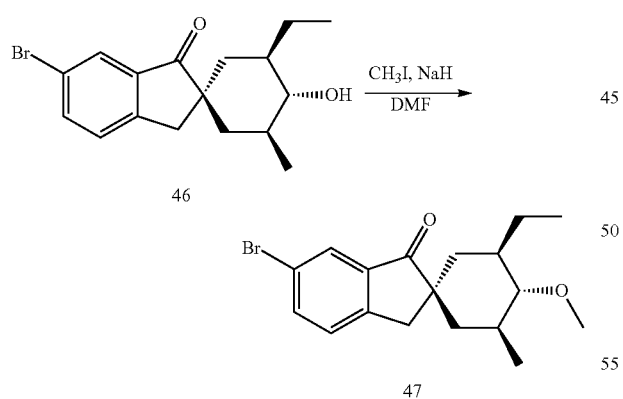

To a solution of intermediate 46 (30.0 g, 0.08 mol) in DMF (500 mL) was added NaH (8.0 g, 0.16 mol) at 0° C. The mixture was stirred at 0° C. 30 min, and then MeI (25.0 mL, 0.4 mol) was added and the mixture was stirred at rt overnight. The mixture was quenched with H₂O (100 mL), extracted with EtOAc (3×300 mL). The organic layer was concentrated and purified by column chromatography (petroleum ether/EtOAc=20/1) to afford intermediate 47 (22.0 g).

¹H NMR: (CDCl₃): δ 7.81 (d, J=1.8 Hz, 1H), 7.63 (m, J=8.1, 1.8 Hz, 1H), 7.27 (d, J=8.1 Hz, 1H), 3.41 (s, 3H), 2.91 (s, 2H), 2.46-2.52 (m, 1H), 1.75-1.79 (m, 1H), 1.59-1.62 (m, 1H), 1.29-1.47 (m, 5H), 1.08-1.15 (m, 1H), 0.98 (d, J=6.3 Hz, 3H), 0.78 (t, J=7.5 Hz, 3H).

Step 5: Synthesis of Intermediate 48

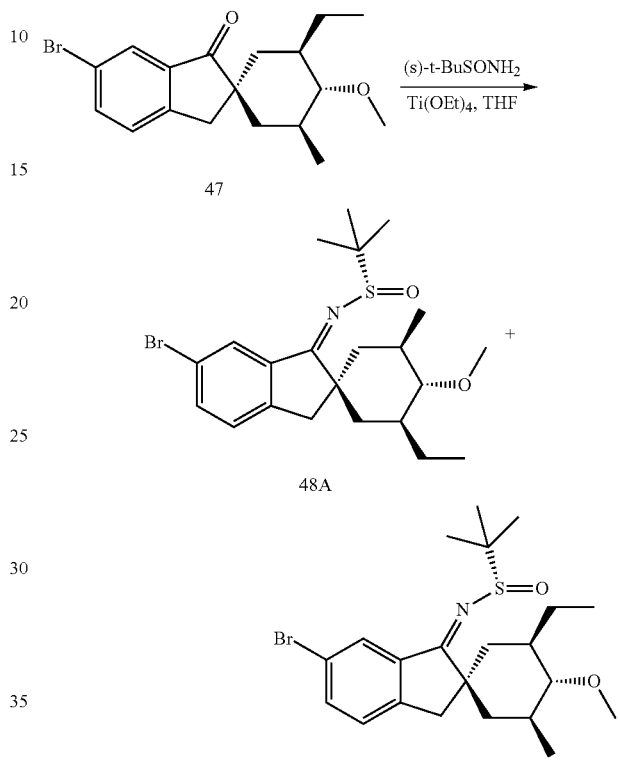

A mixture of intermediate 47 (22.0 g, 0.06 mol) and titanium (IV) ethoxide (130 mL, 0.62 mol) in dry THF (400 mL) was stirred at rt for 1 h. (S)—N-tert-butylsulfinamide (30.0 g, 0.25 mol) was added and the resulting mixture was stirred at 80° C. under N₂ overnight. The reaction mixture was cooled and water (200 ml) was added. The mixture was filtered and the aqueous layer was extracted with EtOAc (3×400 mL). The combined organic layer was dried over Na₂SO₄ and concentrated under reduced pressure. The residue was purified by column chromatography on silica gel (petroleum ether:EtOAc=20:1) to give intermediate 48A (7.0 g) and 48 (10.0 g) respectively.

Step 6: Synthesis of Intermediate 49

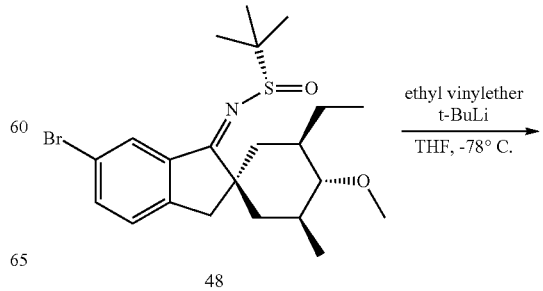

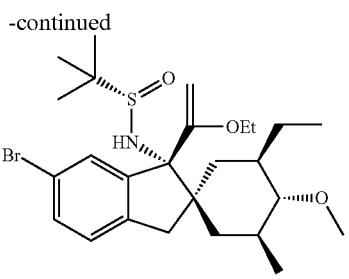

To a mixture of ethoxy-ethene (4.7 mL, 49.5 mmol) in anhydrous THF (50 mL) at −78° C. was added t-BuLi (38.0 mL, 49.5 mmol, 1.3 M in hexane) dropwise over 20 minutes and the mixture was stirred for 20 min. The resulting mixture was stirred at 0° C. for another 45 min and then cooled back to −78° C.

A pre-cooled solution of intermediate 48 (4.5 g, 9.9 mmol) in anhydrous THF (60 mL) at −78° C. was added to the above solution, dropwise over 30 minutes and the mixture was stirred for 2.5 h at −78° C. The reaction was quenched with sat. NH$_4$Cl (50 mL) and extracted with EtOAc (3×100 mL). The combined organic phase was concentrated under reduced pressure to give the residue, which was purified by column chromatography (petroleum ether:EtOAc=20:1) to afford intermediate 49 (3.5 g).

LC-MS (method 1): t$_R$=5.94 min, MS (ESI) m/z 528.1 [M+H]$^+$.

Step 7: Synthesis of Intermediate 50

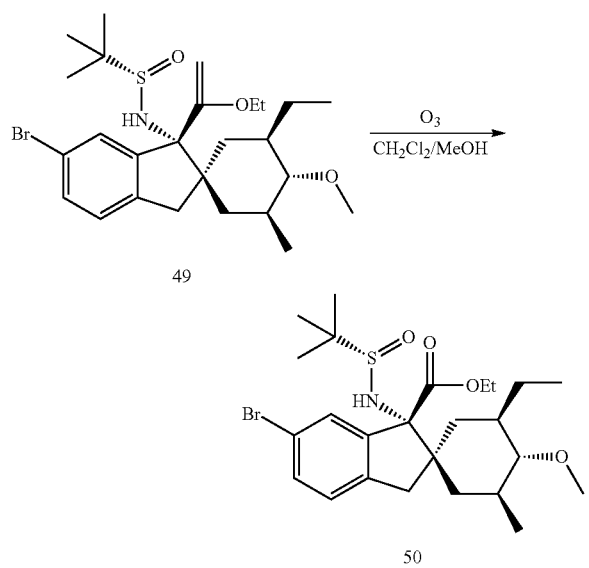

Intermediate 49 (3.5 g, 6.60 mmol) was dissolved in a mixture of DCM and MeOH (5:1; 40 mL), and cooled to −78° C. Ozone was bubbled through the mixture for 20 min. The reaction was stirred for an additional 10 minutes, after which the mixture was purged with N$_2$ and treated with Me$_2$S at −78° C. The reaction was allowed to warm to rt and stirred for an additional 3 h. The solvent was removed under reduced pressure and the residue was purified by column chromatography on silica gel (petroleum/EtOAc=15/1) to give intermediate 50 (2.3 g).

$^1$H NMR: (CDCl$_3$): δ 7.83 (s, 1H), 7.43 (dd, J=8.0, 2.0 Hz, 1H), 7.10 (d, J=8.0 Hz, 2H), 4.26-4.43 (m, 3H), 3.42 (s, 3H), 2.95 (d, J=16.0 Hz, 1H), 2.68 (d, J=16.0 Hz, 1H), 2.32-2.37 (m, 1H), 2.17 (s, 1H), 1.91-1.97 (m, 1H), 1.82-1.89 (m, 1H), 1.63-1.68 (m, 1H), 1.31-1.40 (m, 6H), 1.13 (s, 9H), 0.90-0.95 (m, 6H), 0.68 (t, J=12.0 Hz, 1H).

Step 8: Synthesis of Intermediate 51

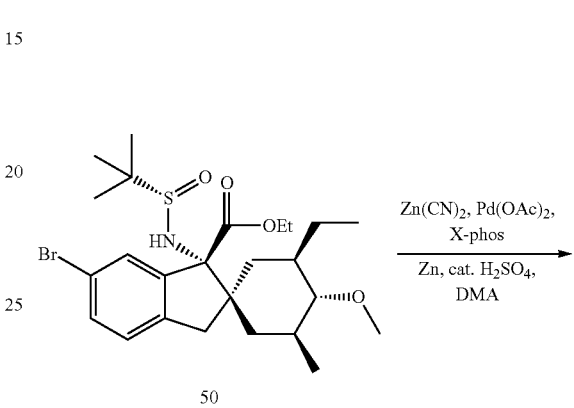

Concentrated sulfuric acid (49 μL), was added to DMA (20 mL) and the solvent was purged with N$_2$ for 20 min A 50 mL round bottom flask was charged with Pd (OAc)$_2$ (1.35 g) and Xphos (3.15 g) under N$_2$, and transferred to the above solution. The resulting mixture was heated at 80° C. for 30 min to give mixture A.

In an another flask, DMA (30 mL) was purged under N$_2$ for 20 min and intermediate 50 (2.3 g, 4.50 mmol), Zn (CN)$_2$ (527 mg, 4.50 mmol) and Zn dust (15 mg) were added followed by mixture A. The resulting mixture was heated at 90° C. for 40 min. The reaction mixture was cooled to rt, diluted with water (80 mL) and EtOAc (100 mL). After stirring for 10 minutes, the mixture was filtered through celite, and the organic layer was separated. The aqueous layer was extracted with EtOAc (3×100 mL). The combined organic layers were washed with water, brine, dried over Na$_2$SO$_4$, and the solvent was removed under reduced pressure. The residue was purified by column chromatography on silica gel (petroleum:EtOAc=10:1) to afford intermediate 51 (1.8 g).

LC-MS (method 1): t$_R$=1.19 min, MS (ESI) m/z 475.2 [M+H]$^+$.

Step 9: Synthesis of Intermediate 52

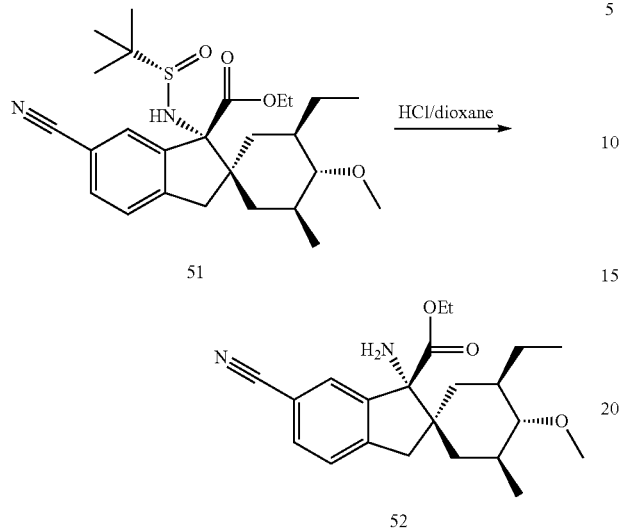

To a mixture of intermediate 51 (590 mg, 1.24 mmol) in MeOH (10 mL) was added a 4 M HCl solution in dioxane (2 mL). The resulting mixture was stirred for 30 min. Solvent was removed under reduced pressure to afford crude intermediate 52 (550 mg), which was used for the next step without further purification.

LC-MS (method 1): $t_R$=0.88 min, MS (ESI) m/z 322.1 [M−48]$^+$.

Step 10: Synthesis of Intermediate 53

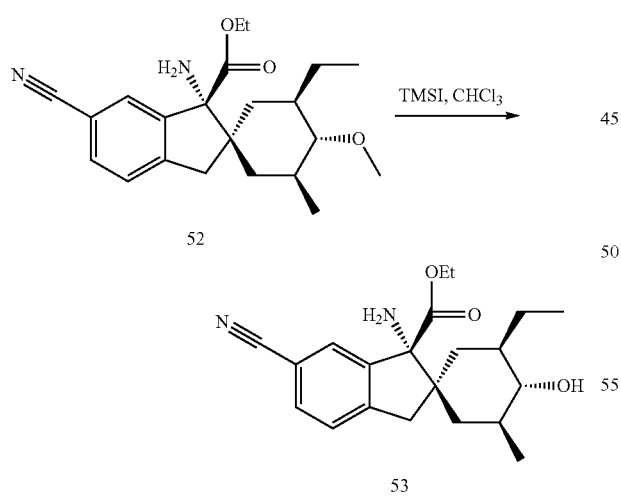

To a mixture of intermediate 52 (550 mg, 1.59 mmol) in CHCl$_3$ (10 mL) was added TMSI (2.5 mL, 15.9 mmol) slowly at rt. The mixture was stirred at 60° C. for 2 h and then allowed to cool to rt. MeOH (5 mL) and sat. Na$_2$S$_2$O$_3$ (5 mL) solution was added over 10 minutes. The layers were separated and the aqueous layer was extracted with CH$_2$Cl$_2$ (3×40 mL). The organic layers were combined, washed with water (2×40 mL), dried and solvent was removed under reduced pressure to yield crude intermediate 53 (400 mg).

Step 11: Synthesis of Intermediate 54

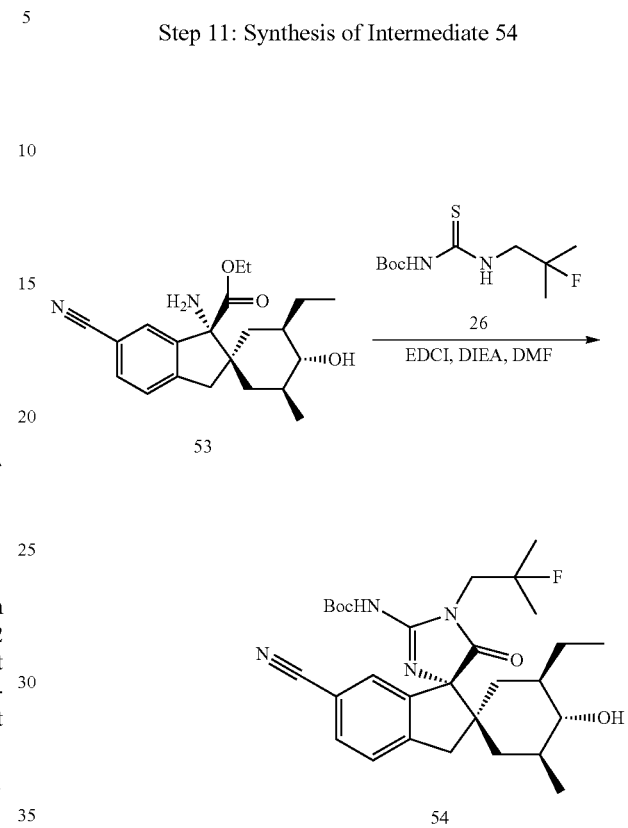

To a mixture of intermediate 53 (1.2 g, 3.30 mmol) in DMF (15 mL), intermediate 26 (850 mg, 3.30 mmol), EDCI (1.28 g, 6.60 mmol) and DIEA (1.2 mL, 6.60 mmol) were added. The mixture was stirred at 30° C. overnight. The solution was cooled to rt and EtOAc (20 mL) and water (20 mL) were added. The organic layer was separated and the aqueous layer was extracted with EtOAc (3×60 mL). The combined organic layers were washed with brine (3×50 mL), dried and the solvent was removed under reduced pressure. The residue was purified by column chromatography on silica gel (petroleum ether/EtOAc=5/1) to afford 54 (760 mg).

Step 12: Synthesis of Example 7

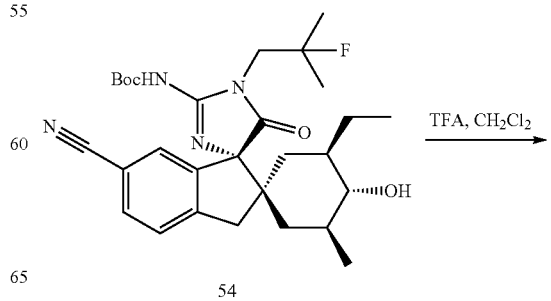

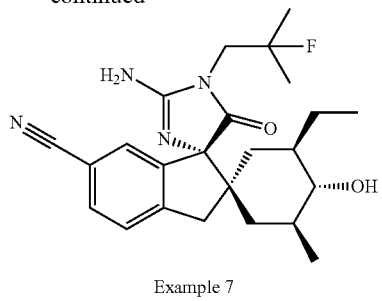

Example 7

To a mixture of intermediate 54 (750 mg, 1.43 mmol) in DCM (8 mL) was added TFA (2 mL) and stirred at rt for 1 h. The pH of the reaction mixture was adjusted to 8.5 by addition of sat. NaHCO₃ solution. The organic layer was separated and concentrated under reduced pressure to yield crude product. The residue was purified by preparative HPLC (basic, method 2) to give Example 7 (465 mg).

LC-MS (method 1): $t_R$=0.85 min, MS (ESI) m/z 427.2 [M+H]⁺.

¹H-NMR: (CD₃OD): 7.65 (dd, J=8.0, 1.6 Hz, 1H), 7.49 (d, J=8.0 Hz, 1H), 7.30 (s, 1H), 3.65-3.80 (m, 2H), 3.12-3.29 (m, 2H), 2.64-2.69 (m, 1H), 1.79-1.84 (m, 2H), 1.51-1.55 (m, 1H), 1.32-1.50 (m, 9H), 1.32-1.42 (m, 1H), 1.00-1.20 (m, 4H), 0.78 (t, J=7.6 Hz, 3H).

¹⁹F-NMR: (CD₃OD): −139.444.

Example 8

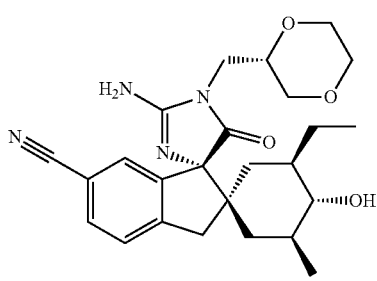 [SMILES: CC[C@@H]1C[C@@]2(Cc3ccc(C#N)cc3[C@]23N=C(N)N(C[C@H]2COCCO2)C3=O)C[C@H](C)[C@H]1O]

Step 1: Synthesis of Intermediate 56

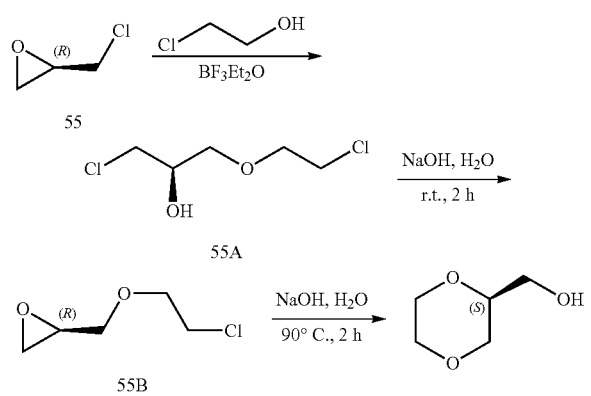

A mixture of (R)-2-(chloromethyl)oxirane (55, 109 mL, 1.62 mol) and BF₃.OEt₂ (3.4 mL, 0.027 mol) in toluene (200 mL) was heated to an internal temperature of 30° C. and 2-choloroethanol (49 g, 0.53 mol) was added dropwise at a rate sufficient to main the reaction temperature at 36-38° C. The resulting mixture was aged at 36° C. for 20 min. The mixture was cooled to 16° C. and aqueous NaOH (250 mL, 23%) was added with vigorous stirring over 1 h, maintaining the reaction temperature below 20° C. The mixture was aged for 1 h at rt. The two layers were separated, and the aqueous phase was extracted with toluene (130 mL). The combined organic layers were washed with water (100 mL), the resulting organic layer was distilled to low volume, monitoring the distillate for loss of product to give the final intermediate 56 (23 g).

¹H-NMR: (CDCl₃): δ 3.33-3.84 (m, 9H).

Step 2: Synthesis of Intermediate 57

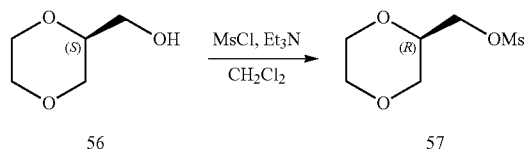

To a mixture of intermediate 56 (81.0 g, 0.686 mol) in DCM (500 mL) was added TEA (196 mL, 1.37 mol) and MsCl (80 mL, 1.029 mol) at 0° C. The mixture was stirred for 5 h at rt, and quenched with water (200 mL), extracted with dichloromethane (2×200 mL). The combined organic layer was washed with brine, dried over Na₂SO₄ and concentrated to afford crude intermediate 57 (132.8 g), which was used for the next step directly without purification.

Step 3: Synthesis of Intermediate 58

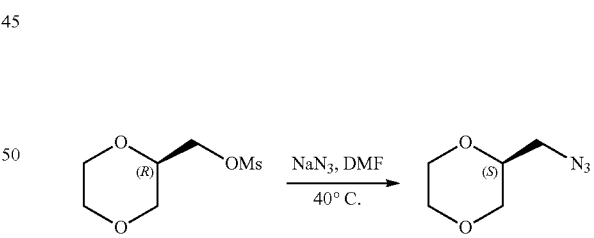

To a mixture of intermediate 57 (132.8 g, 0.677 mol) in DMF (640 mL), NaN₃ (88.0 g, 1.35 mol), NaHCO₃ (170.6 g, 2.03 mol) and NaI (20.3 g, 0.135 mol) were added. The mixture was stirred at rt overnight. The reaction mixture was quenched with water (300 mL), and then extracted with ethyl acetate (2×300 mL). The combined organic layer was washed with water and then brine, dried over Na₂SO₄ and concentrated under reduced pressure to afford crude intermediate 58 (96 g), which was used for the next step directly without purification.

Step 4: Synthesis of Intermediate 59

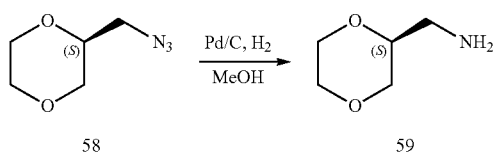

To a mixture of intermediate 58 (3.6 g, 25.48 mmol) in MeOH (100 mL) was added Pd/C (0.4 g, 10% content) under a nitrogen atmosphere, the mixture was degassed and exchanged with hydrogen for 3 times. The final mixture was stirred at rt under hydrogen balloon for 24 h. The catalyst was filtered off through a pad of celite and washed with MeOH (2×50 mL). The combined filtrate and washing were concentrated under reduced pressure to give crude intermediate 59 (2.93 g).

Step 5: Synthesis of Intermediate 60

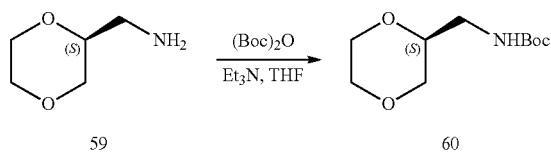

To a solution of intermediate 59 (1.1 g, 10 mmol) in THF (50 mL) was added Et$_3$N (3.0 g, 30 mmol) and (Boc)$_2$O (2.6 g, 12 mmol). The mixture was stirred at rt overnight. The reaction was quenched with water (20 mL) and extracted with EtOAc (2×30 mL). The combined organic layer was washed with brine (20 mL), dried over Na$_2$SO$_4$, filtered and concentrated under vacuum to give crude product, which was purified by column chromatography on silica gel (petroleum ether: ethyl acetate; 100:1 to 20:1) to afford pure intermediate 60 (500 mg).

Step 6: Synthesis of Intermediate 61

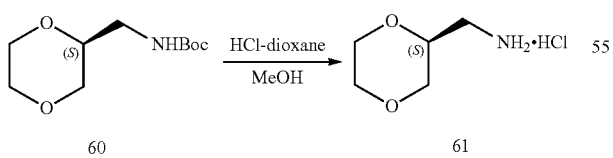

Intermediate 60 (20 g, 92 mmol) was dissolved in MeOH (150 mL), and then a solution of HCl in dioxane (4 M, 30 mL, 120 mmol,) was added. The reaction mixture was stirred at rt for 18 h. MeOH was removed under vacuum to yield pure intermediate 61 (14 g), which was used for the next step without further purification.

$^1$H NMR (CD$_3$OD): δ 3.62-3.90 (m, 6H), 3.32-3.35 (m, 1H), 3.01-3.04 (m, 1H), 2.85-2.90 (m, 1H).

Step 7: Synthesis of Intermediate 62

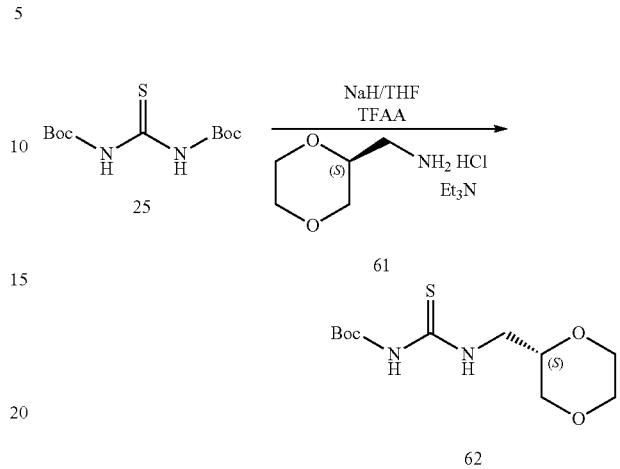

To a mixture of intermediate 25 (12.3 g, 44.55 mmol) in anhydrous THF (600 mL) was added NaH (2.1 g, 53.46 mmol, 60% in mineral oil) at 0° C. The reaction mixture was stirred for 1 h, followed by addition of TFAA (6.9 mL, 49.0 mmol) and the stirring was continued for additional 1 h. Intermediate 61 (7.5 g, 49.0 mmol) and Et$_3$N (12.4 mL, 89.1 mmol) in anhydrous THF (300 mL) were added and the resulting reaction mixture was stirred at rt overnight. H$_2$O (300 mL) was added to quench the reaction and the mixture was extracted with EtOAc (3×350 mL). The combined organic layers were dried, filtered and the solvent was removed under reduced pressure. The residue was purified by column chromatography on silica gel (5-50% ethyl acetate in hexane) to afford intermediate 62 (7.95 g).

LCMS (method 1): t$_R$=0.90 min, MS (ESI) m/z 221.1 [M−55]$^+$.

$^1$H NMR (CD$_3$OD): δ 3.80-3.90 (m, 4H), 3.70-3.80 (m, 2H), 3.55-3.65 (m 2H), 3.35-3.40 (m, 1H), 1.57 (s, 9H).

Example 8 was synthesized from intermediate 53 and intermediate 62 in accordance with the method described in steps 11 and 12 for Example 7.

LC-MS (method 1): t$_R$=0.87 min, MS (ESI) m/z 453.2[M+H]$^+$.

$^1$H NMR (CD$_3$OD): 7.64 (dd, J=8.0, 1.2 Hz, 1H), 7.49 (d, J=7.6 Hz, 1H), 7.30 (s, 1H), 3.51-3.86 (m, 8H), 3.11-3.35 (m, 3H), 2.64-2.69 (m, 1H), 1.78-1.84 (m, 2H), 1.49-1.55 (m, 1H), 1.39 (s, 3H), 1.13-1.20 (m, 1H), 0.99-1.06 (m, 4H), 0.78 (t, J=7.6 Hz, 3H).

Example 9

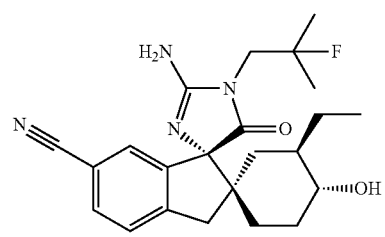 [SMILES: CC[C@@H]1C[C@]2(CC[C@H]1O)Cc1ccc(C#N)cc1[C@]21N=C(N)N(CC(C)(C)F)C1=O]

Step 1: Synthesis of Intermediate 62

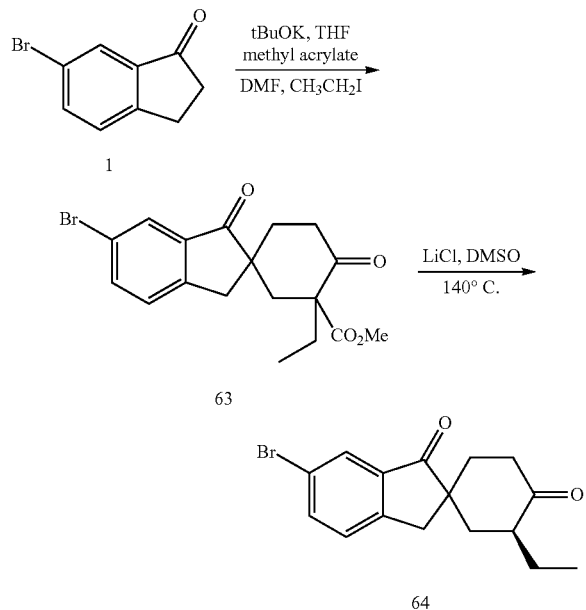

A mixture of 6-bromo-indan-1-one 1 (50.0 g, 236 mmol) and methyl acrylate (42.0 g, 472 mmol) in anhydrous THF (900 mL) was pre-cooled to 0° C. and t-BuOK (31.8 g, 284 mmol, 1.1 eq) was added portion wise over 30 min. The mixture was warmed to rt over 1 h and stirred for an additional 40 min at rt. DMF (200 mL) and EtI (74 g, 472 mmol) were added to this reaction mixture, and the mixture was stirred at rt overnight. THF was removed under reduced pressure. The residue was diluted with H$_2$O (300 mL) and extracted with EtOAc (300 mL). The organic layer was concentrated under reduced pressure to afford the crude intermediate 63 (120.0 g). This product was used as is for the next step.

A mixture of intermediate 63 (120.0 g, 310 mmol) and LiCl (130.0 g, 3100 mmol) in DMSO (900 mL) was refluxed overnight. The mixture was quenched with water (3 L) and extracted with EtOAc (3×400 mL). The combined organic phase was dried and concentrated under reduced pressure. The residue was purified by column chromatography on silica gel (petroleum ether: EtOAc; 20:1) to give intermediate 64 (15 g).

$^1$H NMR: (CDCl$_3$): δ 7.91 (s, 1H), 7.74 (dd, J=8.0 Hz, 1H), 7.41 (d, J=8.0 Hz, 1H), 3.80 (s, 2H), 2.48-2.53 (m, 2H), 2.33-2.49 (m, 1H), 2.15-2.23 (m, 1H), 1.75-1.95 (m, 4H), 1.21-1.40 (m, 1H), 0.88 (t, J=8.0 Hz, 3H).

Step 2: Synthesis of Intermediate 66

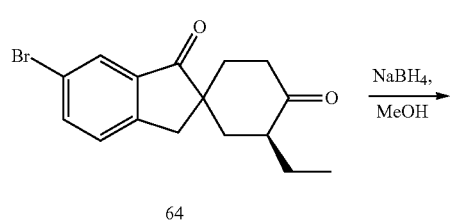

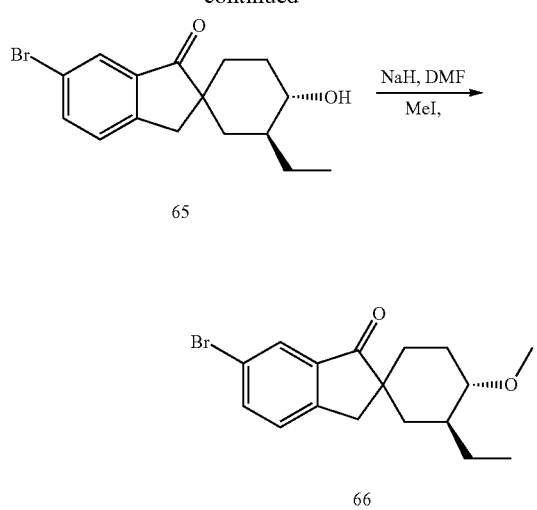

To a mixture of THF (20 mL) and MeOH (5 mL) at −78° C. was added intermediate 64 (6.0 g, 18.7 mmol), NaBH$_4$ (355 mg, 9.3 mmol) and CeCl$_3$.7H$_2$O (70 mg, 0.19 mmol). The mixture was stirred at −78° C. for 20 min, quenched with satd. NH$_4$Cl solution (30 mL), and extracted with EtOAc (400 mL×4). The organic layers were combined and concentrated under reduced pressure to afford a crude intermediate 65 (6.5 g).

To a mixture of intermediate 65 (6.5 g, 20.0 mmol) and NaH (3.2 g, 80.0 mmol) in DMF (100 mL) was added MeI (11.4 g, 80.0 mmol) at 0° C. The mixture was stirred at rt overnight. The mixture was quenched with H$_2$O, extracted with EtOAc, and concentrated under reduced pressure to afford the crude product, which was purified by column chromatography on silica gel (eluent:petroleum ether:ethyl acetate; 20:1 to 15:1) to afford intermediate 66 (3.5 g).

LC-MS (method 1): t$_R$=1.32 min, MS (ESI) m/z 339.1 [M+H]$^+$.

$^1$H NMR: (CDCl$_3$): δ 7.88 (s, 1H), 7.69 (dd, J=8.4, 2.0 Hz, 1H), 7.31 (d, J=8.4 Hz, 1H), 3.39 (s, 3H), 2.97 (s, 2H), 2.88-2.94 (m, 1H), 2.21-2.26 (m, 1H), 1.81-1.87 (m, 1H), 1.70-1.78 (m, 1H), 1.40-1.59 (m, 4H), 1.12-1.39 (m, 2H), 0.88 (t, J=8.0 Hz, 3H).

Step 3: Synthesis of Intermediate 67 & 67A

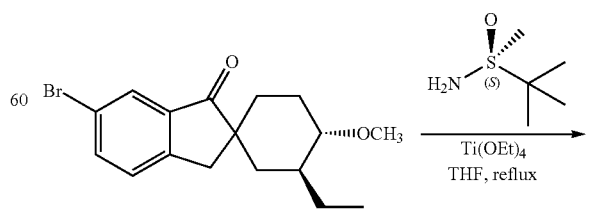

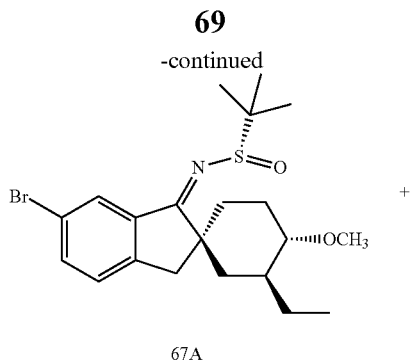

67A

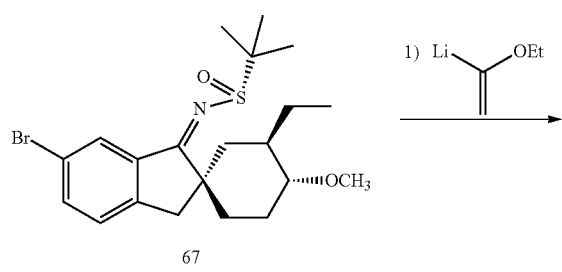

67

The mixture of intermediate 66 (3.5 g, 10.4 mmol) and titanium (IV) ethoxide (23.7 g, 104 mmol) in dry THF (40 mL) was stirred at rt for 1 hour. (S)—N-tert-butylsulfinamide (1.6 g, 11.6 mmol) was added and the resulting mixture was stirred at 80° C. under $N_2$ atmosphere overnight. The reaction mixture was cooled and water (400 mL) was added and filtered. The aqueous layer was extracted with EtOAc (3×200 mL). The separated organic phases were combined and dried and concentrated under reduced pressure. The residue was purified by column chromatography on silica gel (petroleum ether:EtOAc; 20:1) and compounds eluted in the following order to give intermediate 67A (1.5 g) and 67 (1.5 g) respectively.

Step 4: Synthesis of Intermediate 68

C. for an additional 45 min and then cooled back to −78° C. To this mixture, a pre-cooled solution of intermediate 67 (1.5 g, 3.4 mmol) in anhydrous THF (20 mL) at −78° C. was added dropwise and stirred for 2.5 h. The reaction was quenched with sat. $NH_4Cl$ (50 mL) and then extracted with EtOAc (3×100 mL). The organic phases were combined and concentrated under reduced pressure to afford the crude product, which was purified by column on silica gel (petroleum ether: ethyl acetate; 20:1) to afford intermediate 68 (1.2 g).

Step 5: Synthesis of Intermediate 69

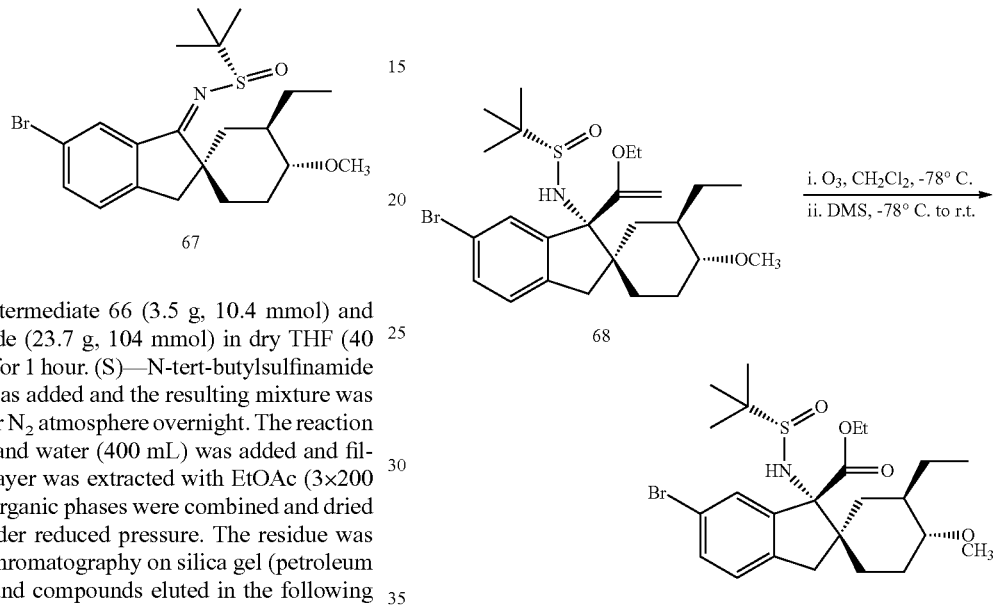

68

69

The intermediate 68 (1.2 g, 2.4 mmol) was added to a mixture of methanol in DCM (5:1, 20 mL), and cooled to −78° C. Ozone was bubbled through the mixture for 20 min. The mixture was purged with $N_2$ and treated with $Me_2S$ (5 mL) at −78° C. The reaction was allowed to warm to rt and stirred for an additional 3 h. The solvent was removed under vacuum, the residue was purified by preparative TLC (petroleum ether: ethyl acetate; 3:1) to afford intermediate 69 (860 mg).

LC-MS (method 1): $t_R$=1.35 min, MS (ESI) m/z 516.1 $[M+H]^+$.

Step 6: Synthesis of Intermediate 70

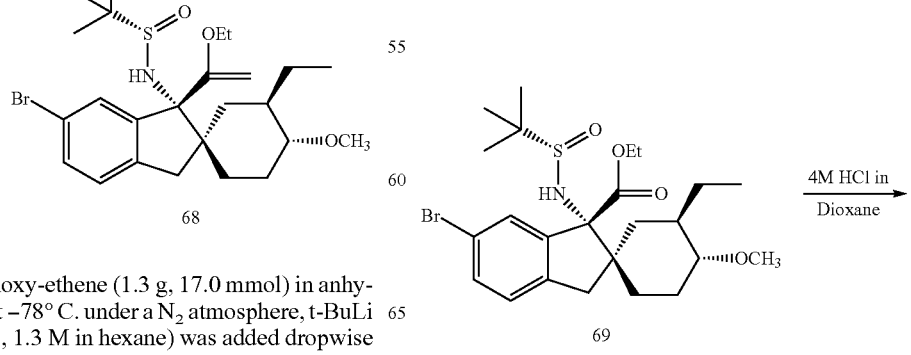

69

To a mixture of ethoxy-ethene (1.3 g, 17.0 mmol) in anhydrous THF (20 mL) at −78° C. under a $N_2$ atmosphere, t-BuLi (13.0 mL, 17.0 mmol, 1.3 M in hexane) was added dropwise and stirred for 20 min. The resulting mixture was stirred at 0°

-continued

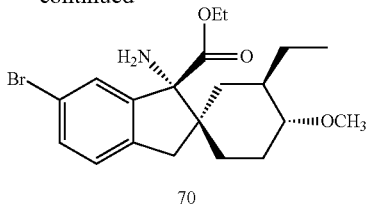

To intermediate 69 (860 mg, 1.7 mmol) in MeOH (10 mL) was added HCl in dioxane (4 M, 2 mL). The resulting mixture was stirred for 30 min at rt. The solvent was removed under reduced pressure to afford crude intermediate 70 (800 mg) which was used for the next step without further purification.

Example 9 was synthesized from intermediate 70 by the method described in Example 7, from step 10 through step 12.

LC-MS (method 1): $t_R$=0.79 min, MS (ESI) m/z 413.2 [M+H]$^+$.

$^1$H-NMR (CD$_3$OD): 7.66 (dd, J=7.6, 1.6 Hz, 1H), 7.51 (d, J=8.0 Hz, 1H), 7.32 (s, 1H), 3.69-3.76 (m, 2H), 3.12-3.27 (m, 3H), 1.78-1.95 (m, 3H), 1.32-1.42 (m, 11H), 1.11-1.18 (m, 1H), 0.78 (t, J=7.6 Hz, 3H).

$^{19}$F-NMR (CD$_3$OD): −139.768.

Example 10

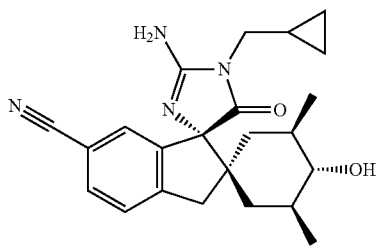 [SMILES: C[C@@H]1C[C@@]2(Cc3ccc(C#N)cc3[C@]23N=C(N)N(CC2CC2)C3=O)C[C@H](C)[C@H]1O]

Example 10 was prepared by the method described in Example 1, using cyclopropyl methyl amine in step 10.

LC-MS (method 1): $t_R$=1.02 min; =393.

$^1$HNMR (CD$_3$OD) δ (ppm): 7.62 (dd, J=8.0, 2.0 Hz, 1H), 7.47 (d, J=8.0 Hz, 1H), 7.26 (d, J=2.0 Hz, 1H), 3.47 (dd, J=14.8, 6.4 Hz, 1H), 3.34 (dd, J=14.8, 6.4 Hz, 1H), 3.24 (d, J=16.0 Hz, 1H), 3.12 (d, J=16.0 Hz, 1H), 2.54 (t, J=10.0 Hz, 1H), 1.79, (d, J=12.4 Hz, 1H), 1.60-1.40 (m, 3H), 1.22 (m, 2H), 1.03 (m, 1H), 0.99 (d, J=6.4 Hz, 3H), 0.94 (d, J=6.0 Hz, 3H), 0.49 (m, 2H), 0.32 (m, 2H).

Example 11

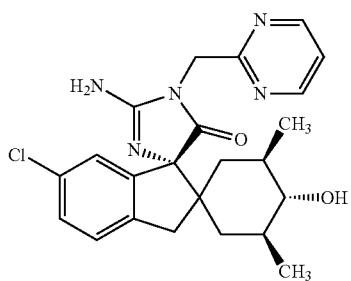 [SMILES: C[C@@H]1CC2(Cc3ccc(Cl)cc3[C@]23N=C(N)N(Cc2ncccn2)C3=O)C[C@H](C)[C@H]1O]

Example 11 was prepared by the method described in Example 1, using 6-chloro indan-1-one in the first step and 2-aminomethylpyrimidine in step 10.

LC-MS (method 1) $t_R$=0.90 min m/z 440, 442 (MH$^+$)

$^1$H NMR (CD$_3$OD) δ 8.73 (d, J=4.7 Hz, 2H), 7.38 (t, J=4.7 Hz, 1H), 7.27-7.24 (m, 2H), 5.01 (s, 2H), 3.14-3.05 (m, 2H), 2.60 (t, J=9.8 Hz, 1H), 1.77-1.74 (m, 1H), 1.67-1.58 (m, 1H), 1.55-1.45 (m, 1H), 1.40-1.24 (m, 3H), 1.01-0.97 (m, 6H).

Example 12

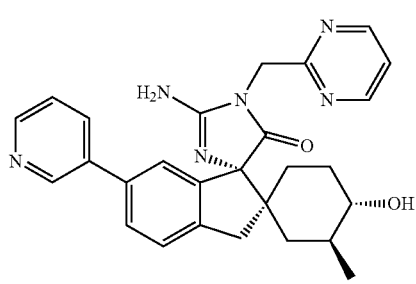

Step 1: Synthesis of Intermediate 71

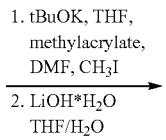

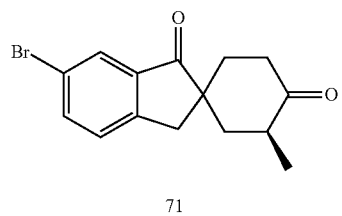

6-bromo-indan-1-one 1 (100 g, 474 mmol) and methyl acrylate (86.4 g, 995 mmol) were mixed with 800 mL THF and t-BuOK (1.0 g) was added in two portions under ice cooling. The cooling bath was removed and the remaining t-BuOK (63.0 g) was added in even portions over 20 min (total of 64.0 g, 569 mmol). The mixture was stirred for 2 h at rt. DMF (240 mL) was added to the reaction mixture, followed by MeI (135 g, 948 mmol) and the mixture was stirred for 2 h. The reaction was quenched with 10% citric acid solution. The reaction mixture was concentrated under reduced pressure and filtered. The cake was washed with water, followed by MeOH to give a crude intermediate which was mixed with THF/H$_2$O (1.8 L/1.8 L). LiOH*H$_2$O (92.0 g, 2.19 mol) was added. The mixture was stirred for 16 h at rt and then 12 h at 70° C. The reaction mixture was concentrated under reduced procedure and filtered. The cake was washed with H$_2$O, and then it was stirred with MeOH (50 mL) for 5 min, filtered again, and washed with additional amount of MeOH (50 mL). The solid was collected to give 75 g intermediate 71 which was used as such in the next step.

Step 2: Synthesis of Intermediate 72

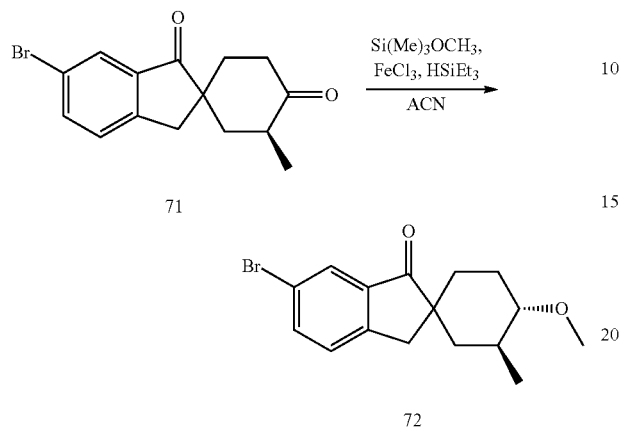

10.0 g (32.5 mmol) of intermediate 71 and 530 mg (3.27 mmol) ferric chloride were mixed with of 200 ml THF. To the stirred mixture 14.0 mL (102 mmol) methoxy trimethylsilane and 16.0 mL (100 mmol) triethylsilane were added and the mixture was stirred for 35 min at ambient temperature. The mixture was added to phosphate buffer (pH 7) and stirred for 14 h. The mixture was extracted with ethyl acetate, the organic phase dried and evaporated. The residue was purified by MPLC (340 g silica, cyclohexanes/ethyl acetate (100/0 to 85/15 in 60 min). Fractions containing the product were combined and the solvent was evaporated to yield 3.69 g of intermediate 72.

LC-MS (method 2): $t_R$=1.53 min. m/z 323/5 Br (M+H$^+$)

$^1$HNMR (DMSO-d6) corresponds with the desired product.

Step 3: Synthesis of Intermediate 73

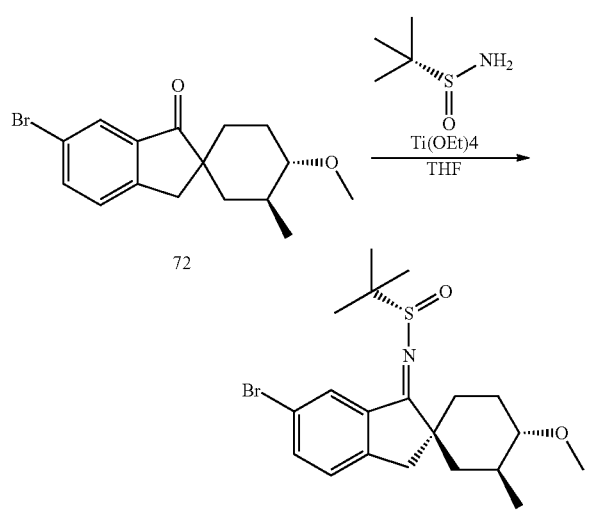

16.0 g (49.5 mmol) of intermediate 72 were mixed with 100 mL THF, 57.0 g (249 mmol) titanium (IV)-ethoxide were added and the mixture was stirred for 1 h at ambient temperature. After this, 12.0 g (99.0 mmol) of (S)-2-methyl-2-propanesulfinamide were added and mixture was refluxed under nitrogen for 3 days. 200 mL of water and 200 mL of DCM were added and the mixture filtered through celite. The organic layer was separated, and the solvent removed under vacuum. The residue was purified by MPLC (600 g silica, cyclohexanes/ethyl acetate (100/0 to 75/25 in 3 h, 95/5 to 85/15 in 15 min, 0/100 for 10 min). Fractions containing the product were combined. Mixed fractions were again chromatographed by MPLC. The desired product eluted first. The solvent was evaporated to yield 3.69 g of intermediate 73.

LC-MS (method 2): $t_R$=1.61 min m/z 426/8 Br (M+H$^+$)

$^1$HNMR (DMSO-d6) corresponds with the desired product.

Step 4: Synthesis of Intermediate 74

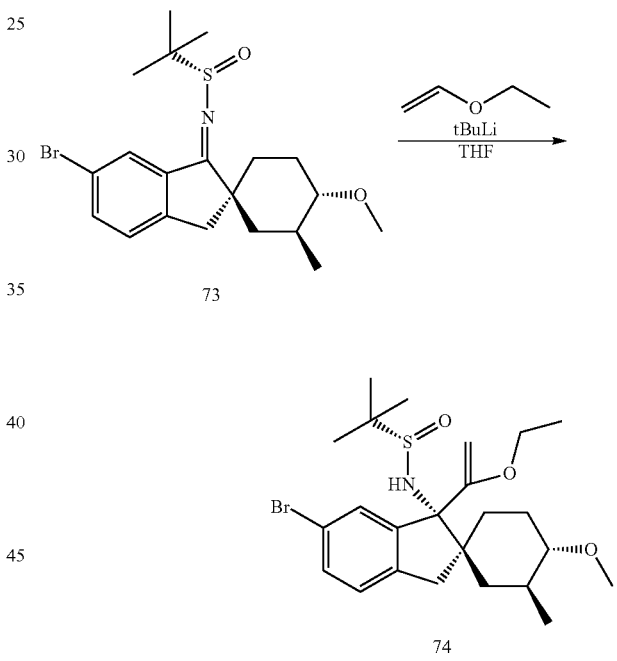

Under nitrogen 4.14 mL g (43.3 mmol) of ethylvinyl ether mixed with 70 mL THF were cooled to −78° C. and 25 mL tert-butyllithium (1.7 M in pentane, 43.4 mmol) were added. The mixture was warmed to 0° C. and stirred for 30 min. The mixture was transferred by a cannula to a mixture of 3.69 g (8.65 mmol) intermediate 73 in 130 mL THF at −78° C. The mixture was stirred for 30 min at this temperature 100 mL sat. aqueous solution of ammonium chloride were added and the mixture extracted with ethyl acetate. The solvent was removed under vacuum and the residue purified by MPLC (340 g silica, cyclohexanes/ethyl acetate (90/10 to 60/40 in 70 min). Fractions containing the product were combined and the solvent was evaporated to yield 3.62 g of intermediate 74.

LC-MS (method 2): $t_R$=1.20 min m/z 598/500 Br (M+H$^+$)

$^1$HNMR (DMSO-d6) corresponds with the desired product.

Step 5: Synthesis of Intermediate 75

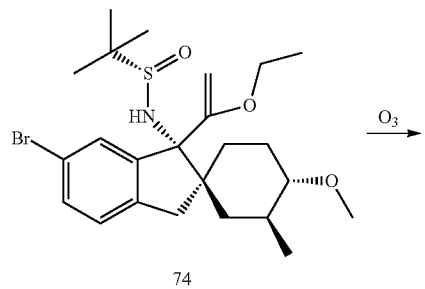

3.62 g (95%, 6.89 mmol) of intermediate 74 were mixed with 60 mL DCM and 15 mL methanol and cooled to −78° C. Ozone was bubbled through the mixture for 20 min. The mixture was purged with $N_2$ and treated with 5 ml (68.4 mmol) $Me_2S$ at −78° C. The reaction was allowed to warm to rt. The solvent was removed under vacuum, the residue was purified by MPLC (340 g silica, cyclohexanes/ethyl acetate (95/25 to 65/35 in 35 min). Fractions containing the product were combined and the solvent was evaporated to yield 2.50 g of intermediate 75.

LC-MS (method 2): $t_R$=1.20 min. m/z 500/2 Br (M+H$^+$)

$^1$HNMR (DMSO-d6) corresponds with the desired product.

Step 6: Synthesis of Intermediate 76

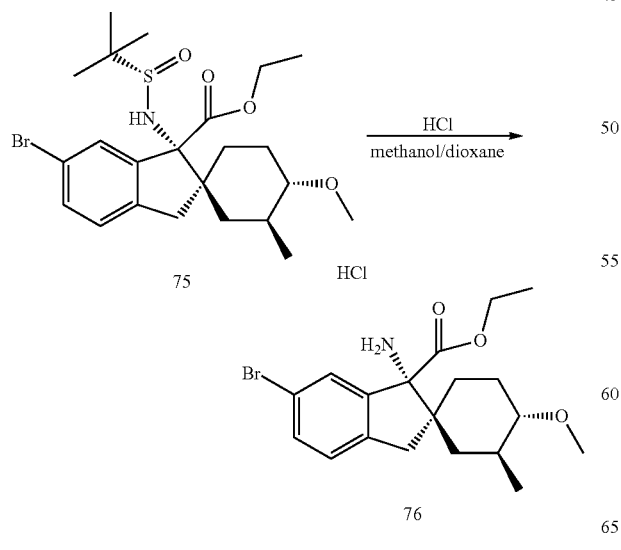

650 mg (0.98 mmol) of intermediate 75 were mixed with 8 ml methanol and 1 ml of a 4 M solution of HCl in 1,4-dioxan was added at 0° C. The mixture was stirred for 2 h at the same temperature. The mixture was evaporated and the remaining crude product 76 used as such for the next step.

LC-MS (method 2): $t_R$=1.20 min. m/z 396/8 Br (M+H$^+$)

$^1$HNMR (DMSO-d6) corresponds with the desired product.

Step 7: Synthesis of Intermediate 77

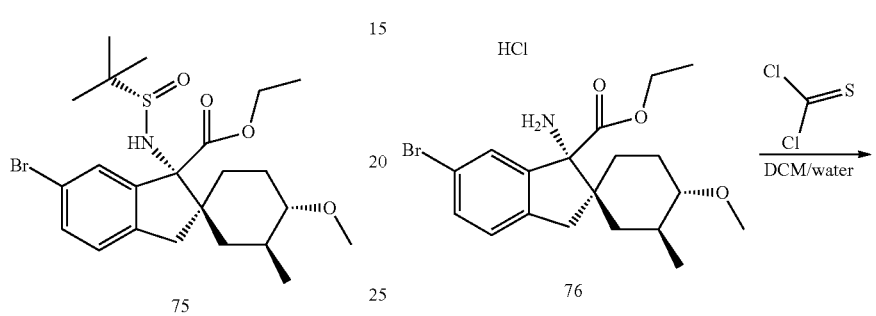

530 mg (1.23 mmol) of intermediate 76 and 675 mg (8.04 mmol) NaHCO$_3$ were mixed with 8 mL water and 4 ml DCM. 188 μL (2.54 mmol) thiophosgene were added at 0° C. while stirring. The mixture was stirred at 0° C. for 1 h. The mixture was extracted with DCM, the solvent evaporated and the remaining crude product 77 used as such for the next step.

LC-MS (method 2) $t_R$=1.74 min m/z 347/9 Br (M+H$^+$)

Step 8: Synthesis of Intermediate 78

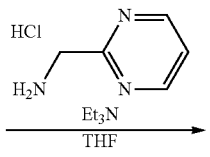

-continued

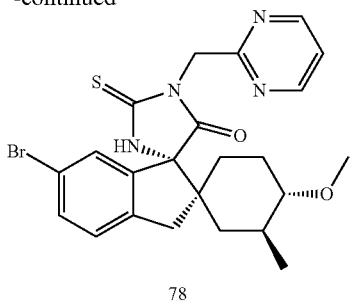

78

510 mg (80%, 0.93 mmol) of 2-aminomethylpyrimidine hydrochloride was mixed with 3 mL THF and 290 μL (2.07 mmol) triethylamine were added. After 5 min, intermediate 77 mixed with 7 mL THF was added, and the mixture was stirred at ambient temperature for 2 h. 290 μL (2.07 mmol) triethylamine were added and the mixture was stirred for an additional 2 h. The mixture was evaporated and the residue purified by MPLC (25 g silica, cyclohexanes/ethyl acetate (110/0 to 70/30 in 50 min). Fractions containing the product were combined and the solvent was evaporated to yield 305 mg of intermediate 78.

LC-MS (method 2): $t_R$=1.00 min. m/z 501/3 Br (M+H$^+$)

$^1$HNMR (DMSO-d6) corresponds with the desired product.

Step 9: Synthesis of Intermediate 79

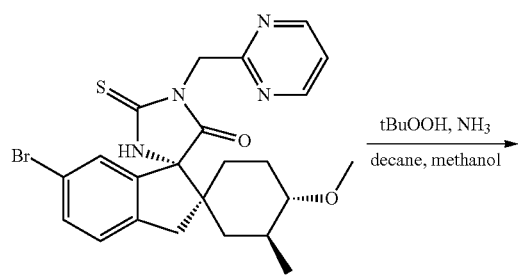

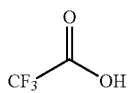

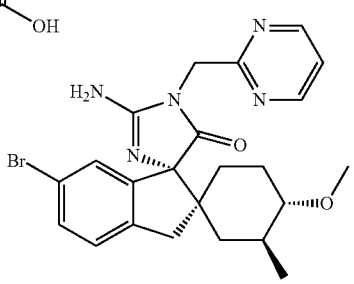

79

303 mg (0.60 mmol) of intermediate 78, 2.65 mL (14.6 mmol, 5.5 M in decane) tert-butyhydroperoxide, 10 mL (70.0 mmol, 7 M in methanol) ammonia were mixed and stirred for 14 h at rt. The mixture was evaporated and the residue purified by HPLC (column: Waters Sunfire; eluent A: water+0.1%

TFA; eluent B: MeOH). Fractions containing the product were combined, the methanol was evaporated and the residue lyophilized to yield 155 mg of the intermediate 79 as trifluoro acetic acid salt.

LC-MS (method 2): $t_R$=1.00 min. m/z 484/6 Br (M+H$^+$)

$^1$HNMR (DMSO-d6) corresponds with the desired product.

Step 10: Synthesis of Intermediate 80

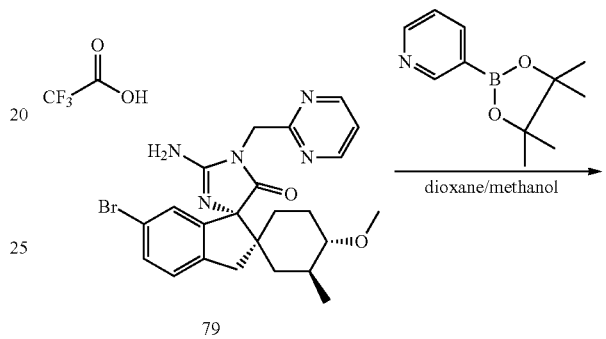

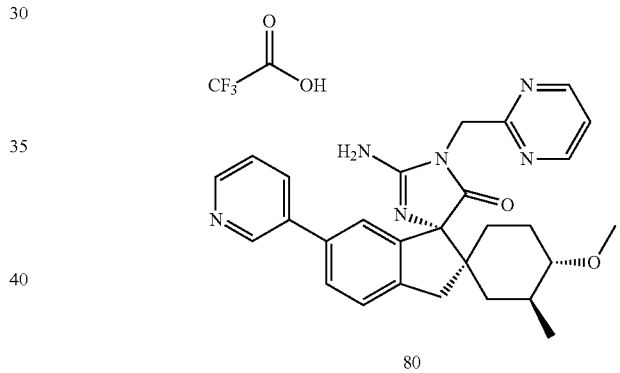

80

70 mg (90%, 0.11 mmol) of intermediate 79, 52.5 mg (0.26 mmol) 2-(3-pyridyl)-4,4,5,5-tetramethyl-1,3,2-dioxaborolane, 16.1 mg 0.022 mmol) chloro(2-dicyclohexylphosphino-2',4',6'-tri-i-propyl-1,1'-biphenyl)[2-(2-aminoethyl)phenyl] palladium(II), 210 μL 2 M aqueous Na$_2$CO$_3$ solution, 1.4 mL dioxane and 0.75 mL methanol were mixed in a microwave vial which was charged with argon. The mixture was stirred 30 min at 140° C. in a microwave oven (Biotage). The mixture was filtered over a thiol cartridge (Agilent Technologies, 500 mg, PL-Thiol MP SPE), the methanol evaporated and the residue purified by HPLC (column: Waters Sunfire; eluent A: water+0.1% TFA; eluent B: MeOH). Fractions containing the product were combined, the methanol was evaporated and the residue lyophilized to yield 56.5 mg of the intermediate 80 as trifluoro acetic acid salt.

LC-MS (method 2): $t_R$=1.00 min. m/z 483 (M+H$^+$)

$^1$HNMR (DMSO-d6) corresponds with the desired product.

Step 11: Synthesis of Example 12

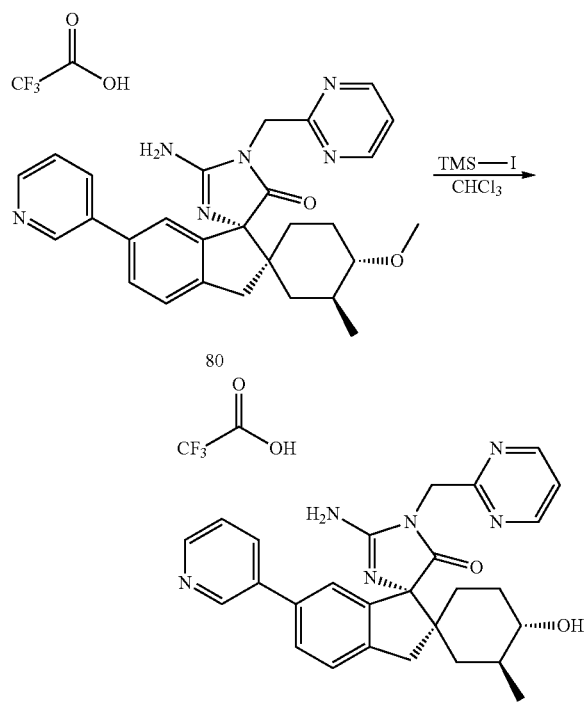

To a suspension of 25 mg (0.042 mmol) of intermediate 80 in 1 mL chloroform were added 30 µL (97%, 0.21 mmol) iodotrimethylsilane and the mixture was stirred for 60 min. The reaction was quenched with 0.5 mL methanol and 5 mL sat. NaHCO₃ aqueous solution and 5 mL 10% Na₂SO₃ aqueous solution were added. The mixture was extracted with ethyl acetate and the combined organic layers dried, evaporated and the residue purified by HPLC (column: Waters Sunfire; eluent A: water+0.1% TFA; eluent B: MeOH). Fractions containing the product were combined, the methanol was evaporated and the remaining residue lyophilized to yield 15.9 mg of Example 12 as trifluoro acetic acid salt.

LC-MS (method 2): $t_R$=0.84 min. m/z 469 (M+H⁺)

¹HNMR (DMSO-d6): δ 10.96 (br s, 1H), 9.58 (br s, 2H), 8.93 (d, 1H), 8.79 (d, 2H), 8.63 (dd, 1H), 8.14 (br d, 1H), 7.76 (dd, 1H), 7.70 (br s, 1H), 7.59 (dd, 1H), 7.51 (m, 2H), 5.18 (d, 1H), 5.08 (d, 1H), 4.30 (br s, OH) 3.16 (d, 1H), 3.02 (d, 1H), 2.94 (m, 1H), 1.78 (m, 1H), 1.58-1.24 (m, 6H), 0.92 (d, 3H).

Example 13

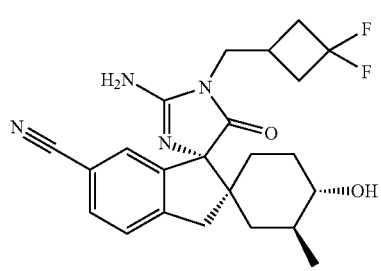

Example 13

Step 1: Synthesis of Intermediate 81

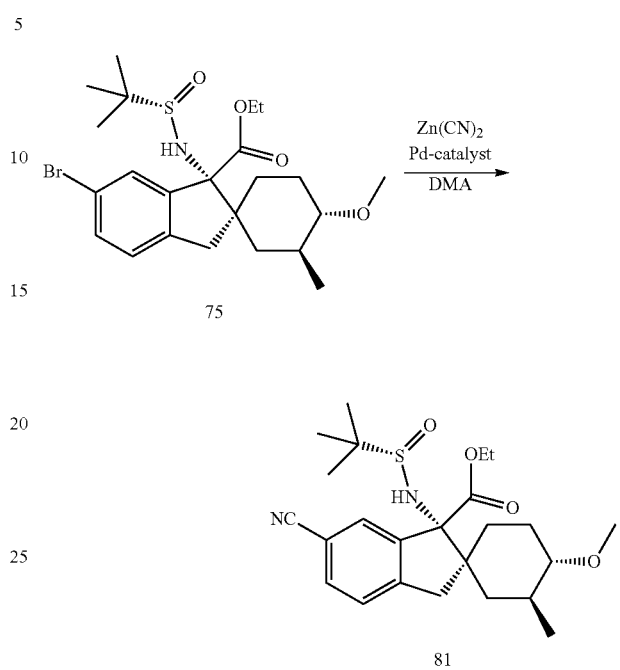

1.58 g (90%, 2.84 mmol) of intermediate 75 were mixed with 60 mL DMA and argon was bubbled through the mixture. Zinc cyanide (556 mg, 4.74 mmol) and chloro(2-dicyclohexylphosphino-2',4',6'-tri-1-propyl-1,1'-biphenyl)[2-(2-aminoethyl)phenyl]palladium(II) (690 mg, 0.93 mmol) were added at rt. The mixture was stirred for 20 min at 120° C. After this, the mixture was evaporated at 3 mbar at 70° C., and the residue was mixed with water and ethyl acetate, filtered over celite, and the phases separated. The aqueous phase was extracted with ethyl acetate, and the organic phases were combined, dried and evaporated. The residue was purified by MPLC (100 g silica, CH/EE 80/20 to 55/45 in 70 min). Fractions containing the product were combined to give 1.17 g of intermediate 81.

LC-MS (method 2): $t_R$=1.40 min. m/z 447 (M+H⁺)

¹HNMR (DMSO-d6) corresponds with the desired product.

Step 2: Synthesis of Intermediate 82

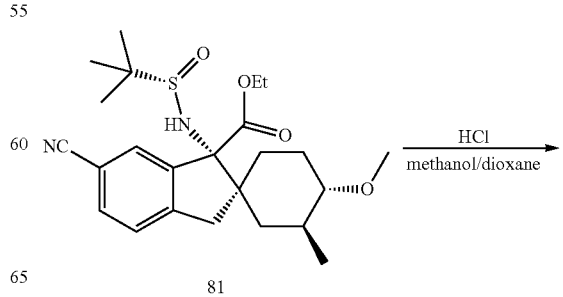

-continued

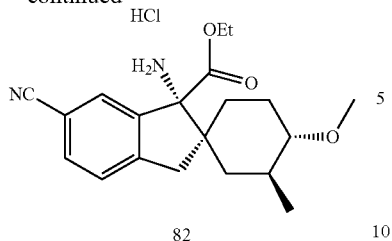

82

Intermediate 82 was synthesized by a method described in Example 12 step 6 from 4.00 g (80%, 7.17 mmol) intermediate 81. 4.13 g of the crude product were obtained and used as such in the next step.

LC-MS (method 2): $t_R$=1.11 min. m/z 343 (M+H$^+$)

$^1$HNMR (DMSO-d6) corresponds with the desired product.

Step 3: Synthesis of Intermediate 83

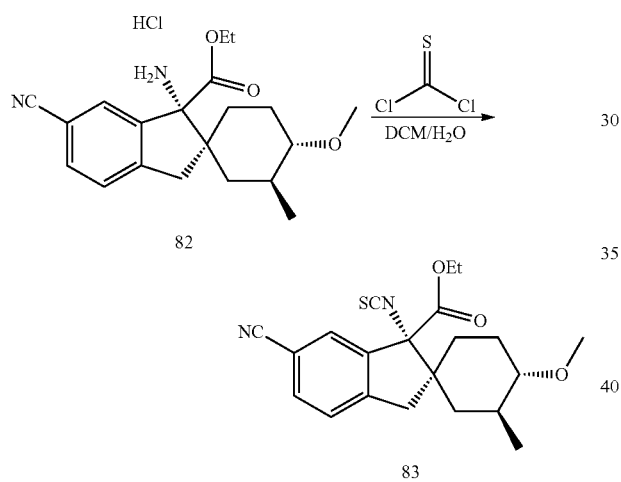

Intermediate 83 was synthesized by a method described in Example 12 step 7 from 4.13 g (70%, 7.63 mmol) intermediate 82. 4.6 g of the crude product were obtained and used as such in the next step.

LC-MS (method 2): $t_R$=1.58 min. m/z 294 (M+H$^+$)

Step 4: Synthesis of Intermediate 84

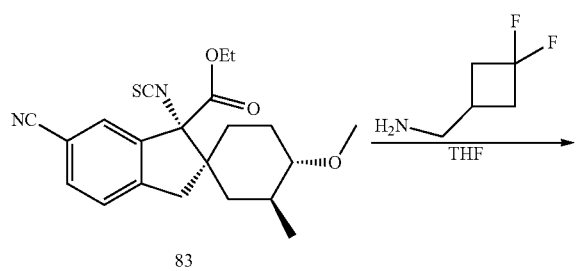

-continued

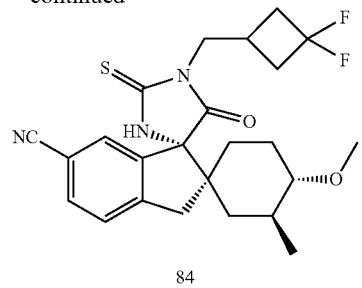

84

Intermediate 84 was synthesized in accordance with the method described in Example 12, step 8, from 200 mg (0.33 mmol) intermediate 83. Instead of 2-aminomethylpyrimidine hydrochloride, 63 mg (0.49 mmol) 3,3-difluorocyclobutyl)methanamine and 3 equivalents of triethylamine were used. The crude product was purified by MPLC (25 g silica, CH/EE 65/35 in 45 min) to yield 141 mg of intermediate 84.

LC-MS (method 2): $t_R$=1.53 min. m/z 460 (M+H$^+$)

Step 5: Synthesis of Intermediate 85

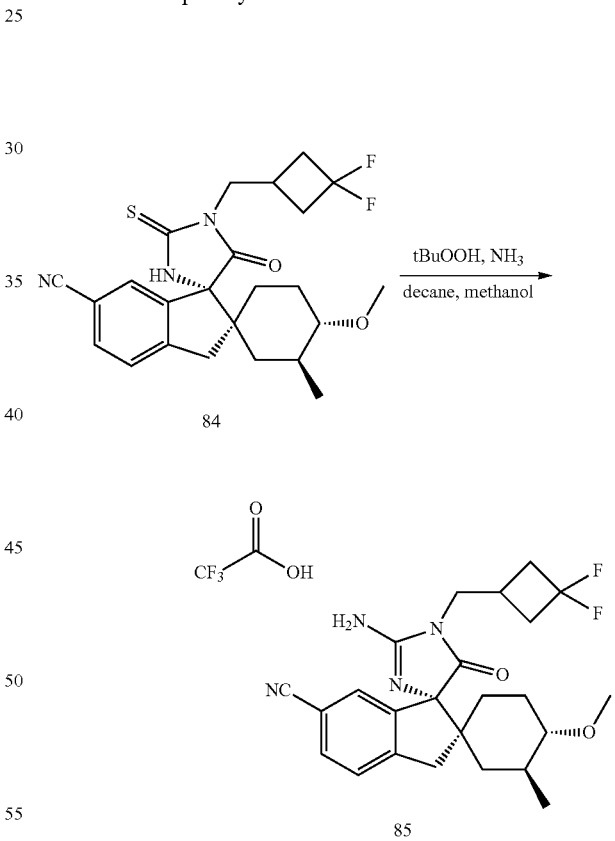

Intermediate 85 was synthesized by in accordance with the method described in Example 12, step 9 using 139 mg (0.30 mmol) of intermediate 84. The crude product was purified by HPLC (column: Waters Sunfire; eluent A: water+0.1% TFA; eluent B: MeOH) to yield 96.8 mg of intermediate 85 as trifluoroacetic acid salt.

LC-MS (method 2): $t_R$=1.19 min. m/z 443 (M+H$^+$)

$^1$HNMR (DMSO-d6) corresponds with the desired product.

Step 6: Synthesis of Example 13

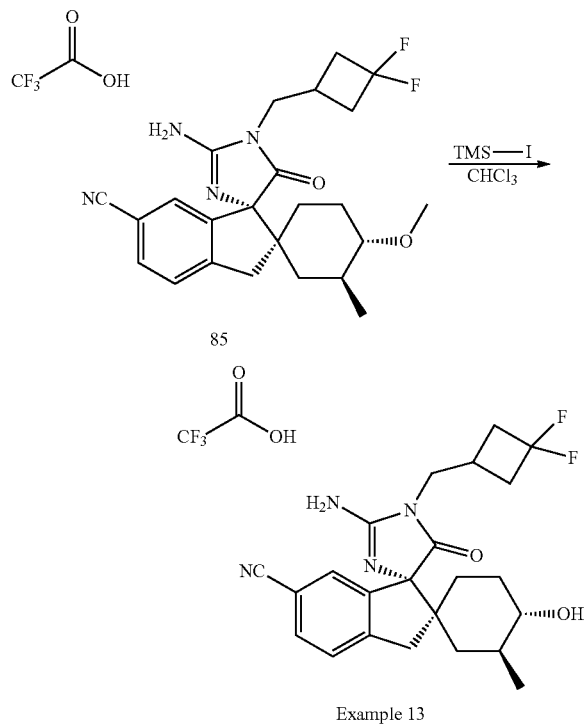

85

Example 13

Example 13 was synthesized in accordance with the method described in Example 12, step 11 using 40 mg (0.072 mmol) of intermediate 85. The crude product was purified by HPLC (column: Waters Sunfire; eluent A: water+0.1% TFA; eluent B: MeOH) to yield 20 mg of Example 13.

LC-MS (method 2): $t_R$=0.88 min. m/z 429 (M+H$^+$)

$^1$HNMR (DMSO-d6): δ 10.83 (br s, 1H), 9.65 (br s, 2H), 7.90 (d, 1H), 7.84 (dd, 1H), 7.59 (d, 1H), 4.35 (br s, OH), 3.78 (m, 2H), 3.20 (d, 1H), 3.03 (d, 1H), 2.88 (m, 1H), 2.68-2.26 (m, 5H), 1.72 (m, 1H), 1.54 (m, 1H), 1.45-1.28 (m, 3H), 1.16 (m, 1H), 1.05 (t, 1H), 0.91 (d, 3H).

Example 14

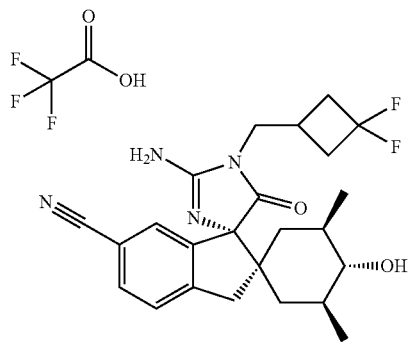

Example 14

Example 14 was synthesized by the method described in Example 13 using intermediate 17 instead of intermediate 75 in step 1.

LC-MS (method 3): $t_R$=0.96 min m/z 443 (M+H$^+$)

$^1$HNMR (DMSO-d6): δ 10.85 (br s, 1H), 9.65 (br s, 2H), 7.88 (d, 1H), 7.84 (dd, 1H), 7.59 (d, 1H), 4.40 (br s, OH), 3.78 (m, 2H), 3.20 (d, 1H), 3.06 (d, 1H), 2.68-2.26 (m, 6H), 1.60-1.04 (m, 6H), 0.92 (d, 3H), 0.88 (d, 3H).

Example 15

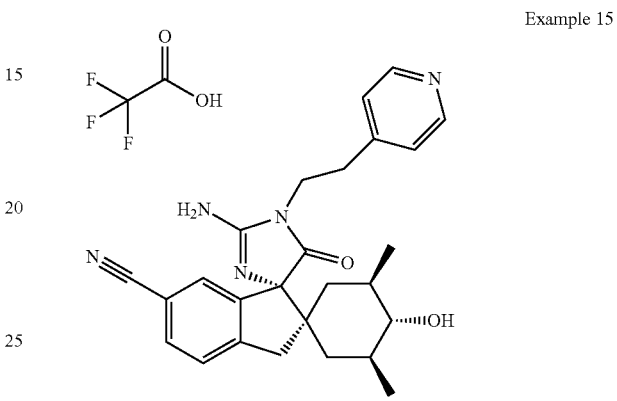

Example 15

Example 15 was synthesized by the method described in Example 13 using intermediate 17 instead of intermediate 75 in step 1 and 2-pyridin-4-yl-ethylamine instead of 3,3-difluorocyclobutyl)methanamine in step 4.

LC-MS (method 3): $t_R$=0.96 min m/z 444.5 (M+H$^+$)

$^1$HNMR (DMSO-d6): δ 10.81 (br s, 1H), 9.70 (br s, 2H), 8.55 (d, 2H), 7.84 (br s, 1H), 7.83 (dd, 1H), 7.55 (m, 3H), 4.30 (br s, OH), 4.06-3.90 (m, 2H), 3.16-2.96 (m, 4H), 2.40 (t, 1H), 1.49 (m, 1H), 1.35 (m, 2H), 1.18 (m, 1H), 1.02-0.90 (m, 2H), 0.88 (d, 3H), 0.86 (d, 3H).

Example 16

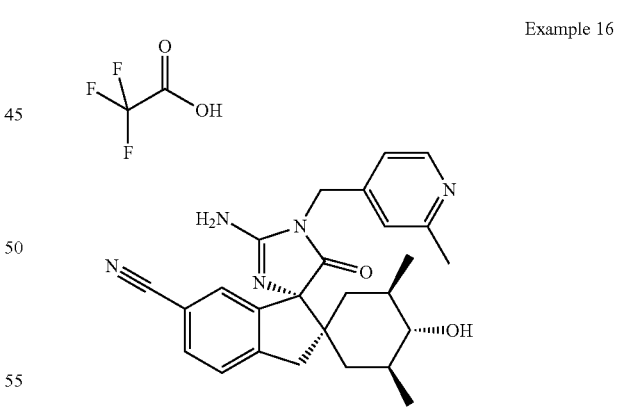

Example 16

Example 16 was synthesized by the method described in Example 13 using intermediate 17 instead of intermediate 75 in step 1 and (2-methyl-pyridin-4-yl)-methylamine instead of 3,3-difluorocyclobutyl)methanamine in step 4.

LC-MS (method 4): $t_R$=0.82 min. m/z 444 (M+H$^+$)

$^1$HNMR (DMSO-d6): δ 10.96 (br s, 1H), 9.70 (br s, 2H), 8.52 (d, 1H), 7.98 (d, 1H), 7.85 (dd, 1H), 7.60 (d, 1H), 7.32 (d, 1H), 7.28 (br s, 1H), 4.93 (s, 2H), 4.30 (br s, OH), 3.20 (d, 1H), 3.03 (d, 1H), 2.52 (s, 3H), 2.47 (m, 1H), 1.59-1.10 (m, 6H), 0.90 (d, 3H), 0.88 (d, 3H).

The invention claimed is:
1. A compound represented by a structural formula selected from:
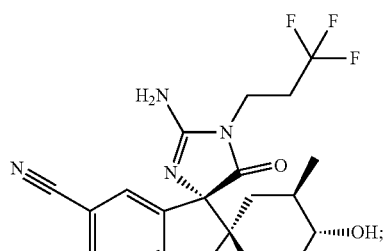
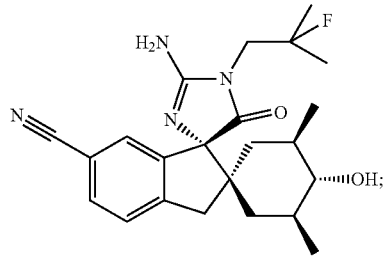
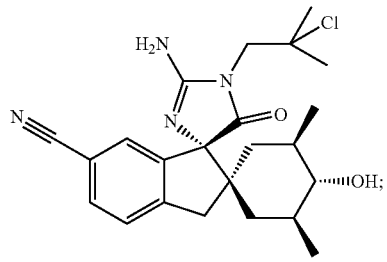
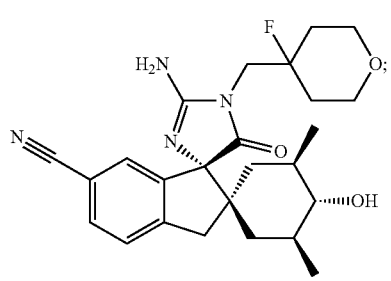
-continued
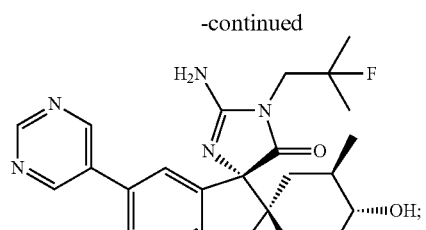
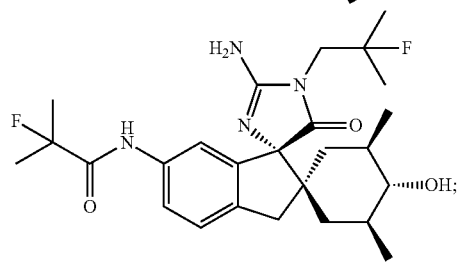
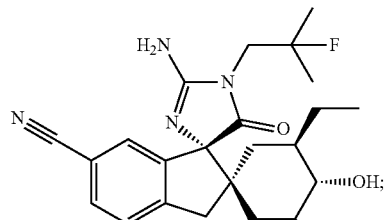
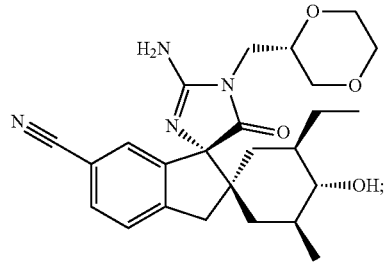
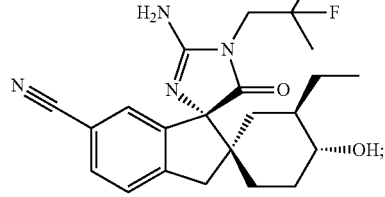

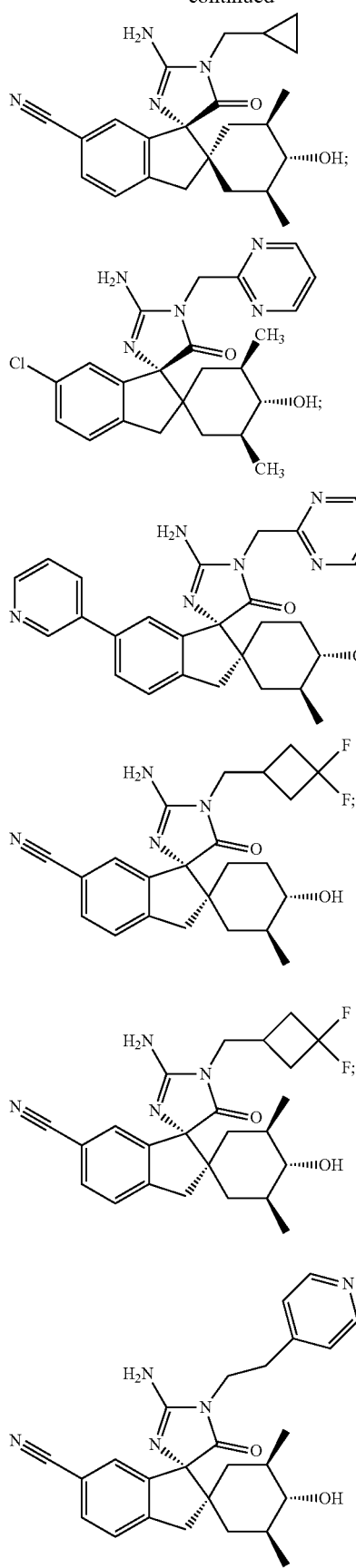

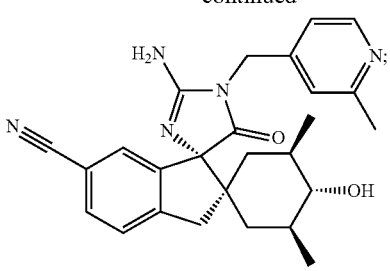

or a pharmaceutically acceptable salt thereof.

2. A pharmaceutical composition comprising at least one compound according to claim 1 or a pharmaceutically acceptable salt thereof in admixture with a pharmaceutically acceptable adjuvant, diluent and/or carrier.

3. A method of treating a BACE1 mediated disorder or disease in a subject, comprising administering to the subject an effective amount of a compound represented by a structural formula selected from:

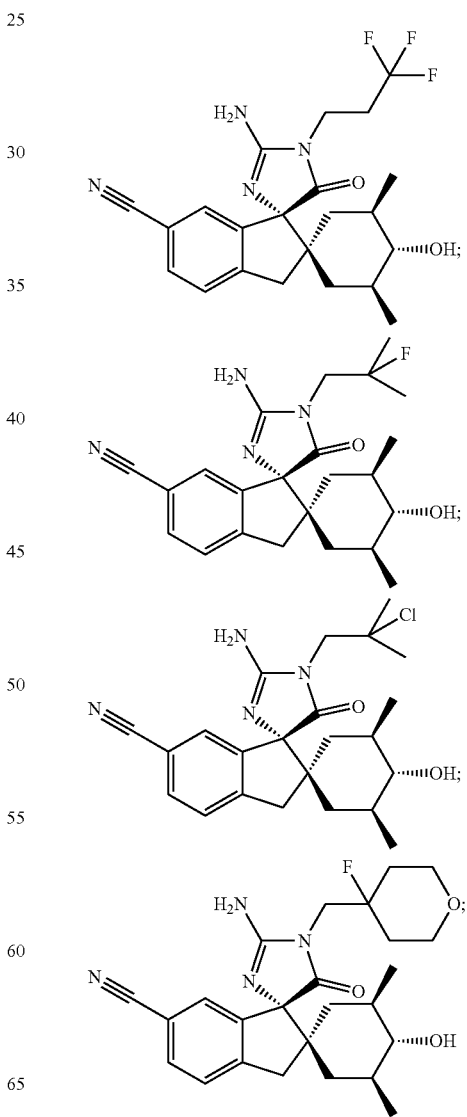

89
-continued
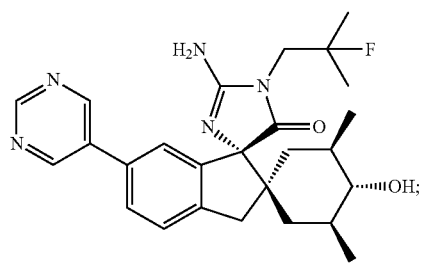
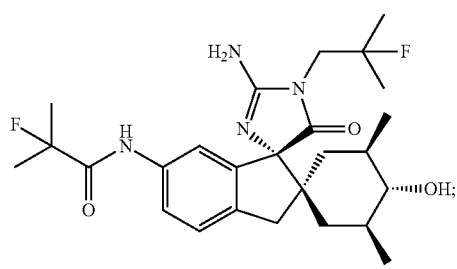
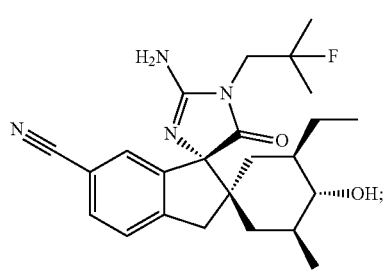
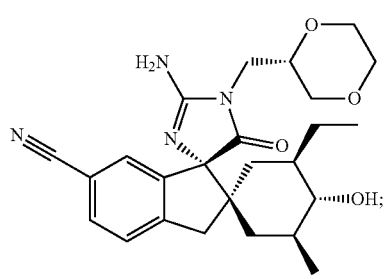
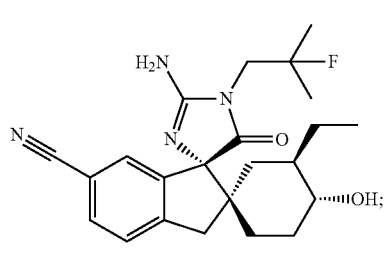
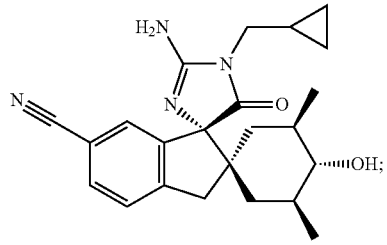
90
-continued
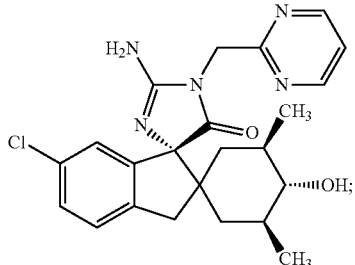
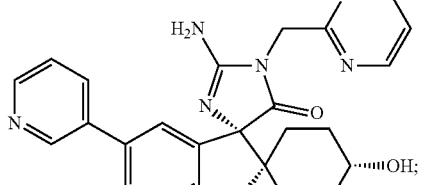
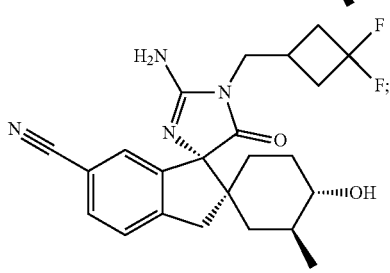
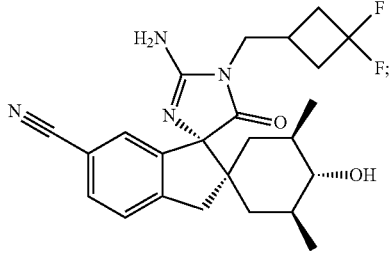
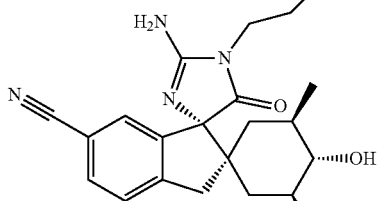; and
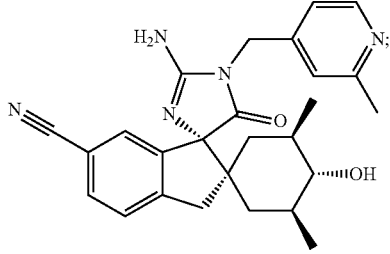;
or a pharmaceutically acceptable salt thereof, wherein the disorder or disease is Alzheimer's disease or glaucoma.

4. The method of claim 3, wherein the disorder or disease is Alzheimer's disease.

5. The method according to claim 3, wherein the disorder or disease is glaucoma.

6. A compound selected from the group consisting of:

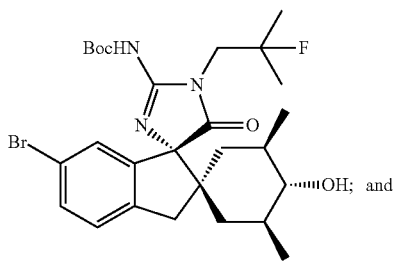

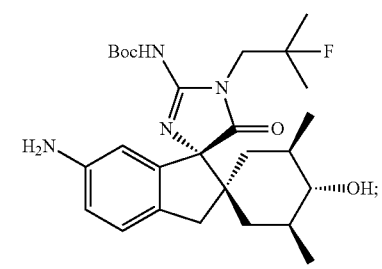

or a salt thereof.

7. A compound represented by the following structural formula:

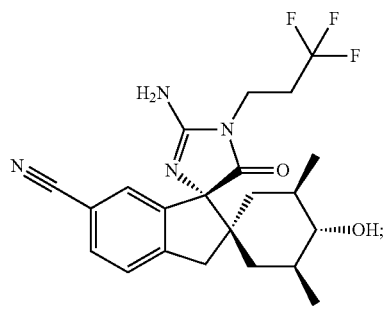 [SMILES: C[C@@H]1C[C@@]2(Cc3ccc(C#N)cc3[C@]23N=C(N)N(CCC(F)(F)F)C3=O)C[C@H](C)[C@H]1O]

or a pharmaceutically acceptable salt thereof.

8. A compound represented by the following structural formula:

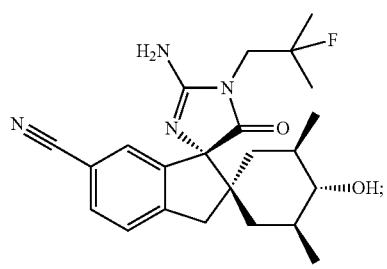 [SMILES: C[C@@H]1C[C@@]2(Cc3ccc(C#N)cc3[C@]23N=C(N)N(CC(C)(C)F)C3=O)C[C@H](C)[C@H]1O]

or a pharmaceutically acceptable salt thereof.

9. A compound represented by the following structural formula:

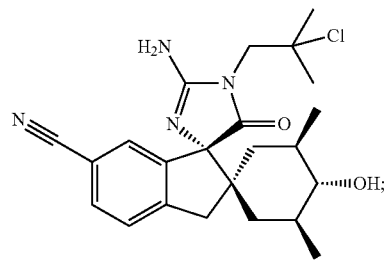 [SMILES: C[C@@H]1C[C@@]2(Cc3ccc(C#N)cc3[C@]23N=C(N)N(CC(C)(C)Cl)C3=O)C[C@H](C)[C@H]1O]

or a pharmaceutically acceptable salt thereof.

10. A compound represented by the following structural formula:

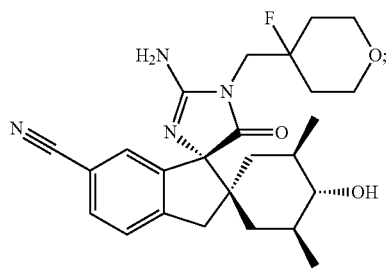 [SMILES: C[C@@H]1C[C@@]2(Cc3ccc(C#N)cc3[C@]23N=C(N)N(CC2(F)CCOCC2)C3=O)C[C@H](C)[C@H]1O]

or a pharmaceutically acceptable salt thereof.

11. A compound represented by the following structural formula:

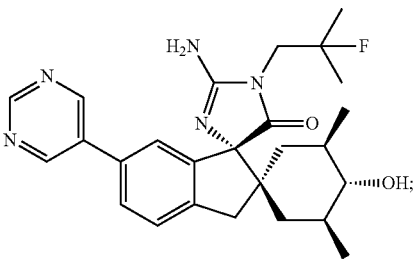 [SMILES: C[C@@H]1C[C@@]2(Cc3ccc(-c4cncnc4)cc3[C@]23N=C(N)N(CC(C)(C)F)C3=O)C[C@H](C)[C@H]1O]

or a pharmaceutically acceptable salt thereof.

12. A compound represented by the following structural formula:

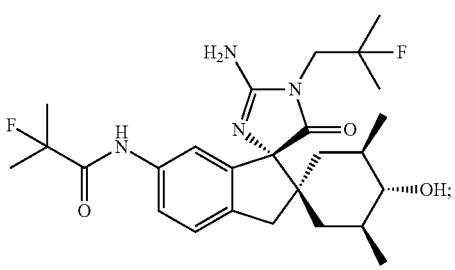 [SMILES: C[C@@H]1C[C@@]2(Cc3ccc(NC(=O)C(C)(C)F)cc3[C@]23N=C(N)N(CC(C)(C)F)C3=O)C[C@H](C)[C@H]1O]

or a pharmaceutically acceptable salt thereof.

13. A compound represented by the following structural formula:

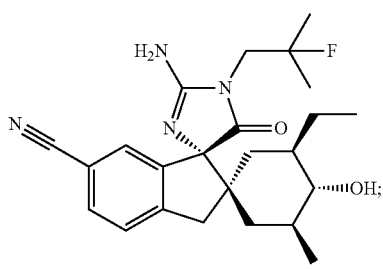 [SMILES: CC[C@@H]1C[C@@]2(Cc3ccc(C#N)cc3[C@]23N=C(N)N(CC(C)(C)F)C3=O)C[C@H](C)[C@H]1O]

or a pharmaceutically acceptable salt thereof.

14. A compound represented by the following structural formula:

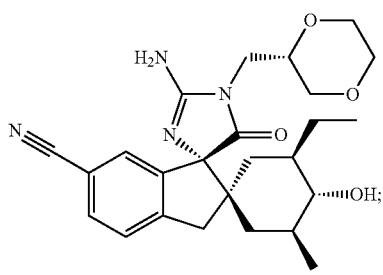 [SMILES: CC[C@@H]1C[C@@]2(Cc3ccc(C#N)cc3[C@]23N=C(N)N(C[C@H]2COCCO2)C3=O)C[C@H](C)[C@H]1O]

or a pharmaceutically acceptable salt thereof.

15. A compound represented by the following structural formula:

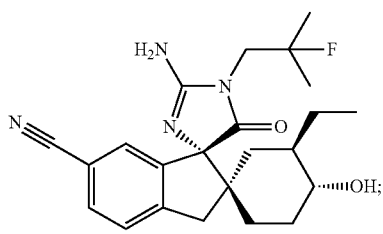 [SMILES: CC[C@@H]1C[C@]2(CC[C@H]1O)Cc1ccc(C#N)cc1[C@]21N=C(N)N(CC(C)(C)F)C1=O]

or a pharmaceutically acceptable salt thereof.

16. A compound represented by the following structural formula:

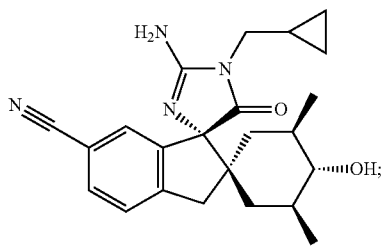 [SMILES: C[C@@H]1C[C@@]2(Cc3ccc(C#N)cc3[C@]23N=C(N)N(CC2CC2)C3=O)C[C@H](C)[C@H]1O]

or a pharmaceutically acceptable salt thereof.

17. A compound represented by the following structural formula:

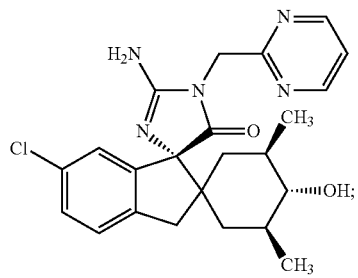 [SMILES: C[C@@H]1CC2(Cc3ccc(Cl)cc3[C@]23N=C(N)N(Cc2ncccn2)C3=O)C[C@H](C)[C@H]1O]

or a pharmaceutically acceptable salt thereof.

18. A compound represented by the following structural formula:

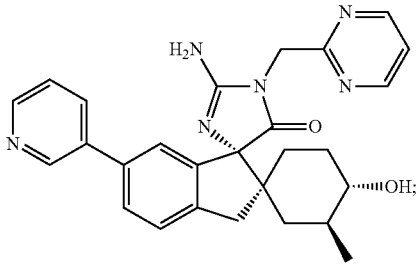 [SMILES: C[C@H]1C[C@@]2(CC[C@@H]1O)Cc1ccc(-c3cccnc3)cc1[C@]21N=C(N)N(Cc2ncccn2)C1=O]

or a pharmaceutically acceptable salt thereof.

19. A compound represented by the following structural formula:

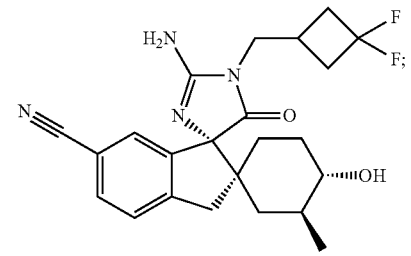 [SMILES: C[C@H]1C[C@@]2(CC[C@@H]1O)Cc1ccc(C#N)cc1[C@]21N=C(N)N(CC2CC(F)(F)C2)C1=O]

or a pharmaceutically acceptable salt thereof.

20. A compound represented by the following structural formula:

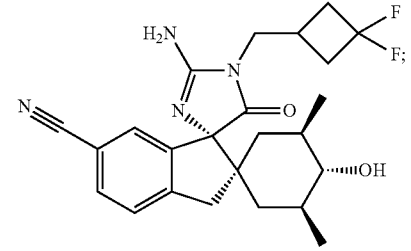 [SMILES: C[C@@H]1C[C@@]2(Cc3ccc(C#N)cc3[C@]23N=C(N)N(CC2CC(F)(F)C2)C3=O)C[C@H](C)[C@H]1O]

or a pharmaceutically acceptable salt thereof.

21. A compound represented by the following structural formula:

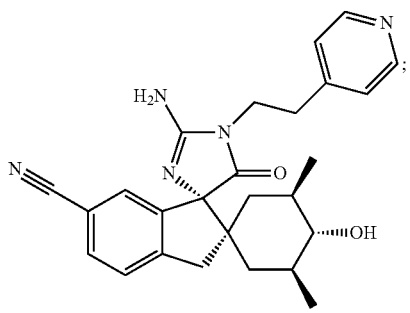 [SMILES: C[C@@H]1C[C@@]2(Cc3ccc(C#N)cc3[C@]23N=C(N)N(CCc2ccncc2)C3=O)C[C@H](C)[C@H]1O]

or a pharmaceutically acceptable salt thereof.

22. A compound represented by the following structural formula:

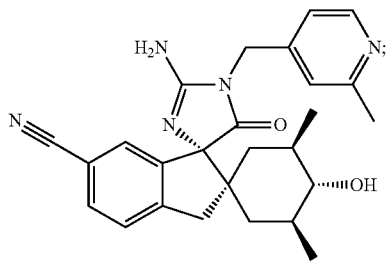 [SMILES: Cc1cc(CN2C(=O)[C@]3(N=C2N)c2cc(C#N)ccc2C[C@@]32C[C@@H](C)[C@H](O)[C@@H](C)C2)ccn1]

or a pharmaceutically acceptable salt thereof.

23. The method of claim 4, wherein the compound is represented by the following structural formula:

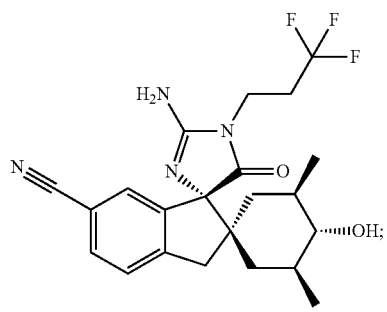 [SMILES: C[C@@H]1C[C@@]2(Cc3ccc(C#N)cc3[C@]23N=C(N)N(CCC(F)(F)F)C3=O)C[C@H](C)[C@H]1O]

or a pharmaceutically acceptable salt thereof.

24. The method of claim 4, wherein the compound is represented by the following structural formula:

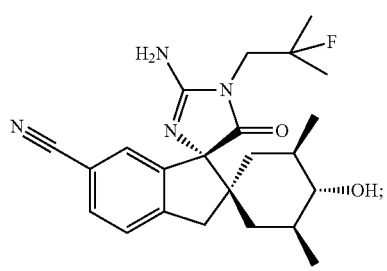 [SMILES: C[C@@H]1C[C@@]2(Cc3ccc(C#N)cc3[C@]23N=C(N)N(CC(C)(C)Cl)C3=O)C[C@H](C)[C@H]1O]

or a pharmaceutically acceptable salt thereof.

25. The method of claim 4, wherein the compound is represented by the following structural formula:

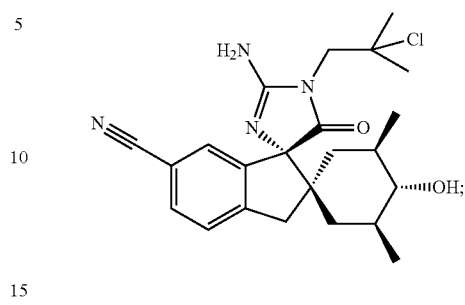

or a pharmaceutically acceptable salt thereof.

26. The method of claim 4, wherein the compound is represented by the following structural formula:

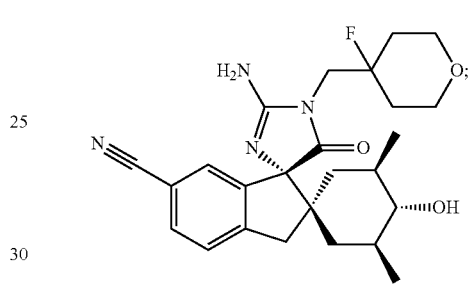

or a pharmaceutically acceptable salt thereof.

27. The method of claim 4, wherein the compound is represented by the following structural formula:

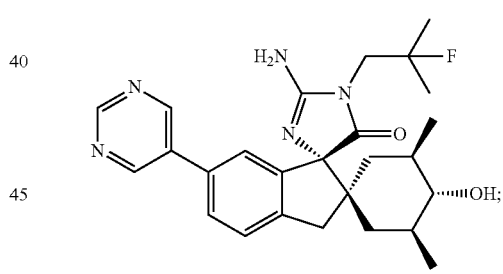

or a pharmaceutically acceptable salt thereof.

28. The method of claim 4, wherein the compound is represented by the following structural formula:

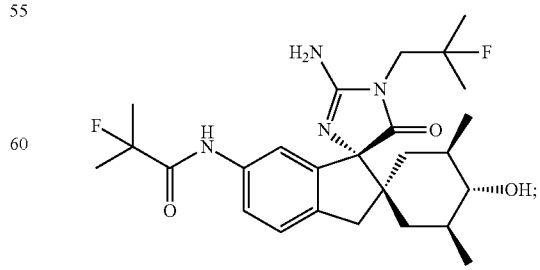

or a pharmaceutically acceptable salt thereof.

29. The method of claim 4, wherein the compound is represented by the following structural formula:

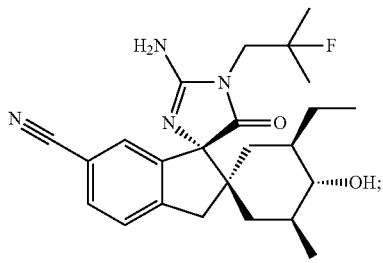 [SMILES: CC[C@@H]1C[C@@]2(Cc3ccc(C#N)cc3[C@]23N=C(N)N(CC(C)(C)F)C3=O)C[C@H](C)[C@H]1O]

or a pharmaceutically acceptable salt thereof.

30. The method of claim 4, wherein the compound is represented by the following structural formula:

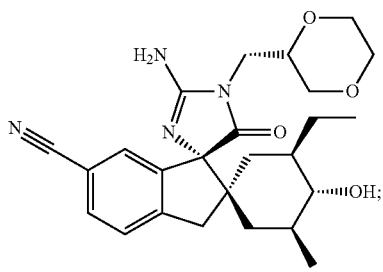

or a pharmaceutically acceptable salt thereof.

31. The method of claim 4, wherein the compound is represented by the following structural formula:

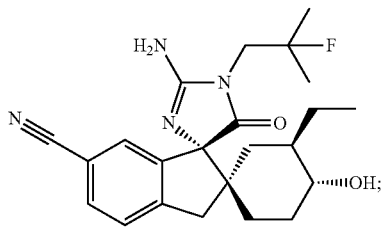 [SMILES: CC[C@@H]1C[C@]2(CC[C@H]1O)Cc1ccc(C#N)cc1[C@]21N=C(N)N(CC(C)(C)F)C1=O]

or a pharmaceutically acceptable salt thereof.

32. The method of claim 4, wherein the compound is represented by the following structural formula:

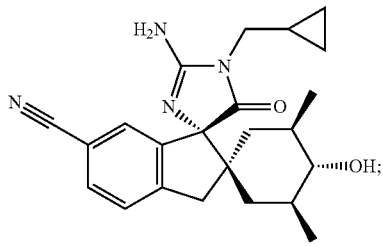 [SMILES: C[C@@H]1C[C@@]2(Cc3ccc(C#N)cc3[C@]23N=C(N)N(CC2CC2)C3=O)C[C@H](C)[C@H]1O]

or a pharmaceutically acceptable salt thereof.

33. The method of claim 4, wherein the compound is represented by the following structural formula:

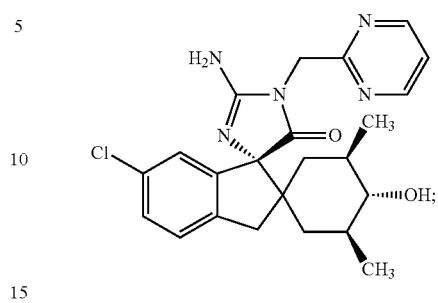

or a pharmaceutically acceptable salt thereof.

34. The method of claim 4, wherein the compound is represented by the following structural formula:

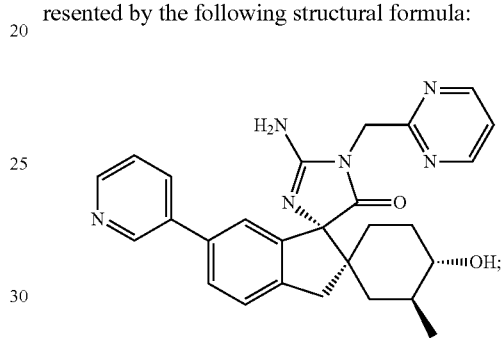

or a pharmaceutically acceptable salt thereof.

35. The method of claim 4, wherein the compound is represented by the following structural formula:

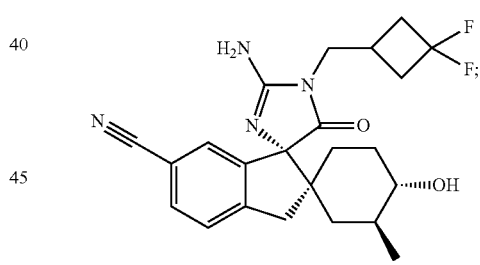

or a pharmaceutically acceptable salt thereof.

36. The method of claim 4, wherein the compound is represented by the following structural formula:

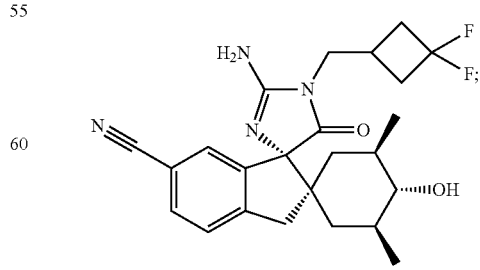

or a pharmaceutically acceptable salt thereof.

37. The method of claim 4, wherein the compound is represented by the following structural formula:
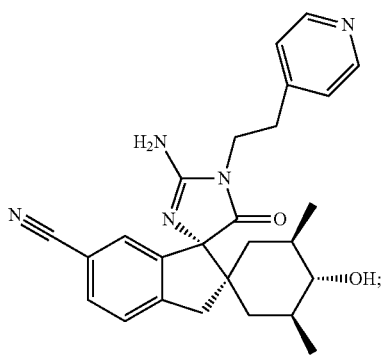 [SMILES: C[C@@H]1C[C@@]2(Cc3ccc(C#N)cc3[C@]23N=C(N)N(CCc2ccncc2)C3=O)C[C@H](C)[C@H]1O]
or a pharmaceutically acceptable salt thereof.
38. The method of claim 4, wherein the compound is represented by the following structural formula:
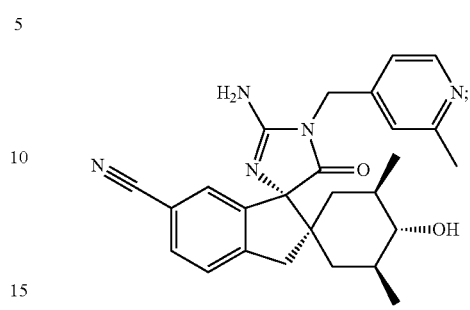
or a pharmaceutically acceptable salt thereof.
* * * * *